(12) United States Patent
Zimmerman et al.

(10) Patent No.: US 11,896,255 B2
(45) Date of Patent: Feb. 13, 2024

(54) END-EFFECTOR JAW CLOSURE TRANSMISSION SYSTEMS FOR REMOTE ACCESS TOOLS

(71) Applicant: FlexDex, Inc., Brighton, MI (US)

(72) Inventors: Zachary Zimmerman, Waterford, MI (US); Shorya Awtar, Ann Arbor, MI (US); Bruce Johnson, Elkins, NH (US); Christopher K. Holmes, Harvard, MA (US); Peter F. Costa, Winthrop, MA (US); Ryan Brook Rank, Ann Arbor, MI (US); Deepak Sharma, Ann Arbor, MI (US); Matthew P. Weber, Brighton, MI (US)

(73) Assignee: FlexDex, Inc., Brighton, MI (US)

( * ) Notice: Subject to any disclaimer, the term of this patent is extended or adjusted under 35 U.S.C. 154(b) by 644 days.

(21) Appl. No.: 17/084,615

(22) Filed: Oct. 29, 2020

(65) Prior Publication Data

US 2021/0045765 A1     Feb. 18, 2021

Related U.S. Application Data

(63) Continuation-in-part of application No. 15/946,612, filed on Apr. 5, 2018, now abandoned, which is a continuation of application No. PCT/US2016/055606, filed on Oct. 5, 2016.

(60) Provisional application No. 62/237,483, filed on Oct. 5, 2015, provisional application No. 62/237,476, filed on Oct. 5, 2015.

(51) Int. Cl.
*A61B 17/29* (2006.01)
*A61B 90/00* (2016.01)

(52) U.S. Cl.
CPC .......... *A61B 17/2909* (2013.01); *A61B 90/03* (2016.02); *A61B 2017/2913* (2013.01); *A61B 2017/2939* (2013.01); *A61B 2017/2947* (2013.01)

(58) Field of Classification Search
CPC ........ A61B 17/2909; A61B 2017/2913; A61B 2017/2939; A61B 90/03; A61B 34/71; A61B 2017/2926–2945
See application file for complete search history.

(56) References Cited

U.S. PATENT DOCUMENTS

| 331,598 A | 12/1885 | White |
| 3,028,126 A | 4/1962 | Holleman |
| 3,350,956 A | 11/1967 | Barton |

(Continued)

FOREIGN PATENT DOCUMENTS

| CN | 101610709 A | 12/2009 |
| CN | 101711703 A | 5/2010 |

(Continued)

OTHER PUBLICATIONS

Awtar et al.; A minimally invasive surgical tool with enhanced dexterity and intuitive actuation; J. Med. Devices; 4(3); 8 pages; (Author's Draft; 12 pages); Sep. 10, 2010.

(Continued)

*Primary Examiner* — Darwin P Erezo
*Assistant Examiner* — Brigid K Byrd
(74) *Attorney, Agent, or Firm* — Shay Glenn LLP

(57) ABSTRACT

A jaw closure transmission system is presented comprising an input sub-system, output sub-system and a transmission sub-system.

22 Claims, 37 Drawing Sheets

(56) References Cited

U.S. PATENT DOCUMENTS

| | | | |
|---|---|---|---|
| 3,497,083 A | 2/1970 | Anderson et al. | |
| 3,656,235 A | 4/1972 | Zuurveen | |
| 4,328,839 A | 5/1982 | Lyons et al. | |
| 4,466,649 A | 8/1984 | Ozawa | |
| 4,491,325 A | 1/1985 | Bersheim | |
| 4,568,311 A | 2/1986 | Miyake | |
| 4,613,179 A | 9/1986 | van Zelm | |
| 4,712,545 A | 12/1987 | Honkanen | |
| 4,740,126 A | 4/1988 | Richter | |
| 4,750,475 A | 6/1988 | Yoshihashi | |
| 4,754,909 A | 7/1988 | Barker et al. | |
| 4,758,035 A | 7/1988 | Shimasaki | |
| 4,950,273 A | 8/1990 | Briggs | |
| 4,993,766 A | 2/1991 | Sutherland | |
| 5,021,969 A | 6/1991 | Okamura et al. | |
| 5,069,596 A | 12/1991 | Mueller et al. | |
| 5,147,357 A * | 9/1992 | Rose | A61B 17/29 606/49 |
| 5,193,963 A | 3/1993 | McAffee et al. | |
| 5,209,747 A | 5/1993 | Knoepfler | |
| 5,297,443 A | 3/1994 | Wentz | |
| 5,317,952 A | 6/1994 | Immega | |
| 5,323,570 A | 6/1994 | Kuhlman et al. | |
| 5,330,502 A | 7/1994 | Hassler et al. | |
| 5,350,391 A | 9/1994 | Iacovelli | |
| 5,368,600 A | 11/1994 | Failla et al. | |
| 5,374,277 A | 12/1994 | Hassler | |
| 5,379,663 A | 1/1995 | Hara | |
| 5,379,758 A | 1/1995 | Snyder | |
| 5,454,827 A | 10/1995 | Aust et al. | |
| 5,456,695 A | 10/1995 | Herve Dallemagne | |
| 5,465,894 A * | 11/1995 | Clark | A61B 17/072 227/19 |
| 5,549,637 A | 8/1996 | Crainich | |
| 5,560,532 A | 10/1996 | DeFonzo et al. | |
| 5,599,151 A | 2/1997 | Daum et al. | |
| 5,619,195 A | 4/1997 | Allen et al. | |
| 5,620,415 A | 4/1997 | Lucey et al. | |
| 5,626,608 A | 5/1997 | Cuny et al. | |
| 5,683,412 A | 11/1997 | Scarfone | |
| 5,713,505 A | 2/1998 | Huitema | |
| 5,716,352 A | 2/1998 | Viola et al. | |
| 5,735,874 A | 4/1998 | Measamer et al. | |
| 5,782,748 A | 7/1998 | Palmer et al. | |
| 5,807,376 A | 9/1998 | Viola et al. | |
| 5,813,813 A | 9/1998 | Daum et al. | |
| 5,816,770 A | 10/1998 | Itagaki | |
| 5,817,084 A | 10/1998 | Jensen | |
| 5,820,009 A | 10/1998 | Melling et al. | |
| 5,853,412 A | 12/1998 | Mayenberger | |
| 5,860,995 A | 1/1999 | Berkelaar | |
| 5,908,436 A | 6/1999 | Cuschieri et al. | |
| 6,042,555 A | 3/2000 | Kramer et al. | |
| 6,088,020 A | 7/2000 | Mor et al. | |
| 6,104,379 A | 8/2000 | Petrich et al. | |
| 6,270,453 B1 | 8/2001 | Sakai | |
| 6,309,403 B1 | 10/2001 | Minor et al. | |
| 6,312,435 B1 | 11/2001 | Wallace et al. | |
| 6,330,837 B1 | 12/2001 | Charles et al. | |
| 6,413,229 B1 | 7/2002 | Kramer et al. | |
| 6,607,475 B2 | 8/2003 | Doyle et al. | |
| 6,707,447 B1 | 3/2004 | Goranowski | |
| 6,714,839 B2 | 3/2004 | Salisbury et al. | |
| 6,853,879 B2 | 2/2005 | Sunaoshi | |
| 6,858,005 B2 | 2/2005 | Ohline et al. | |
| 6,889,116 B2 | 5/2005 | Jinno | |
| 6,994,716 B2 | 2/2006 | Jinno et al. | |
| 7,101,363 B2 | 9/2006 | Nishizawa et al. | |
| 7,147,650 B2 | 12/2006 | Lee | |
| 7,338,513 B2 | 3/2008 | Lee et al. | |
| 7,410,338 B2 | 8/2008 | Schiele et al. | |
| 7,470,268 B2 | 12/2008 | Doyle et al. | |
| 7,553,275 B2 | 6/2009 | Padget et al. | |
| 7,608,083 B2 | 10/2009 | Lee et al. | |
| 7,708,756 B2 | 5/2010 | Nobis et al. | |
| 7,736,254 B2 | 6/2010 | Schena | |
| 7,862,554 B2 | 1/2011 | Hegeman et al. | |
| 7,947,035 B2 | 5/2011 | Miyamoto et al. | |
| 8,029,531 B2 | 10/2011 | Lee et al. | |
| 8,057,487 B2 | 11/2011 | Chu et al. | |
| 8,105,319 B2 | 1/2012 | Doyle et al. | |
| 8,105,350 B2 | 1/2012 | Lee et al. | |
| 8,365,633 B2 | 2/2013 | Simaan et al. | |
| 8,398,587 B2 | 3/2013 | Dewaele et al. | |
| 8,425,408 B2 | 4/2013 | Boulais et al. | |
| 8,465,475 B2 | 6/2013 | Isbell | |
| 8,528,440 B2 | 9/2013 | Morley et al. | |
| 8,540,748 B2 | 9/2013 | Murphy et al. | |
| 8,551,076 B2 | 10/2013 | Duval et al. | |
| 8,603,135 B2 | 12/2013 | Mueller | |
| 8,668,702 B2 | 3/2014 | Awtar et al. | |
| 8,672,206 B2 | 3/2014 | Aranyi et al. | |
| 8,764,448 B2 | 7/2014 | Yang et al. | |
| 8,777,898 B2 | 7/2014 | Suon et al. | |
| 8,870,867 B2 | 10/2014 | Walberg et al. | |
| 8,881,616 B2 | 11/2014 | Dize et al. | |
| 8,968,355 B2 | 3/2015 | Malkowski et al. | |
| 8,992,422 B2 | 3/2015 | Spivey et al. | |
| 9,050,121 B2 | 6/2015 | Doyle | |
| 9,060,796 B2 | 6/2015 | Seo | |
| 9,161,771 B2 | 10/2015 | Steger | |
| 9,220,398 B2 | 12/2015 | Woodley et al. | |
| 9,532,839 B2 | 1/2017 | Seo | |
| 9,575,504 B2 | 2/2017 | Dize et al. | |
| 9,579,013 B2 | 2/2017 | Dewaele et al. | |
| 9,629,682 B2 | 4/2017 | Wallace et al. | |
| 9,629,689 B2 | 4/2017 | Bowles et al. | |
| 9,649,096 B2 | 5/2017 | Sholev | |
| 9,675,370 B2 | 6/2017 | Awtar et al. | |
| 9,695,916 B2 | 7/2017 | Lee | |
| 9,696,700 B2 | 7/2017 | Beira et al. | |
| 9,770,300 B2 | 9/2017 | Kwon et al. | |
| 9,814,451 B2 | 11/2017 | Sharma et al. | |
| 9,869,339 B2 | 1/2018 | Zimmerman et al. | |
| 9,889,874 B1 | 2/2018 | Clause | |
| 9,955,988 B2 | 5/2018 | Stefanchik et al. | |
| 10,005,181 B2 | 6/2018 | Hasegawa et al. | |
| 10,085,624 B2 | 10/2018 | Isoda et al. | |
| 10,198,086 B2 | 2/2019 | Parazynski et al. | |
| 10,271,913 B2 | 4/2019 | Yoshii et al. | |
| 10,325,072 B2 | 6/2019 | Beira et al. | |
| 10,363,055 B2 | 7/2019 | Beira et al. | |
| 10,405,936 B2 | 9/2019 | Awtar et al. | |
| 10,449,010 B2 | 10/2019 | Dewaele et al. | |
| 10,660,719 B2 | 5/2020 | Mathelin et al. | |
| 10,660,721 B2 | 5/2020 | Bonny et al. | |
| 10,664,002 B2 | 5/2020 | Parazynsk et al. | |
| 10,695,141 B2 | 6/2020 | Lee | |
| 10,709,467 B2 | 7/2020 | Lee et al. | |
| 10,722,315 B2 | 7/2020 | Lee et al. | |
| 10,753,439 B2 | 8/2020 | Awtar | |
| 10,959,797 B2 | 3/2021 | Licht et al. | |
| 11,344,381 B2 | 5/2022 | Lee et al. | |
| 11,490,980 B2 | 11/2022 | Lee et al. | |
| 11,510,746 B2 | 11/2022 | Lee et al. | |
| 2001/0031983 A1 | 10/2001 | Brock et al. | |
| 2003/0036748 A1 | 2/2003 | Cooper et al. | |
| 2003/0135203 A1 | 7/2003 | Wang et al. | |
| 2003/0135204 A1 | 7/2003 | Lee et al. | |
| 2003/0153902 A1 | 8/2003 | Doyle et al. | |
| 2003/0176880 A1 * | 9/2003 | Long | A61B 10/04 606/205 |
| 2003/0176948 A1 | 9/2003 | Green | |
| 2004/0068274 A1 * | 4/2004 | Hooven | A61B 18/1442 606/151 |
| 2004/0138700 A1 | 7/2004 | Cooper et al. | |
| 2004/0236316 A1 | 11/2004 | Danitz et al. | |
| 2004/0253079 A1 | 12/2004 | Sanchez | |
| 2005/0004431 A1 | 1/2005 | Kogasaka et al. | |
| 2005/0038469 A1 | 2/2005 | Lang | |
| 2005/0090811 A1 | 4/2005 | Doyle et al. | |
| 2005/0107667 A1 | 5/2005 | Danitz et al. | |
| 2005/0119692 A1 * | 6/2005 | Szabo | A61B 17/2841 606/1 |

(56) References Cited

U.S. PATENT DOCUMENTS

| | | |
|---|---|---|
| 2006/0111210 A1 | 5/2006 | Hinman |
| 2006/0111616 A1 | 5/2006 | Danitz |
| 2006/0156848 A1 | 7/2006 | Gosselin et al. |
| 2006/0190034 A1* | 8/2006 | Nishizawa ......... A61B 17/2909 606/205 |
| 2006/0199999 A1 | 9/2006 | Ikeda et al. |
| 2006/0259073 A1 | 11/2006 | Miyamoto et al. |
| 2006/0282063 A1 | 12/2006 | Gotani |
| 2007/0021738 A1 | 1/2007 | Hasser et al. |
| 2007/0022562 A1 | 2/2007 | Hampton |
| 2007/0072466 A1 | 3/2007 | Miyamoto et al. |
| 2007/0078565 A1 | 4/2007 | Ghodoussi et al. |
| 2007/0093790 A1 | 4/2007 | Downey et al. |
| 2008/0004493 A1 | 1/2008 | Schiemann |
| 2008/0039256 A1 | 2/2008 | Jinno et al. |
| 2008/0065098 A1 | 3/2008 | Larkin |
| 2008/0177285 A1 | 7/2008 | Brock et al. |
| 2008/0193260 A1 | 8/2008 | Yokokohji et al. |
| 2008/0221591 A1 | 9/2008 | Farritor et al. |
| 2008/0243176 A1 | 10/2008 | Weitzner et al. |
| 2009/0118044 A1 | 5/2009 | Kuo et al. |
| 2009/0171147 A1 | 7/2009 | Lee et al. |
| 2009/0192511 A1 | 7/2009 | Haffenreffer |
| 2010/0004606 A1 | 1/2010 | Hansen et al. |
| 2010/0016853 A1 | 1/2010 | Burbank |
| 2010/0030018 A1 | 2/2010 | Fortier et al. |
| 2010/0056863 A1 | 3/2010 | Dejima et al. |
| 2010/0111645 A1 | 5/2010 | Al-Mouhamed et al. |
| 2010/0234831 A1 | 9/2010 | Hinman et al. |
| 2010/0249497 A1 | 9/2010 | Peine et al. |
| 2011/0024145 A1 | 2/2011 | Click et al. |
| 2011/0093005 A1* | 4/2011 | Strokosz ............ A61B 17/2909 606/205 |
| 2011/0112517 A1 | 5/2011 | Peine et al. |
| 2011/0118707 A1 | 5/2011 | Burbank |
| 2011/0152881 A1 | 6/2011 | Conner et al. |
| 2011/0152922 A1 | 6/2011 | Jeong |
| 2011/0178531 A1 | 7/2011 | Caputo et al. |
| 2011/0319911 A1 | 12/2011 | Conner et al. |
| 2012/0041450 A1* | 2/2012 | Awtar ................ A61B 17/2909 606/1 |
| 2012/0083799 A1 | 4/2012 | Chen et al. |
| 2012/0095298 A1 | 4/2012 | Stefanchik et al. |
| 2012/0118097 A1 | 5/2012 | Ilch |
| 2012/0152055 A1 | 6/2012 | Lechuga Priego |
| 2012/0186383 A1 | 7/2012 | Schvalb et al. |
| 2012/0271283 A1 | 10/2012 | Doyle |
| 2012/0277762 A1 | 11/2012 | Lathrop et al. |
| 2013/0012958 A1 | 1/2013 | Marczyk et al. |
| 2013/0023868 A1 | 1/2013 | Worrell et al. |
| 2013/0066334 A1 | 3/2013 | Schoepp |
| 2013/0172860 A1 | 7/2013 | Szewczyk et al. |
| 2013/0239734 A1 | 9/2013 | Hinman |
| 2014/0135762 A1* | 5/2014 | Masuda ............ A61B 18/1445 606/51 |
| 2014/0135805 A1 | 5/2014 | Windgassen et al. |
| 2014/0246471 A1 | 9/2014 | Jaworek et al. |
| 2014/0331798 A1 | 11/2014 | Shim et al. |
| 2014/0371532 A1 | 12/2014 | Trovato |
| 2015/0021068 A1 | 1/2015 | Bernhardt et al. |
| 2015/0053455 A1 | 2/2015 | Hagi |
| 2015/0164601 A1 | 6/2015 | Sholev |
| 2015/0209059 A1 | 7/2015 | Trees et al. |
| 2015/0230697 A1 | 8/2015 | Phee et al. |
| 2016/0135830 A1 | 5/2016 | Volkmer et al. |
| 2017/0245954 A1 | 8/2017 | Beira |
| 2017/0360522 A1 | 12/2017 | Beira et al. |
| 2018/0000318 A9 | 1/2018 | Rogers et al. |
| 2018/0049842 A1 | 2/2018 | Bowles et al. |
| 2018/0125519 A1 | 5/2018 | Beira et al. |
| 2018/0125592 A1 | 5/2018 | Beira |
| 2018/0221045 A1 | 8/2018 | Zimmerman et al. |
| 2018/0289384 A1 | 10/2018 | Bowles et al. |
| 2018/0353252 A1 | 12/2018 | Chassot et al. |
| 2019/0133698 A1 | 5/2019 | Beira et al. |
| 2019/0239972 A1 | 8/2019 | Chassot et al. |
| 2019/0336230 A1 | 11/2019 | Awater et al. |
| 2020/0121406 A1 | 4/2020 | Lee |
| 2020/0146766 A1 | 5/2020 | Lee |
| 2020/0229835 A1 | 7/2020 | Lee et al. |
| 2021/0212785 A1 | 7/2021 | Licht et al. |

FOREIGN PATENT DOCUMENTS

| | | |
|---|---|---|
| CN | 103505265 A | 1/2014 |
| CN | 104889974 A | 9/2015 |
| EP | 2810745 A1 | 12/2014 |
| EP | 2923646 A2 | 9/2015 |
| EP | 2923662 A2 | 9/2015 |
| EP | 3232951 A2 | 6/2016 |
| EP | 3232952 A1 | 6/2016 |
| EP | 3232973 A1 | 6/2016 |
| EP | 3232974 A2 | 6/2016 |
| EP | 3232977 A1 | 6/2016 |
| EP | 3340897 A1 | 3/2017 |
| GB | 973587 A | 10/1964 |
| GB | 2513326 A | 10/2014 |
| JP | 3-292879 A | 12/1991 |
| JP | H06-262549 A | 9/1994 |
| JP | 8-84702 A | 4/1996 |
| JP | H09-96146 A | 4/1997 |
| JP | 2002102248 A | 4/2002 |
| JP | 2003061969 A | 3/2003 |
| JP | 2007130485 A | 5/2007 |
| JP | 2008531222 A | 8/2008 |
| JP | 2009127289 A | 6/2009 |
| JP | 2009136684 | 6/2009 |
| JP | 2012513823 A | 6/2012 |
| JP | 2013507196 A | 3/2013 |
| JP | 2013070861 A | 4/2013 |
| JP | 6220085 B2 | 10/2017 |
| WO | WO2006/036067 A2 | 4/2006 |
| WO | WO2007/137304 A2 | 11/2007 |
| WO | WO2007/146894 A2 | 12/2007 |
| WO | WO2008/020964 A2 | 2/2008 |
| WO | WO2010/104755 A1 | 9/2010 |
| WO | WO2013/027203 A1 | 2/2013 |
| WO | WO2014/033717 A2 | 3/2014 |
| WO | WO2015/125140 A1 | 8/2015 |
| WO | WO2016/063213 A1 | 4/2016 |
| WO | WO2016/161449 A1 | 10/2016 |
| WO | WO2017/062516 A1 | 4/2017 |
| WO | WO2017/062529 A1 | 4/2017 |
| WO | WO2019/155383 A1 | 8/2019 |

OTHER PUBLICATIONS

Clement et al.; Design of a Snake-Like Manipulator; Robotics and Autonomous Systems; 6(3); pp. 265-282; Jul. 1990.

Do et al.; Adaptive control of position compensation for cable-conduit mechanisms used in flexible surgical robots; Proceedings of the 11th International Conference on Informatics in Control, Automation and Robotics (ICINCO-2014); IEEE: pp. 110-117; Sep. 1. 2014.

Ikuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.

Jug et al.; The JPL Serpentine Robot: a 12 DOF System for Inspection (Conference Paper); Proceedings—IEEE International Conference on Robotics and Automation 3: 5 pgs.; Jun. 1995.

Peirs et al.; A flexible distal tip with two degrees of freedom for enhanced dexterity in endoscopic robot surgery: MME'02; The 13th Micromechanics Europe Workshop: Sinaia, Romania; pp. 271-274: Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Walker et al.; Novel 'Elephant's Trunk' Robot; IEEE/ASME International Conference on Advanced Intelligent Mechatronics, AIM; Piscataway, NJ, United States; pp. 410-415; Sep. 19-23, 1999.

(56) References Cited

OTHER PUBLICATIONS

Wikipedia; Constant Velocity Joint; 6 pgs .; retrieved from the internet (https://en.wikipedia.org/wiki/Constant-velocity_joint) on Dec. 22, 2016.
Wikipedia; Six-bar linkage; 2 pgs; retrieved from the internet (https://en.wikipedia.org/w/index.php?title=Six-bar_linkage&oldid=670945266) on Apr. 26, 2019.

\* cited by examiner

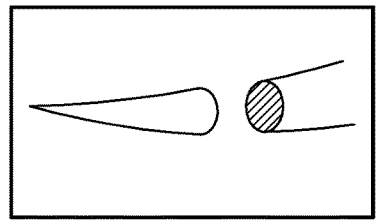 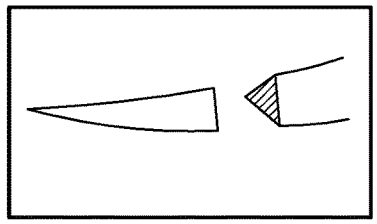 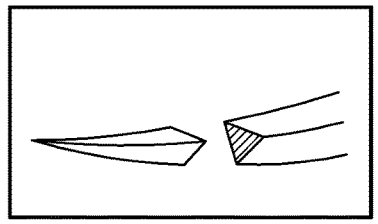
  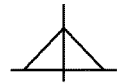  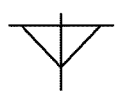 
| TIP | BODY | TIP | BODY | TIP | BODY |
|---|---|---|---|---|---|
| ROUND BODIED | | CURVED CUTTING | | REVERSE CUTTING | |
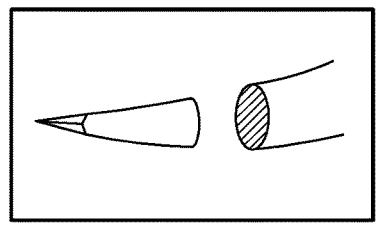 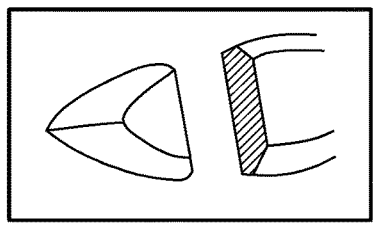 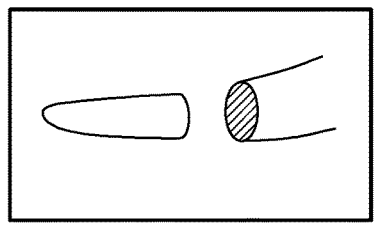
  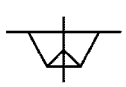  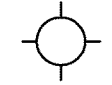 
| TIP | BODY | TIP | BODY | TIP | BODY |
|---|---|---|---|---|---|
| TAPERCUT | | MICRO-POINT SPATULA | | BLUNT TAPER POINT | |
FIG. 4

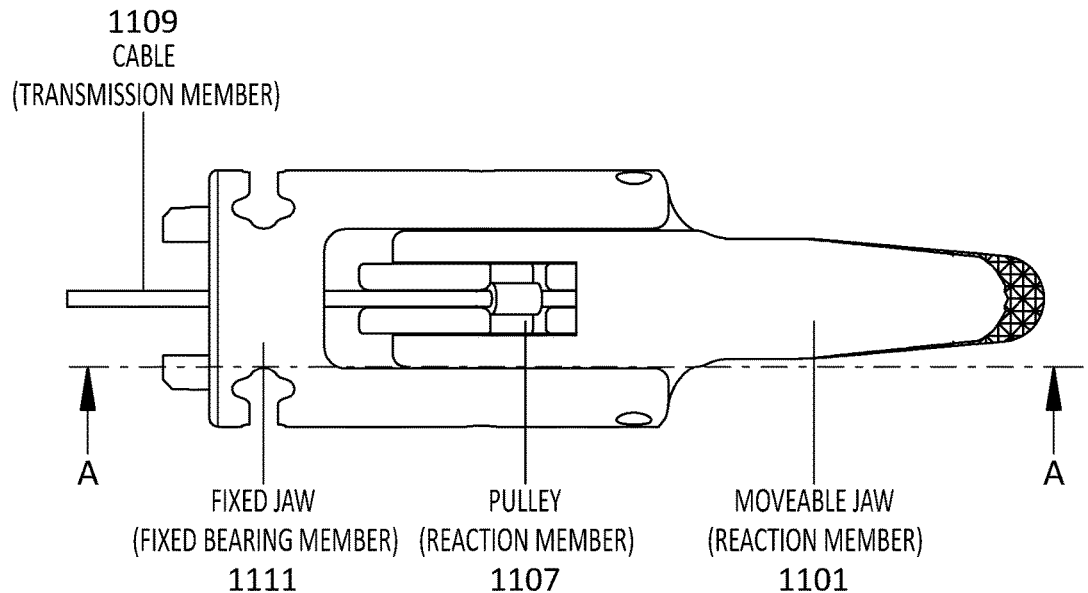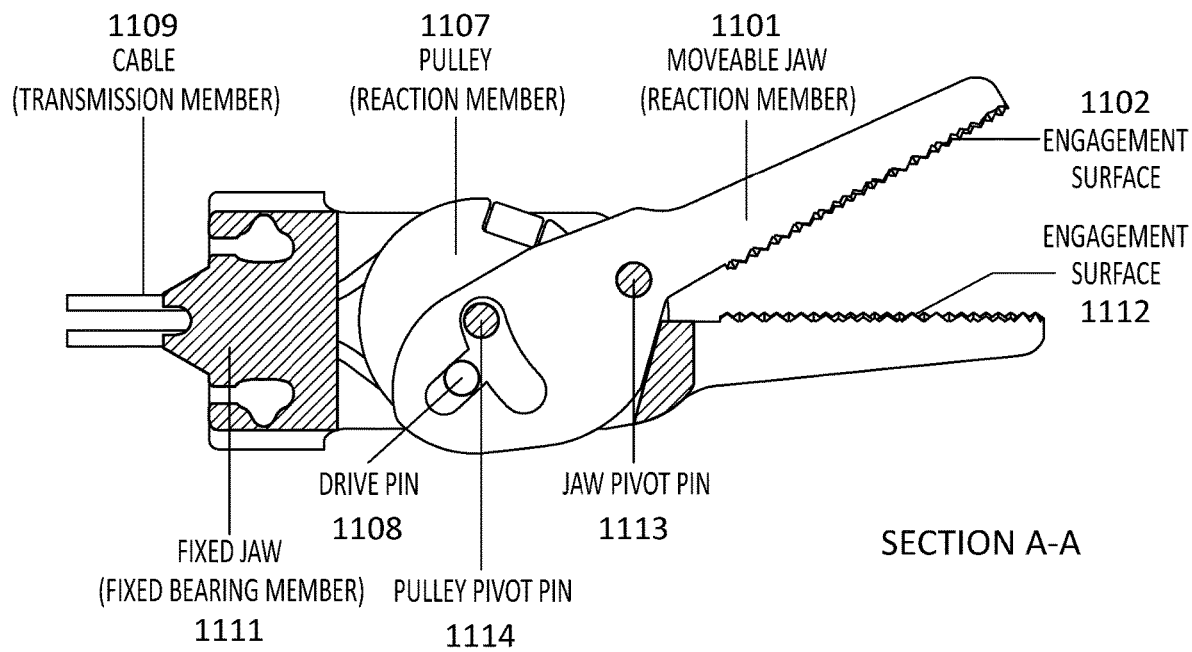
FIG. 12A

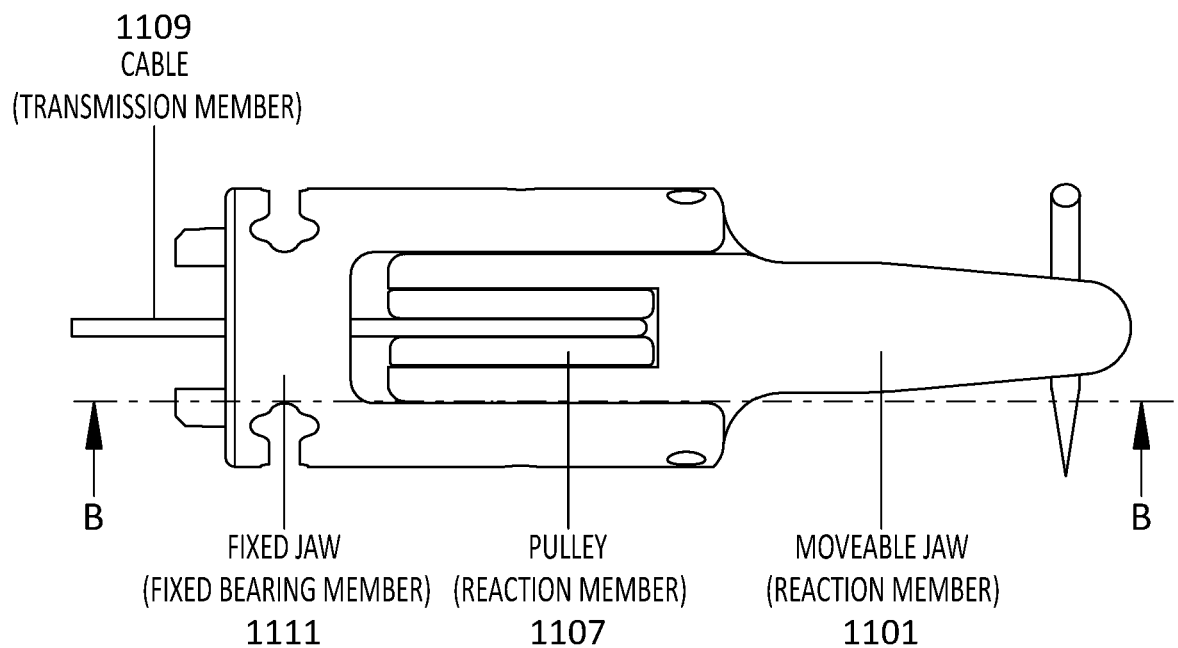
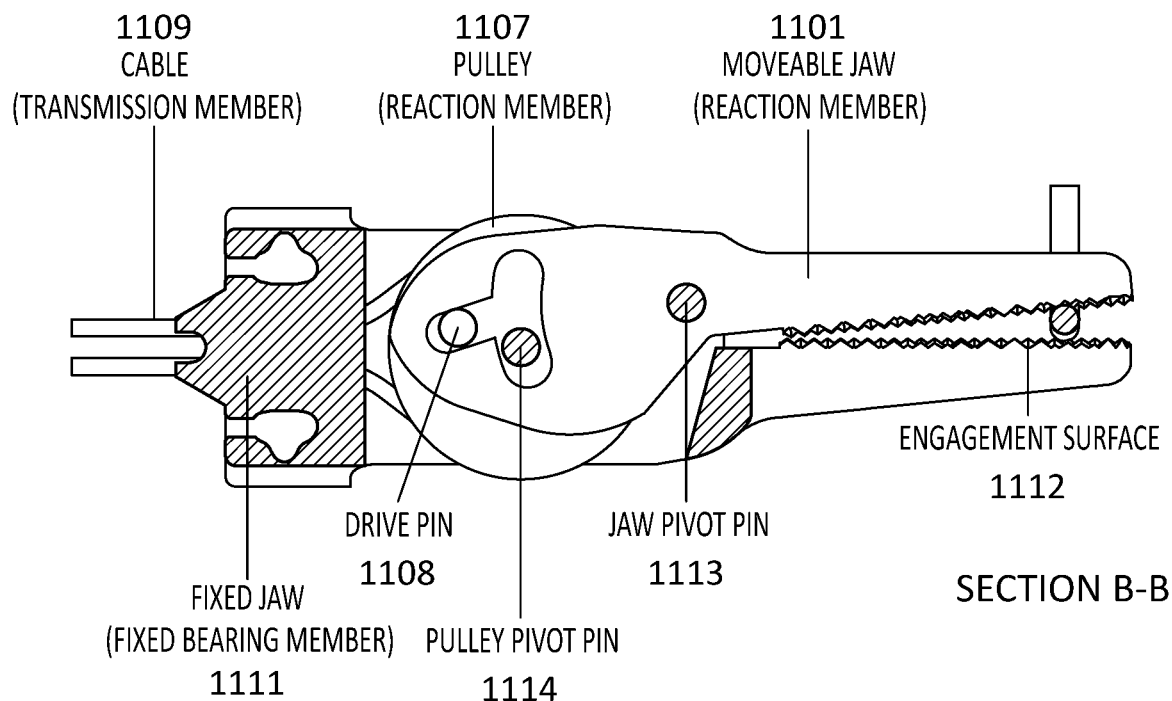
FIG. 12B

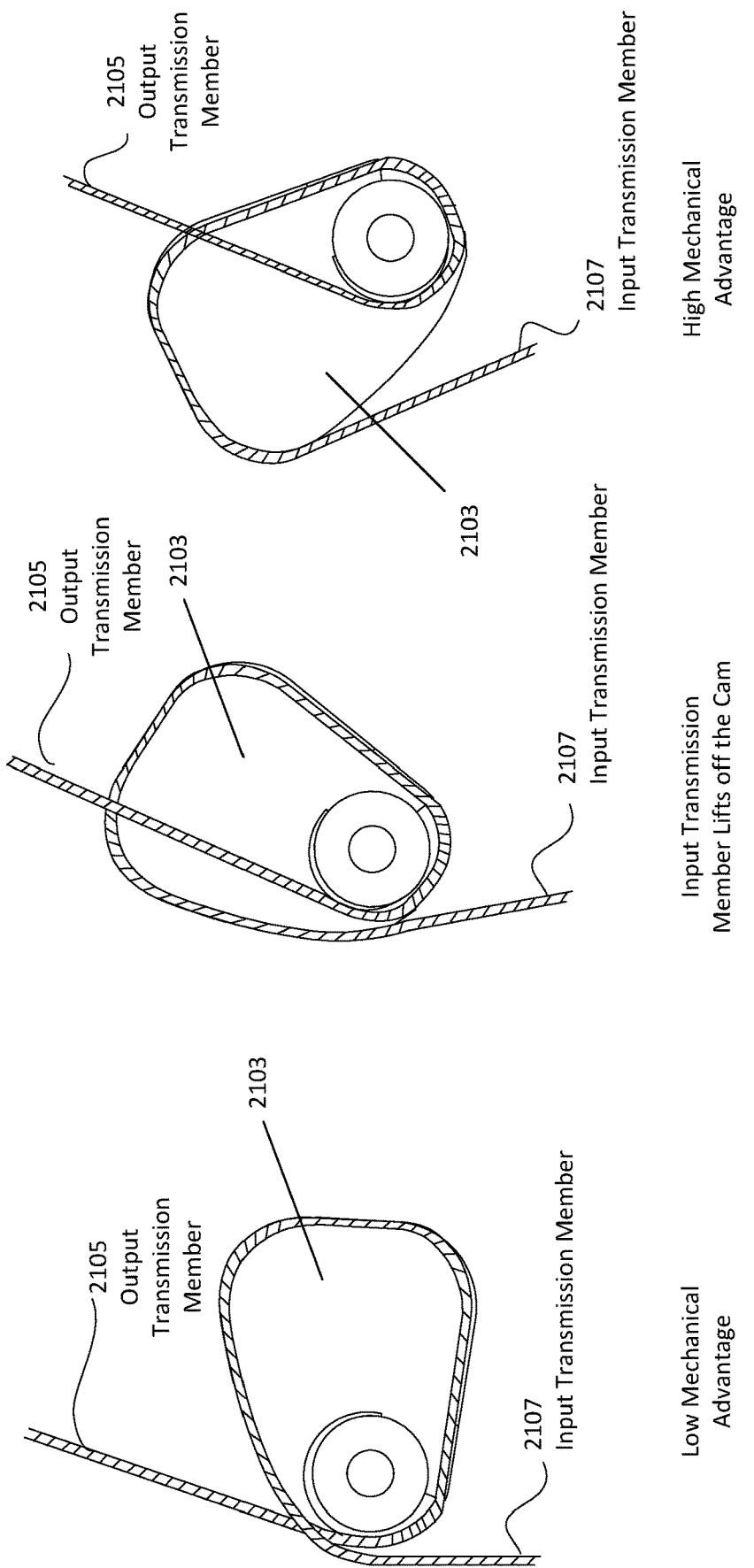

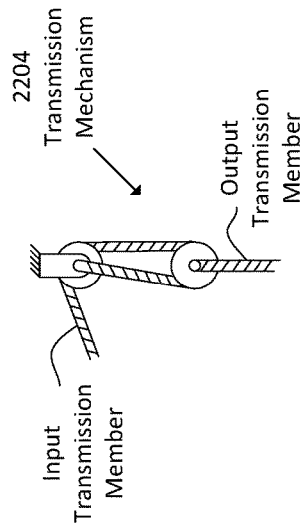
FIG. 22A
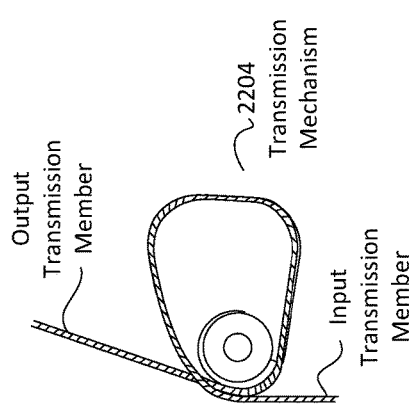
FIG. 22B
FIG. 22C
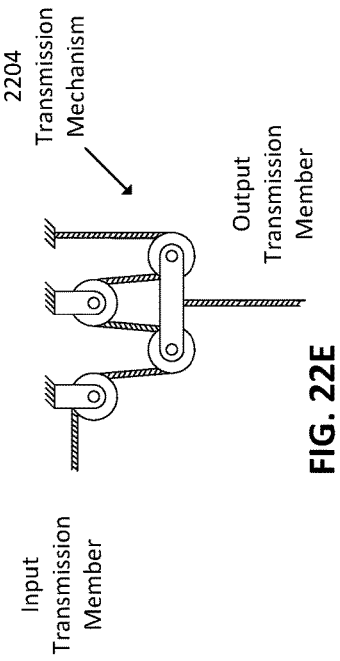
FIG. 22D
FIG. 22E
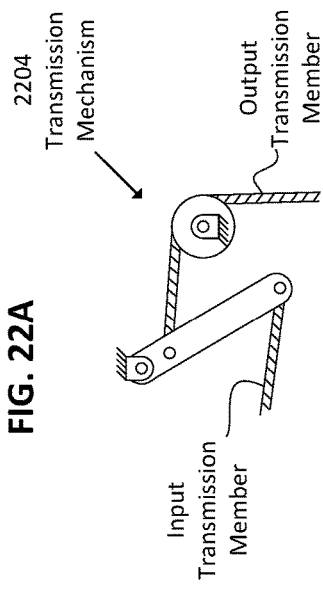
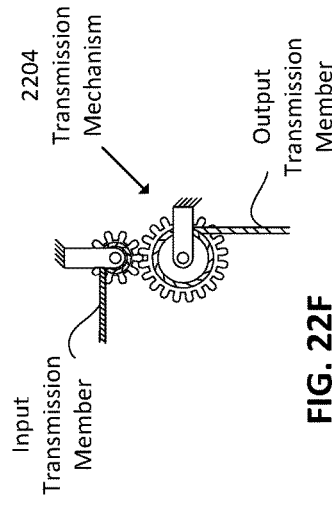
FIG. 22F
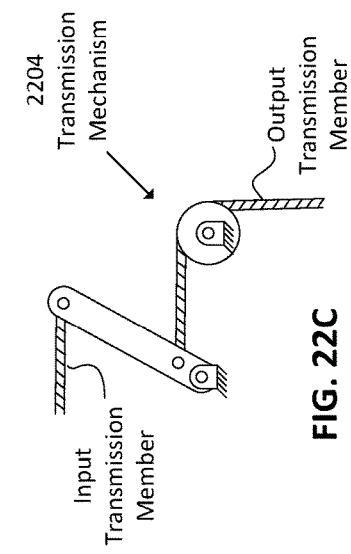

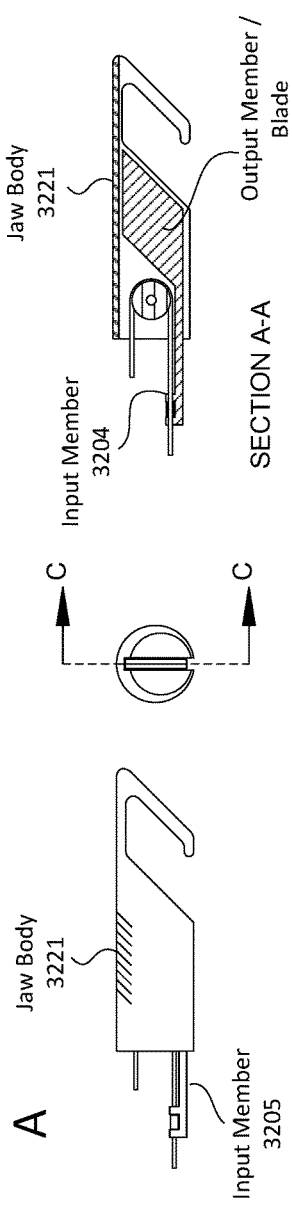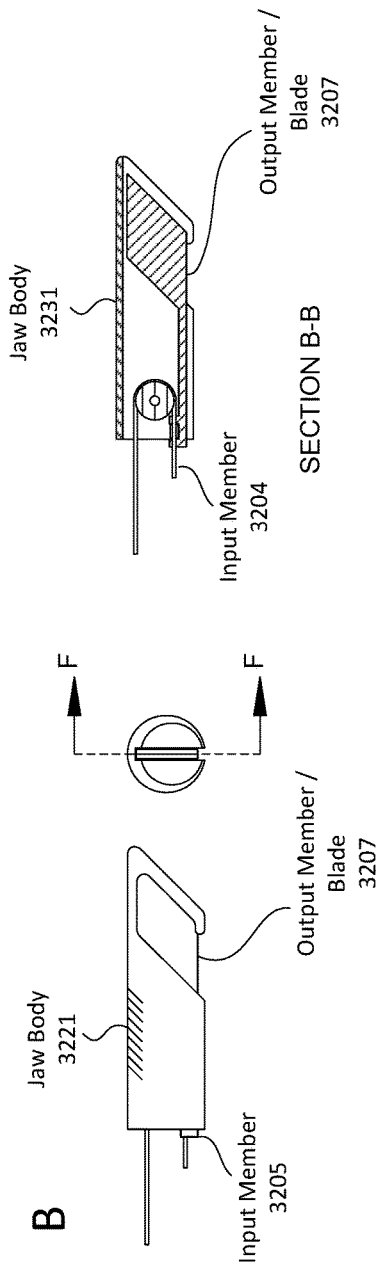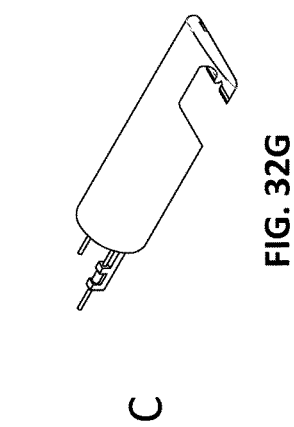

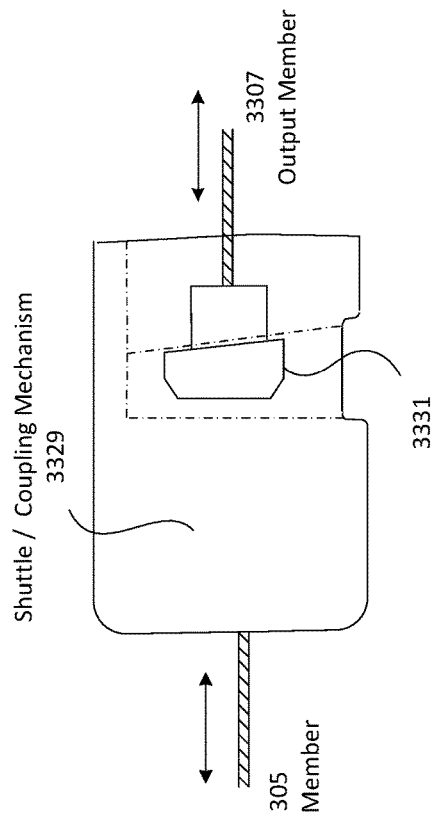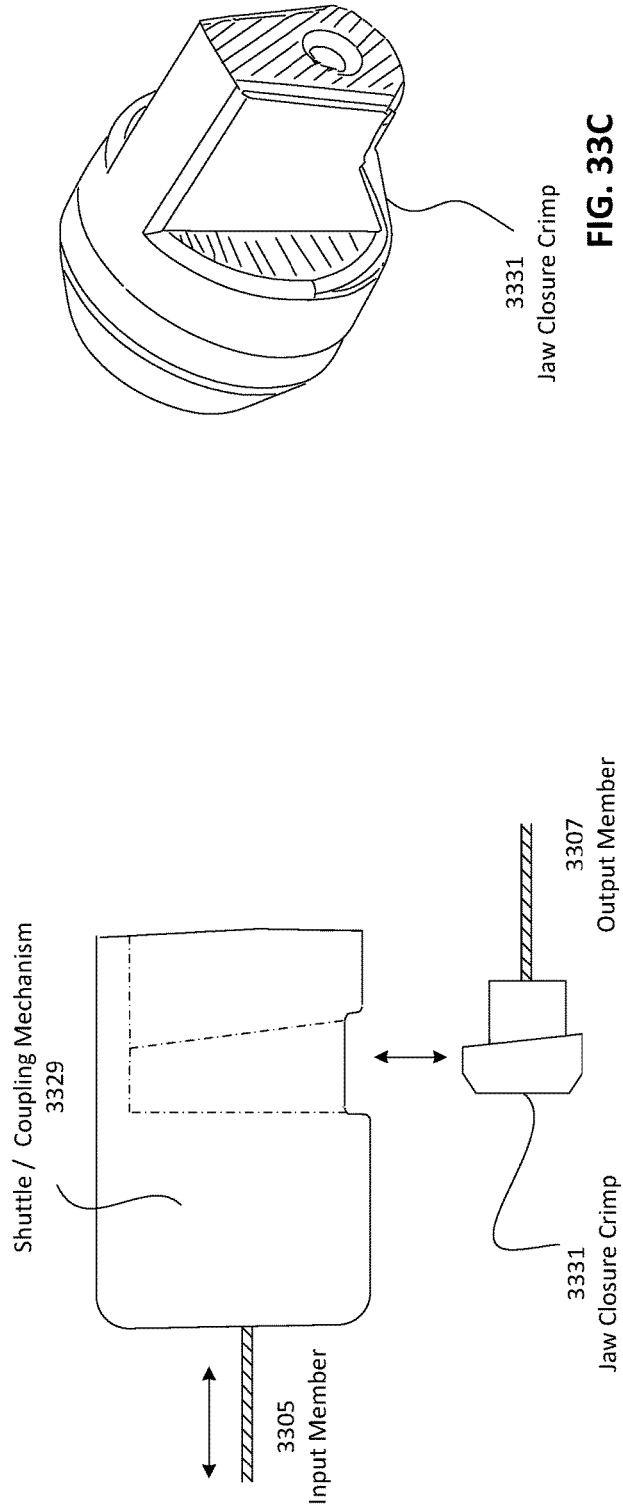

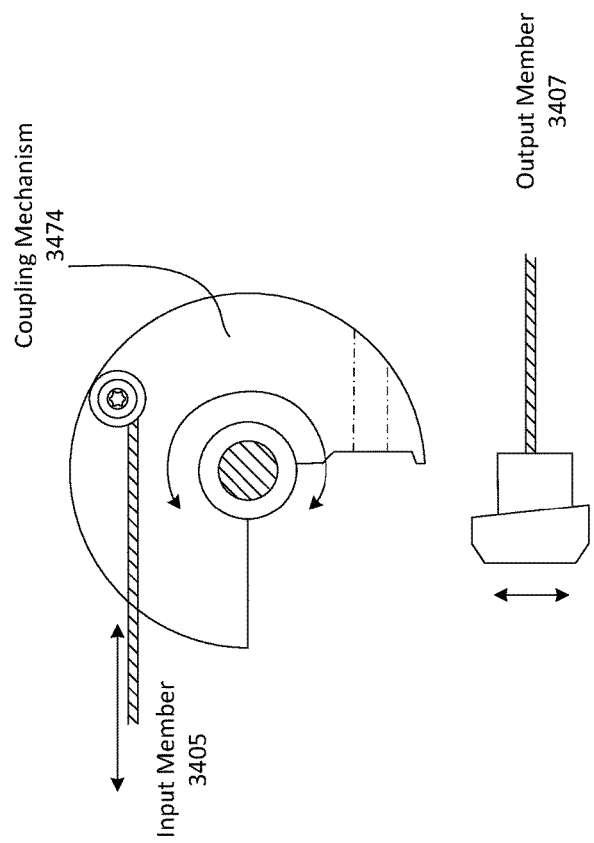
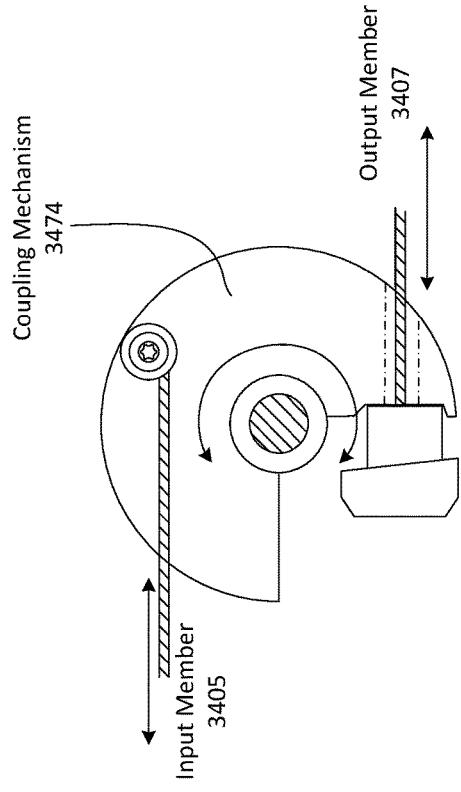

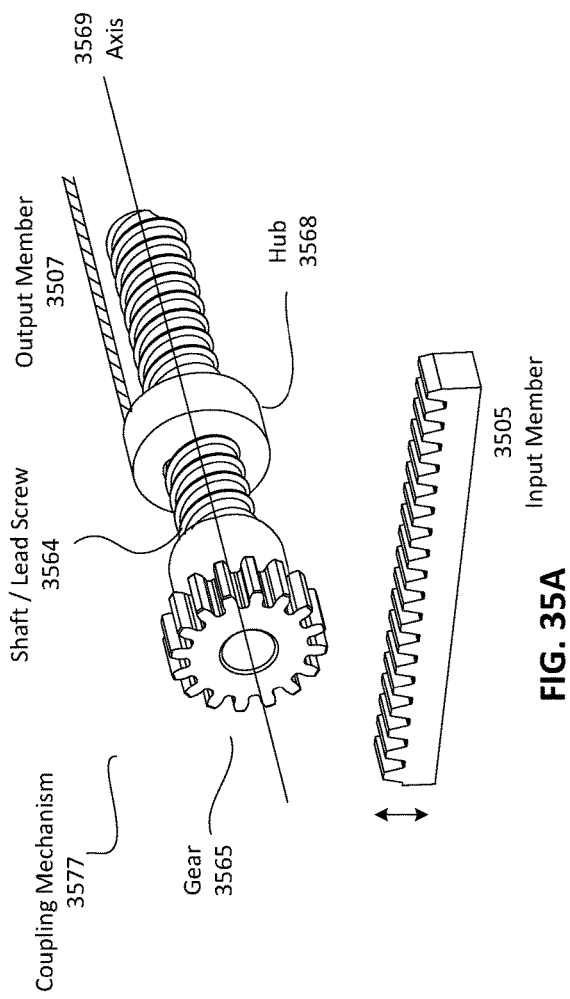
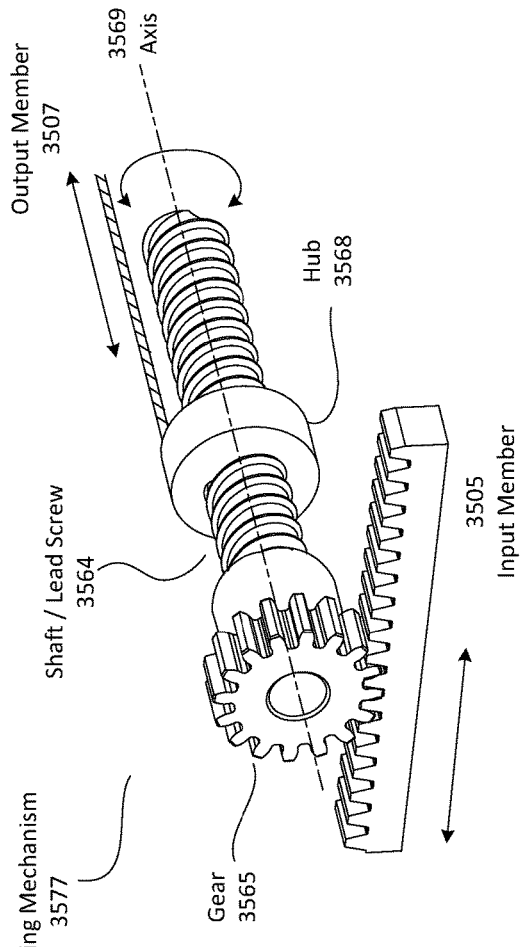
FIG. 35A
FIG. 35B

END-EFFECTOR JAW CLOSURE TRANSMISSION SYSTEMS FOR REMOTE ACCESS TOOLS

CROSS REFERENCE TO RELATED APPLICATIONS

This patent application claims priority as a continuation-in-part to U.S. patent application Ser. No. 15/946,612, titled "END-EFFECTOR JAW CLOSURE TRANSMISSION SYSTEMS FOR REMOTE ACCESS TOOLS," filed on Apr. 5, 2018, which is a continuation of International Patent Application No. PCT/US2016/055606, titled "END-EFFECTOR JAW CLOSURE TRANSMISSION SYSTEMS FOR REMOTE ACCESS TOOLS, filed on Oct. 5, 2016, now International Publication No. WO 2017/062529, which claims priority to U.S. Provisional Patent Application No. 62/237,476, titled "END-EFFECTOR JAW CLOSURE TRANSMISSION SYSTEMS FOR REMOTE ACCESS TOOLS," filed on Oct. 5, 2015; and to U.S. Provisional Patent Application No. 62/237,483, titled "ARTICULATING JOINT AND SUPPORTING MEMBER THEREOF," filed on Oct. 5, 2015, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are transmission systems that are used for remote access instruments, for example minimally invasive surgical tools. In particular the apparatus provides a transmission system design that utilizes the transmission member as an energy storing device, over a certain portion of input stroke, to achieve a specific desired performance of the surgical tool. In general, the transmission member may be referred to as a jaw closure transmission member, or as a jaw closure transmission cable, or as a transmission cable, or as a cable or the like.

BACKGROUND

Typically, in laparoscopic, endoscopic, or other minimally invasive surgical procedures, a small incision or puncture is made in a patient's body. A cannula is then inserted into a body cavity through the incision, which provides a passageway for inserting various surgical devices such as scissors, dissectors, retractors or similar instruments. To facilitate operability through the cannula, instruments adapted for laparoscopic surgery typically embody a relatively narrow shaft supporting an end-effector (EE) at its distal end and a lever or handle at its proximal end. Arranging the shaft of such an instrument through the cannula allows a surgeon to manipulate the proximal handle from outside the body to cause the distal end-effector to carry out a surgical procedure at a remote internal surgical site. In most embodiments, the handle and tool shaft can be directly connected, and roll rotation of the entire handle may drive rotation of the entire tool shaft and end-effector. Some alternative laparoscopic tools, such as, for example, U.S. Pat. No. 8,668,702 includes a handle that is not directly connected to the tool shaft but connected via an input joint (e.g., comprising a pair of transmission strips) which still allows for roll rotation of the tool shaft and end-effector by way of handle rotation. In general, a handle body may be referred to as a handle reference, or as a palm grip, handle shell, or the like.

It would be beneficial to provide devices, an in particular medical devices, that control an input stroke so that actuation of an output (e.g., jaw) is reliably transmitted through a transmission cable to control the forces exerted by the output. These devices and methods of operating them should be robust and inexpensive to manufacture. Described herein are methods and apparatuses (e.g., devices, systems, etc.) that may provide these benefits.

SUMMARY OF THE DISCLOSURE

A laparoscopic or endoscopic instrument may provide a surgeon with the ability to transfer high force loads from the proximal end of the tool to the distal end. These forces are transferred through the instrument through an input sub-system, output sub-system, and transmission member sub-system, each sub-system can consist of a transmission mechanism. The input sub-system (e.g. an input member, or a handle assembly) may consists of a handle body, a handle lever as an input, and an output (for example, a shuttle coupled to the handle body via a one Degree of Freedom (DoF) slider joint). As a user actuates the handle lever, this motion is transferred to the shuttle via the input member, and the amount that the shuttle displaces is based on the input member's mechanical advantage or transmission ratio. The terms transmission ratio and mechanical advantage are both used in this document since the transmission ratio and mechanical advantage are, in general, simply the inverse of each other. When emphasizing force, the attribute mechanical advantage is used, and when emphasizing displacement, the attribute transmission ratio is used. In general, the mechanical advantage of the input member can vary over the input stroke. Similarly, the output sub-system (e.g. output mechanism, end-effector jaw assembly, etc.) can have a varying mechanical advantage or transmission ratio over the output stroke. For a mechanical surgical instrument which requires a high force output while not compromising on output displacement (i.e. output stroke), this varying mechanical advantage of both the input member and the output mechanism will have a certain desirable profile. The mechanical advantage during the initial portion of the input stroke can be low because no force build up is required initially; however the mechanical advantage at the end of the input stroke needs to be high to allow a reasonable input force to be amplified into a large output force. The transmission members used in the prior art are generally stiff in the direction of transmission. However, this transmission member does not have to be rigid. In the transmission sub-systems described herein, the transmission member itself is designed to have a finite stiffness in the transmission direction so that it acts as an energy storage member during certain portions of the input stroke of the device, and very low stiffness in the bending direction to allow articulation of the end-effector jaw assembly. This offers a unique performance of the device and has many benefits over rigid or highly stiff transmission members.

Described herein are jaw closure transmission systems that provide enhanced closure security and feel. These closure transmissions may be part of any appropriate apparatus, including medical devices (e.g., minimally invasive surgical tools), or any other application in which it is beneficial or desirable to have a jaw closure mechanism that may securely grip and provide feedback to the user on grip strength, as will be described herein.

In general, the jaw closure transmission systems described herein may include rigid and compliant transmission elements, including an input (e.g., a jaw actuation input), an output (e.g., jaw mechanism), a transmission cable having a finite stiffness in a transmission direction, and a rigid or flexible transmission guiding element, wherein the transmission element stores energy during closure transmission to achieve unique and desirable functionality. The terms transmission elements and transmission members are used interchangeable through this disclosure.

The jaw closure transmission systems described herein may include three (or more) sub-systems that are serially connected that take an overall input, in the form of handle lever displacement and force from the user, and produce an overall output that presents as moving jaw displacement and associated clamp load. In general, a moving jaw may be referred as a movable jaw, or as an end-effector moving jaw, or as an EE moving jaw, or the like. The three sub-systems are as follows: (a) input sub-system: handle assembly (or handle mechanism, or input member); (b) output sub-system: jaw assembly (or end-effector jaw assembly, or end-effector assembly, or output mechanism, or jaw mechanism); (c) transmission sub-system (e.g., transmission member, e.g., cable, and transmission guide, e.g., flexible conduit). The input sub-system may include the input in a handle assembly, which comprises a handle body or shell that serves as the local reference or ground, and a handle lever configured to receive user input in the form of closing or displacing the handle lever relative to the handle body. In general, the full closure displacement of the handle lever with respect to the handle body is referred to as the input stroke. At full closure, i.e., at the end of an input stroke, the handle lever reaches a hard-stop relative to the handle body. At this hard stop, there may be a single locking or latching feature that keeps the handle lever latched closed relative to the handle body. An unlatching/unlocking feature (e.g., a releasable lock) unlocks the handle lever and allows it to open again with respect to the handle body. Alternatively, there be a multi-stage ratchet that allows the handle level to be locked at different locations along the input stroke.

The handle assembly may also include a handle output (handle mechanism output) that connects to the transmission cable. The handle output may be a shuttle, a push rod, a pull rod, etc. The output typically interfaces with the transmission member and in response to an actuation of the handle lever provides an actuation motion to the proximal end of the transmission member.

In general, the handle mechanism (which is the transmission mechanism of the handle assembly) is configured as a mechanical linkage system that translates the motion of the handle lever relative to the handle body to a corresponding actuation motion of the handle shuttle relative to the handle body. The handle mechanism provides a transmission ratio and mechanical advantage between the handle lever and the handle shuttle so as to produce the appropriate actuation displacement and force at the proximal end of the transmission member (e.g., appropriate cable tension and cable displacement) via the handle shuttle during the overall stroke of the handle lever (i.e., input stroke). This optimization may be based on the structure and functionality of the overall jaw closure transmission system including the input sub-system, transmission sub-system, and output sub-system, and in some variations may not be due to just the input sub-system.

The handle mechanism may be designed such that instead of providing a constant mechanical advantage or transmission ratio, it produces a higher transmission ratio (i.e., lower mechanical advantage) in the first portion of the input stroke and a lower transmission ratio (i.e., higher mechanical advantage) in the second portion of the input stroke.

The output sub-system typically includes an end-effector assembly or jaw assembly or end-effector jaw assembly, or output mechanism, and may include the following elements: an end-effector (e.g., jaw) base or end-effector fixed jaw that serves as the local reference or ground; an end-effector movable jaw coupled to the end-effector fixed jaw (e.g., pivotally coupled to the end-effector fixed jaw) such that it can open and close (i.e., displace) with respect the end-effector fixed jaw.

The full closure displacement of the moving jaw relative to the fixed jaw may be referred to as the output stroke. In the devices described herein, the output stroke is always completed prior to completion of the input stroke, and is generally completed around the transition between the first portion of the input stroke and the second portion of the input stroke (e.g., between about 30% and 70% of the full input stroke, e.g., between about 40% and 60% of the full input stroke, between about 40% and 70% of the full input stroke, between about 45% and 60% of the full input stroke, etc.).

In general, once the jaws have been closed either against themselves or against an object grasped in the jaws (e.g. a needle), the jaws of the jaw assembly are at a stop position, and will no longer close further (full output stroke), by the action of the handle assembly actuating the transmission cable. However, because the transmission cable has a finite stiffness (e.g., is somewhat compliant) in a transmission direction (i.e. along the length or axis of the cable itself), the handle assembly may continue to be actuated in the second part of the input stroke, and may stretch the transmission cable. This stretch may be felt by the user operating the handle (as resistance in the handle) and the force being applied to stretch the cable may be transmitted to the jaws as a holding force between the jaws.

Thus, a closure displacement of the handle lever relative to the handle body at the input sub-system of the closure transmission system may result in a closure displacement of the moving jaw relative to the fixed jaw to hold an object (such as a needle, suture, tissue, staple, clip, etc.) between the jaws.

A pulley coupled to the fixed jaw (e.g., pivotally coupled to the fixed jaw) may be configured to receive the actuation motion from the distal end of the transmission member. The jaw assembly may include a jaw mechanism, which may be a linkage, a cam (e.g., cam surface and pin), etc. The jaw mechanism (e.g., in some variations comprising a pulley, a drive pin, a cam surface on the moving jaw) may translate the actuation motion of the distal end of the transmission member to the jaw pulley rotation relative to the fixed jaw, which is further translated to a corresponding closure motion of the moving jaw relative to the fixed jaw.

In one example of the jaw mechanism, a drive pin is driven by the pulley and interfaces with a camming surface on the moving jaw, providing a camming action. In this example of the jaw mechanism, the distal end of the transmission member (i.e., cable) is wrapped around the pulley. To prevent a potential slippage between the cable and the pulley, there is a positive engagement feature between the cable and the pulley. This is accomplished via a member (e.g. cylindrical in shape) that is crimped (e.g. secured) onto the cable and sits in a cavity on the pulley. The jaw mechanism is designed to provide a mechanical advantage or transmission ration between the distal end of the transmission member and the moving jaw, so as to produce the appropriate output displacement and force at the moving jaw relative to the fixed jaw during the overall stroke of the moving jaw (i.e., output stroke). This optimization of mechanical advantage or transmission ratio may be based on the structure and functionality of the overall closure transmission system including the input sub-system, transmission sub-system, and output sub-system, and not just the output sub-system. Specifically, the jaw assembly (output mechanism) may be designed to provide a large mechanical advantage at the end of its stroke, to maximally amplify the force in the transmission member (i.e., tension in the jaw closure transmission cable) to a clamping force at the jaws. This implies that for a certain desired jaw clamping force, the transmission cable tension can be less, which has several advantages including less wear and frictional losses.

The transmission sub-system may include a transmission member to transmit the output action of the input sub-system (i.e., handle assembly) to the input of the output sub-system (i.e., jaw assembly) of the closure transmission system. More specifically, the transmission member may transmit the actuation motion of the handle shuttle of the handle assembly to a corresponding actuation motion of the jaw pulley of the jaw assembly. This transmission member may be a cable, braided rope, etc. that is capable of accommodating very tight bends as might be necessary when the closure transmission system is part of a remote access tool or device.

The transmission member may be highly compliant (i.e., flexible) in bending, twisting, and compression. This member is relatively stiffer in tension because it has to transmit force and displacement along this direction; but at the same time, it is not chosen or designed to be infinitely or effectively infinitely stiff. Rather, it is intentionally designed or chosen to have a finite stiffness instead of infinite stiffness (or finite compliance instead of zero compliance) so that it can also serve as an inline spring. Infinite stiffness corresponds to zero compliance and zero stiffness corresponds to infinite compliance. In general, nothing is infinitely stiff or infinitely compliant. Instead, stiffness and compliance may be assessed on a relative scale. For example, on some normalized scale a stiffness less than 10 is close to infinitely compliant and a stiffness greater than 1000 is closely to infinitely stiff. On such as scale, in any of the apparatuses described herein, the axial stiffness of the transmission member may have a stiffness greater than 100 (i.e. stiffness along a transmission direction) and bending stiffness of the transmission member may be less than 10.

Any of these apparatuses may include a transmission guide that serves as a conduit or channel (also, a reference) for the transmission member. The proximal portion of this transmission guide is connected to the input sub-system reference (i.e., handle body) and the distal portion of this transmission guide is connected to the output sub-system reference (i.e., end-effector fixed jaw). This guide may be completely rigid in all directions, such as a frame, or a shaft, or tube. Alternatively, this guide may be flexible in bending so that it can take an arbitrary, tortuous shape but still remain very stiff (ideally, close to infinitely stiffness) axially (i.e., along its bent/deformed central axis). Or, this guide may be highly flexible in bending (i.e. very low stiffness in bending) so that it can take an arbitrary, tortuous shape and have an intermediate stiffness (i.e., have some intentionally finite compliance) in the axial direction (i.e., along its bent/deformed central axis).

The connections between the ends of the guide and respective references of the input and output sub-systems maybe close to infinitely stiff in the transmission direction (i.e., an axial direction of the transmission cable) or may have some intentionally finite compliance (i.e., slightly lower stiffness than infinitely stiff values).

Collectively, the three coupled sub-systems may allow for the use of cables as the primary transmission member. Cables are highly flexible in bending and therefore can be incorporated within minimal access tools/devices that have an input articulation joint between the handle and the tool frame/shaft, and an output articulation joint between the tool frame/shaft and the end-effector. In such devices, the tool frame/shaft may also serve as a portion of the transmission guide, or as the entire transmission guide. In particular, the use of a cable transmission member enables a very tight bend at the output articulation joint, and also helps facilitate the miniaturization of the output articulating joint, and therefore the miniaturization of the end-effector as well at the distal end of the minimal access tool/device.

Furthermore, the choice of a cable as a transmission member and a flexible conduit as a transmission guide member facilitates a minimal access tool/device architecture where the handle assembly is not directly connected to a tool frame/shaft. Instead, in some variations of the devices described herein, the handle assembly "floats" with respect to the tool shaft/frame, and may be connected via an input articulating joint that has a virtual center of rotation proximal to the handle assembly. The system (apparatus) may include a flexible conduit as the transmission guide member to guide the transmission member (cable) from the handle assembly to the tool shaft/frame.

Furthermore, the choice of a cable as the jaw closure transmission member in an articulating minimal access tool/device may also ensure a relative decoupling between the jaw closure functionality of the device, and articulation functionality of the device. Since the transmission member itself does not have significant bending (i.e., articulation) stiffness, it does not significantly impact the articulation of the end-effector assembly (or jaw assembly) about the output articulation joint. Moreover, a large mechanical advantage in the jaw mechanism may result in a lower or limited tension in the transmission cable, which has several advantages listed below. Lower tension in the jaw closure transmission cable reduces jumpiness (lateral jerk due to lateral movement of the high tension jaw closure transmission cable within the output articulating joint) and S-bending (distortion of the output articulating joint due to buckling along its center axis) in the output articulating joint.

This overall jaw closure transmission system may enable jaw closure in two steps. During the first portion of the input stroke, as the handle lever moves from its fully open position to an approximately mid-way open position (typically about 30%-70% of the input stroke), the moving jaw goes from its fully open position to its fully closed position. In this state, the jaw mechanism has achieved its full output stroke and has reached a stop. This stop may be the result of jaw on jaw contact, or the two jaws holding a needle in between. In either case, the jaw mechanism has reached a static state while there is still input stroke remaining at the handle mechanism. From this point onwards, the remaining stroke of the handle mechanism goes into axially stretching the transmission member (i.e., cable) and/or axially compressing the transmission guide members. The intentional axial compliance selected in the transmission member and transmission guide member (discussed above) enables the user to continue to displace the handle lever through the remaining portion (i.e., the second portion) of the handle mechanism's overall input stroke. Thus, the second portion of the input stroke corresponds to stretching the cable and an associated increase in tension of the cable (based on the compliance of the cable). This gradually increasing cable tension continues to serve as the input force on the jaw mechanism and continues to get amplified by the mechanical advantage of this mechanism (even though the mechanism itself is static due to a hard-stop at the jaws). This means that the force between the jaws (with or without a needle in between) increasing as cable tension increases. Thus, while the first portion of the input stroke of the handle lever corresponds to an increasing displacement of the moving jaw from a fully-open position to a fully-closed position (i.e., total output stroke), which corresponds to a hard-stop at the jaws (with or without a needle); the second portion of the input stroke at the handle lever corresponds to a gradually increasing force between the jaws (with or without a needle) at the end-effector assembly. The embodiment may not only be a two-stage input stroke, but also may be a three-stage input stroke wherein the third stage (or portion) relates to a portion of the input stroke dedicated to facilitating handle lever locking. Within the third stage if the mechanical advantage is significantly higher than in the second stage, input at the input sub-assembly (handle lever) does not produce significant transmission member displacement of the transmission member due to higher mechanical advantage compared to the second stage, and therefore does not introduce much additional energy to the compliant transmission elements because the transmission elements are not stretched or compressed farther. The primary purpose of the third stage is to provide a single region where the handle mechanism locks into place. The presence of this third stage provides an opportunity to optimize handle mechanism design for locking, rather than for facilitating jaw mechanism closure or clamp load generation. Specifically, due to low displacement transmission member in the system the input force required throughout the third stage is not as heavily influenced by the mechanical spring-rate property for the compliant transmission members, but rather merely depends on frictional losses within the input sub-assembly. As a result of isolating the transmission sub-system and output sub-system kinematic behavior from the third stage, users of the device will experience a greater consistency of handle mechanism input force from the start of the input stroke in the third stage to the end of the input stroke in the third stage. Furthermore, the user input force in the third stage to lock the handle is significantly independent of needle location within the jaws of the output mechanism.

A compliant transmission member has several benefits for the user in the design, including the substantial reduction in sudden step changes in the force feedback felt by the surgeon at the handle lever as needle contact or jaw contact happens. The presence of the transmission member and/or transmission guide member compliance in the axial (i.e., transmission motion) direction makes this transition more gradual and therefore better in feel for the user, compared to a traditional device that has a highly rigid transmission member. This may also result in a reduced number of transmission elements since energy storage functionality is accomplished through the dual-purpose cable and flexible guide members, which play a role in actuation motion transmission as well as serve as energy storing elastic elements. During the second portion of the input stroke of the handle lever, the transmission sub-system efficiently stores energy by means of stretching the transmission cable. This energy storage is not passive, in the sense that the stretching of the cable corresponds to an increase in cable tension, which, when reflected through the mechanical advantage of the EE mechanism, produces an increased jaw force.

The force generated between the jaws may be a clamping force or may be a closure force, a grasping force, a holding force or a cutting force, etc.

In general, the jaw closure transmission systems described herein may be self-limiting and/or self-correcting and/or self-regulating systems for limiting the maximum force that is transmitted via the transmission member in spite of variations in the presence and location of a an object (e.g., needle) in the jaws. This may advantageously lower the loads of all members/components of the jaw closure transmission system. This may also or alternatively lead to less wear, longer life, less chances of failure, more durability etc., and may eliminate the need for complex input, transmission, and output force overload systems that might require additional springs, linkages, and structural members. In addition, these jaw closure transmission systems described herein may regulate needle clamp load, which helps reduce damage to needles, and/or may desensitize the system from a size and location of a needle held between the jaws, and provide an adequate clamping force without damaging the needle. These jaw closure transmission systems may also regulate handle lever force applied by the surgeon which is preferred from an ergonomic standpoint. In the case of a rigid transmission member, it becomes very difficult for the surgeon to regulate the clamping force at the jaws by adjusting his input force/displacement at the handle lever. In such cases, a very small change in the surgeon's input displacement at the handle lever can produce a large, somewhat uncontrolled, change in the clamping force. That is why, in such systems, there are discrete ratchet points between the handle lever and the handle body that allows the surgeon to incrementally increase the clamping force at the jaws in controlled amounts. The present jaw closure transmission system, with the intentional use of compliance in the transmission member and transmission guide members, provides the surgeon with a much greater control of the clamping force at the jaws, thus mitigating or eliminating the need for discrete ratchets at the handle lever (with respect to handle body). Rather, this system lets the surgeon rely upon his/her feel and discretion to regulate input force to achieve a desired needle clamping force. The use of a semi compliant transmission member enables the design of a device which eliminates the need for complex multi-lock ratcheting mechanisms in the handle assembly. A rigid or extremely stiff transmission member without a complaint member to build up force would result in a condition in which the jaws reach a stopping point and the remaining input stroke at the input sub-system is forced to stretch a transmission member with an extremely high axial stiffness resulting which will not be desirable due to ergonomic limitations at the user input as well as the system would be generating too large of clamping forces at the out sub-system damaging the material between the jaws causing the components within the transmission system to fail due to high stress loads. Therefore, system with a stiff transmission member are designed with a multi-stage ratcheting system to allow the user to lock the handle assembly are various locations depending on the desired clamping load without reaching a full input stroke. The variation in locking position can lead to uncertainty in clamping load generated with the user. These ratcheting systems require an additional user actuation component/input to disengage the locking mechanism, without which the tool has to overload the needle or object in the jaws to release it. An axial compliant transmission member enables the handle to embody a simpler locking mechanism, as it does not require an additional user input to disengage the lock. Simplifying the handle reduces potential user error and could result in less user training.

Also described herein are jaw closure transmission systems in which an additional intermediate transmission mechanism can be used. FIG. 3 illustrates one example of such a system, showing a handle b 301, handle mechanism 303, input lever/button 305, first transmission member 307, first transmission guide 309, intermediate transmission mechanism 311, second transmission guide 313, second transmission member 315, and jaw mechanism 317. For example, in addition to an input sub-system and an output sub-system, there may also be an intermediate sub-system with an intermediate mechanism. In that case there may be a first transmission member and transmission guide member between the input and intermediate sub-systems, and a second transmission member and transmission guide member between the intermediate and output sub-systems. The use of an axially compliant transmission member and transmission guide member may be preserved to achieve desired jaw closure performance.

In any of the apparatuses described herein the handle assembly input may be a handle lever, or any other input allowing a variable degree of actuation, and may generally be referred to herein as "levers", including plungers, dials, knobs, etc.

As mentioned, these jaw closure transmission systems may generally provide for connecting an input and an output comprising rigid and compliant transmission members, as well as rigid and flexible transmission guiding members, wherein the transmission members with finite flexibility in the transmission direction also serve to store energy during closure transmission to achieve unique and desirable functionality.

Thus, in a simple form, the system can be thought of as, but not limited to, three sub-systems that are serially connected that take an input, in the form of handle lever displacement by force from the user, and produce an output that presents a moving jaw displacement and clamp load.

The three sub-systems (input sub-system, which are referred to as the handle assembly consisting of a handle mechanism; output sub-system, which is referred to as the jaw mechanism; and transmission sub-system, which comprises a transmission member, e.g., cable, and transmission guide, e.g., flexible conduit) may be represented in a system diagram as shown in one example in FIG. 1. The example shown in FIG. 1 includes a handle body or handle shell 101, a handle assembly 103 comprising a handle mechanism having a handle lever 107 (input lever or input link), a transmission guide 109 (rigid pulley) and/or flexible conduit 109', a transmission cable 111, a return spring 113, a fixed jaw 115 (end-effector base/reference) an end-effector assembly 117 comprising a jaw mechanism including a drive pin 121, a pulley pivot pin 123, a pulley 119, and a jaw pivot pin 125.

The handle assembly may comprise a handle body or shell that serves as the local reference or ground. The handle body is generally designed to be ergonomic for the user to hold in various positions since it is generally the articulation of the handle body which controls the location and orientation of the end-effector. Mechanically the handle body can be directly connected to the end-effector via a tool shaft as in straight stick laparoscopic instruments, serially, or connected to the end-effector through an input articulating joint, a tool frame (e.g., a frame, or a frame with a shaft extension, or a shaft), and/or an output articulating joint having a series of joints which provide articulation to the end-effector or even indirectly attached to the end-effector, as described in U.S. Pat. No. 8,668,702. The handle body houses an internal transmission mechanism (or handle mechanism) consisting of a handle lever configured to receive user input in the form of a displacement relative to the handle body. Full handle lever displacement with respect to the handle body is referred to as the input stroke. This input stroke is based on the kinematic design of the handle mechanism and is limited by one or more hard-stops in the handle mechanism. This input stroke is designed to have a specific mechanical advantage curve profile that, when combined with the other sub assembles, is unique to the type of surgical instrument. Generally, for a surgical needle driver, the mechanical advantage curve of the input sub-system initially has a low mechanical advantage and then increases, to have a high mechanical advantage at the end of the input stroke. At full closure, i.e., the end of input stroke, the handle lever reaches a hard-stop relative to the handle body. At this hard stop, there may be a single locking or latching feature that keeps the handle lever latched closed relative to the handle body. As mentioned above, an unlatching/unlocking feature may unlock the handle lever and allow it to open again with respect to the handle body. The output of the handle mechanism is via the handle shuttle (or output member, pull rod, or push rod), which interfaces with the transmission member and provides an actuation motion to the proximal end of the transmission member. The output of the handle mechanism is not limited to a shuttle, the embodiment shown consists of a "shuttle" because the handle mechanism is a six-bar linkage with a 1 DoF slider joint between the output member (shuttle) and handle body. The handle mechanism is not limited to a six-bar linkage. The handle mechanism could be a simple lever, four-bar linkage, cam slot, gear, etc. The handle mechanism may be configured to provide a varying transmission ratio and mechanical advantage between the handle lever and the handle shuttle, so as to produce the appropriate actuation displacement and force at the proximal end of the transmission member (i.e., appropriate cable tension and cable displacement) via the handle shuttle during the overall stroke of the handle lever (i.e., input stroke). The handle mechanism itself may take the form of various configurations. As opposed to a six-bar linkage as cited, in some variations, the linkage system may be a four-bar linkage, or any alternate system containing a plurality of linkages or motion members that actuates the transmission member either by rotary or linear motion. Conversely, any of the linkages contained within the linkage system could be driven by a cam that is purposefully designed to induce a variable mechanical advantage throughout the handle's jaw closure lever stroke. FIG. 13 shows an input sub-system consisting of a cam (cam surface 1301 and cam transmission member 1305) which achieves the desired variable mechanical advantage. FIG. 13 also shows a shuttle 1307 connected to a shuttle actuation tension member 1309, within the handle body 101. In some variations, the linkage system may be a compliant mechanism that achieves the desired constant or variable transmission ratio. This mechanism may lead to part count reduction by still achieving similar performance. In some variations, the handle mechanism is designed such that instead of providing a constant mechanical advantage or transmission ratio, it produce produces a higher transmission ratio (lower mechanical advantage) in the first portion of the input stroke and a lower transmission ratio (higher mechanical advantage) in the second portion of the input stroke. While the mechanism for input into the input sub-system generally includes an actuating lever body, or ground reference, and a handle input lever, the input sub-system may be embodied alternatively. The input sub-system may be embodied as a motion member capable of translating mechanical energy therein. For example, the input motion member may be a button, dial, tension rod, or binary switch.

The output may generally be a jaw mechanism comprising a jaw base (which may include or be integral) with a fixed jaw that serves as the local reference or ground (alternatively two moving jaws may be used), and the movable jaw may be coupled to the fixed jaw (e.g., pivotally coupled to the fixed jaw) such that it can open and close (i.e., displace) with respect the fixed jaw. The structure of one end-effector (jaw assembly) embodiment is seen in FIGS. 1, 2, 11, 12A, and 12B. As discussed above, the full closure displacement of the end-effector moving jaw relative to the end-effector fixed jaw is referred to as the output stroke. The purpose of this closure displacement of the end-effector moving jaw relative to the end-effector fixed jaw is to hold an object (such as needle, suture, tissue, staple, clip etc.) between the jaws in response to a corresponding closure displacement of the handle lever relative to the handle body at the input of the closure transmission system. The embodiment shown incorporates, but is not limited to, a two-stage mechanical mechanism to produce the desired mechanical advantage curve with the desired mechanical advantage curve having a low mechanical advantage to start with and then having a high mechanical advantage at the end. The design is not limited to the current embodiment as long as the mechanical advantage curve is conserved. In the embodiment shown, an end-effector pulley coupled to the end-effector fixed jaw or the fixed bearing member (e.g., pivotally coupled to the end-effector fixed jaw) is configured to receive the actuation motion from the distal end of the transmission member. A jaw mechanism (e.g., comprising a drive pin/cam surface) may translate the actuation motion of the transmission member distal end to a corresponding closure motion of the moving jaw relative to the end-effector fixed jaw. In this example of the end-effector mechanism, a drive pin is driven by the end-effector pulley and interfaces with a camming surface on the moving jaw, providing a camming action. Additionally, in this example of the end-effector mechanism, the distal end of the transmission member (i.e., cable) is wrapped around the end-effector pulley. To prevent a potential slippage between the cable and the pulley, there may be a positive engagement feature between the cable and the pulley. This may be accomplished via a cylindrical member that is crimped onto the cable and sits in a cavity on the pulley. Once the cable is wrapped around the pulley, it is connected to a return spring either in the jaw assembly, or on the transmission guide, or in the handle assembly. The purpose of this return spring is to open the jaws after full closure is reached and the handle lever returns to the initial open angle. The end-effector mechanism is designed to provide a varying transmission ratio and mechanical advantage between the distal end of the transmission member and the end-effector moving jaw so as to produce the appropriate output displacement and force at the end-effector moving jaw relative to the end-effector fixed jaw during the overall stroke of the end-effector moving jaw (i.e., output stroke). This optimization is based on the structure and functionality of the overall closure transmission system including the input sub-system, transmission sub-system, and output sub-system, and not just the output sub-system. Specifically, the end-effector mechanism is designed to provide a large mechanical advantage at the end of its stroke, to maximally amplify the force in the transmission member (i.e., tension in the jaw closure transmission cable) to a clamping force at the jaws. This implies that for a certain desired jaw clamping force, if the mechanical advantage of the jaw mechanism is high when the jaws are closed, the transmission cable tension can be lower, which has several advantages. The end-effector may include many different embodiments but is not limited to a pair of jaws, useful for manipulation of needles, suture, tissue, cautery, ligation clip application, etc.

The intermediate transmission sub-system may comprise the following elements, a transmission member to transmit the output of the input sub-system (i.e., handle assembly) to the input of the output sub-system (i.e., end-effector assembly) of the closure transmission system. More specifically, the transmission member transmits the actuation motion of the handle shuttle to a corresponding actuation motion of the end-effector pulley. This transmission member is a cable, braided rope, etc. that is capable of accommodating very tight bends as might be necessary when the closure transmission system is part of a remote access tool or device as seen in FIGS. 1, 10, 15, and 16. The transmission member is highly compliant (i.e., flexible) in bending, twisting, and compression. This member is relatively stiffer in tension because it has to transmit force and displacement along this direction; but at the same time, it is not chosen or designed to be infinitely or effectively infinitely stiff. Rather, it is intentionally designed or chosen to have a finite stiffness (or finite compliance) so that it can also serve as an inline spring. The importance of this finite stiffness for the system level performance is described below. Note that nothing is infinitely stiff or infinitely compliant. Infinite stiffness corresponds to zero compliance and zero stiffness corresponds to infinite compliance. On some normalized scale, a stiffness less than 10 is close to infinitely compliant and a stiffness greater than 1000 is closely to infinitely stiff. On such a scale, a stiffness in the range of 100-200 is where we might place the axial stiffness of the transmission member.

A transmission guide may serve as a conduit or channel (also, a reference) for the transmission member. A proximal portion of this transmission guide is connected to the input sub-system reference (i.e., handle body) and the distal portion of this transmission guide is connected to the output sub-system reference (i.e., end-effector fixed jaw). This guide may be completely rigid in all directions such as a frame, or a shaft, or tube as seen in FIG. 2. This guide may also be flexible in bending so that it can take an arbitrary, tortuous shape but still remain very stiff (ideally, close to infinitely stiffness) axially (i.e., along its bent/deformed central axis). The connections between the ends of the guide and respective references of the input and output sub-systems may be close to infinitely stiff in the transmission direction (i.e., axial direction of the transmission cable) or may have some intentionally finite compliance (i.e., slightly lower stiffness than infinitely stiff values). FIG. 2 shows a handle assembly 202 comprising a handle mechanism including a handle lever 201 (input link or input lever), a cable 207, a handle body (or handle reference) 203, a return spring 205, a transmission guide member 209, a fixed jaw 211 (end-effector base or reference), an end-effector assembly 213 comprising a jaw mechanism including a pulley 215, a pulley pivot pin 217, a drive pin 219, and a jaw pivot pin 223.

For example, described herein are medical devices having a jaw assembly actuated by a transmission cable having a finite stiffness in a transmission direction. For example the devices may include: an elongate transmission guide, wherein the transmission cable is routed through the transmission guide; a handle assembly at a proximal end of the elongate transmission guide, the handle assembly comprising a handle body, an input lever, a handle output coupled to the transmission cable, and a handle mechanism coupling the input lever to the handle output, wherein the handle mechanism has an input stroke consisting of a full closure displacement of the input lever relative to the handle body, further wherein the input stroke is divided into a first part and a second part, wherein the first part corresponds to a displacement of 30% to 70% of the full closure displacement of the input lever and the second part corresponds to the remaining displacement of the input lever; and wherein the jaw assembly is distal to the elongate transmission guide, the jaw assembly having a first jaw, a second jaw, a jaw input coupled to the transmission cable, and a jaw mechanism coupling the jaw input to the second jaw, wherein the jaw mechanism has an open configuration when the first and second jaws are fully open relative to each other and a closed configuration when the first and second jaws are fully closed; further wherein the displacement of the input lever relative to the handle body corresponding to the first part of the input stroke actuates the handle output which in turn actuates the jaw input via the transmission cable, which in turn closes the first and second jaws until the first and second jaws reach a hard stop, and thereafter the displacement of the handle lever relative to the handle body corresponding to the second part of the input stroke stretches the transmission cable, wherein the resulting tension in the transmission cable is converted by the jaw mechanism to a force between the first and second jaws.

A medical device having a jaw assembly actuated by a transmission cable having a finite stiffness in a transmission direction may include: an elongate transmission guide comprising a flexible conduit, wherein the transmission cable is routed through the transmission guide; a handle assembly at a proximal end of the elongate transmission guide, the handle assembly comprising a handle body, an input lever, a handle output comprising a shuttle coupled to the transmission cable, and a handle mechanism comprising a six-bar linkage coupling the input lever to the handle output, wherein the handle mechanism has an input stroke consisting of a full closure displacement of the input lever relative to the handle body, further wherein the input stroke is divided into a first part and a second part, wherein the first part corresponds to a displacement of 30% to 70% of the full closure displacement of the input lever and the second part corresponds to the remaining displacement of the input lever; and wherein the jaw assembly is distal to the elongate transmission guide, the jaw assembly having a first jaw, a second jaw, a jaw input comprising a pulley coupled to the transmission cable, and a jaw mechanism comprising a cam surface between the jaw input and the second jaw, wherein the jaw mechanism has an open configuration when the first and second jaws are fully open relative to each other and a closed configuration when the first and second jaws are fully closed; further wherein the displacement of the input lever relative to the handle body corresponding to the first part of the input stroke actuates the handle output which in turn actuates the jaw input via the transmission cable, which in turn closes the first and second jaws until the first and second jaws reach a hard stop, and thereafter the displacement of the handle lever relative to the handle body corresponding to the second part of the input stroke stretches the transmission cable, wherein the resulting tension in the transmission cable is converted by the jaw mechanism to a force between the first and second jaws (e.g., holding force, gripping force, cutting force, grasping force, etc.).

The handle mechanism may be a linkage (e.g., six-bar linkage, four-bar linkage, etc.) or a cam (cam surface and pin, etc.). In general, the elongate transmission guide may comprise a flexible conduit or elongate shaft or both.

The transmission cable may generally have a finite stiffness in the direction of transmission (e.g., along the length of the extended cable). For example the transmission cable may have a stiffness in a transmission direction of less than 800 pounds per inch, less than 700 pounds per inch, less than 650 pounds per inch, less than 600 pounds per inch, less than 500 pounds per inch, less than 400 pounds per inch, etc. (and in some variations be greater than 100 pounds per inch, greater than 150 pounds per inch, greater than 200 pounds per inch, greater than 250 pounds per inch, greater than 300 pounds per inch, etc., e.g., between 100 and 650 pounds per inch, etc.).

In any of these apparatuses (devices, systems, mechanism, tools, etc.) the handle mechanism may be configured to provide a first mechanical advantage during the first part of the input stroke and a second mechanical advantage that is greater than the first mechanical advantage during the second part of the input stroke. The handle output may comprise one or more of: a shuttle, a push rod, or a pull rod. The device may include a jaw base to which either or both the first and second jaws are pivotally coupled.

The jaw input may comprise a jaw pulley, and the jaw mechanism may comprise a cam surface between the jaw pulley and the second jaw.

As mentioned above, any of these devices may include a releasable latching mechanism configured to hold the handle lever locked in a closed position at the end of the input stroke.

Also described herein are methods of using any of the apparatuses including these jaw closure transmission systems. For example, described herein are methods of operating a medical device to close a jaw assembly of the medical device, wherein the medical device comprises an elongate transmission guide, a finite stiffness transmission cable within the transmission guide, and a handle assembly at the proximal end of the elongate transmission guide having an input lever and a handle mechanism coupling the input lever to the transmission cable, wherein the transmission cable is coupled to a jaw input of the jaw assembly, wherein the jaw assembly is distal to the elongate transmission guide. The method may include: actuating the input lever to apply tension to the transmission cable during a first part of an input stroke of the handle assembly to close a first and second jaw of the jaw assembly from an open configuration until the first and second jaws reach a hard stop; and continuing to actuate the input lever during a second part of the input stroke after the first and second jaws have reached the hard stop, and stretching the transmission cable; wherein the input stroke consists of a full displacement of the handle lever of the handle assembly, and further wherein the handle assembly transitions from the first part of the input stroke to the second part of the input stroke when the handle is between 30% and 70% displaced.

A method of operating a medical device to close a jaw assembly of the medical device (wherein the medical device comprises an elongate transmission guide, a finite stiffness transmission cable within the transmission guide, and a handle assembly at the proximal end of the elongate transmission guide having an input lever and a handle mechanism coupling the input lever to the transmission cable, wherein the transmission cable is coupled to a jaw input of the jaw assembly, and wherein the jaw assembly is distal to the elongate transmission guide) may include: actuating the input lever to actuate the transmission cable during a first part of an input stroke of the handle assembly and translate the transmission cable relative to the elongate shaft to close a first and second jaw of the jaw assembly from an open configuration until the first and second jaws reach a hard stop; and continuing to actuate the input lever and stretching the transmission cable without translating the first or second jaws during a second part of the input stroke after the first and second jaws have reached the hard stop; wherein the input stroke consists of a full displacement of the handle lever of the handle assembly, and further wherein the handle assembly transitions from the first part of the input stroke to the second part of the input stroke when the handle is between 30% and 70% displaced.

Any of these methods may include applying a first mechanical advantage during the first part of the input stroke and applying a second mechanical advantage that is greater than the first mechanical advantage during the second part of the input stroke. These methods may also include grasping an object between the first and second jaws, wherein the first and second jaws reach the hard stop when the object is secured between the first and second jaws.

Any of these methods may also include locking the input lever in a fully closed position relative to a handle shell in the handle assembly.

Any of these methods may also include releasing the input lever to transition the handle lever from the second part of the input stroke to the first part of the input stroke, reducing the tension on the transmission cable and reducing the stretch of the transmission cable before translating the transmission cable so that the first and second jaws open. Actuating the input lever may comprise squeezing the input lever.

As mentioned, these jaw closure transmission systems may be integrated into any appropriate apparatus. For example, any of these apparatuses may be configured as a medical device, see for example FIGS. 15 and 16, including a jaw closure transmission system. For example, a medical device having a distal jaw assembly actuated by a transmission cable having a finite stiffness in the transmission direction that is compliant in bending may include: a tool frame comprising an elongate shaft and a forearm attachment region at a proximal end of the tool frame configured to couple with an arm attachment cuff; a handle assembly, the handle assembly comprising a handle shell configured to be gripped in a user's palm and an input lever on the handle shell, wherein the handle shell encloses a handle linkage coupling the input lever to the transmission cable through a handle output, further wherein the handle assembly has an input stroke consisting of a full closure displacement of the input lever from an undisplaced configuration to a fully displaced configuration, further wherein the input lever transitions from a first part of the input stroke to a second part of the input stroke when the input lever is displaced from an undisplaced configuration to between 30% and 70% of its full closure displacement configuration; an input joint between the handle and the tool frame configured to encode motion of the handle about a pitch axis of rotation relative to the tool frame for transmission to an articulating output joint, and further configured to encode motion of the handle about a yaw axis of rotation relative to the tool frame for transmission to the articulating output joint, wherein the pitch axis of rotation and the yaw axis of rotation intersect in a center of rotation; wherein the jaw assembly is coupled to the distal end of the elongate tool shaft by the articulating output joint, the jaw assembly having a first jaw, a jaw pulley pivotally coupled to the first jaw and further coupled to the transmission cable, a second jaw pivotally coupled to the first jaw, and a cam surface that translates motion of the jaw pulley to a motion of the second jaw relative to the first jaw, wherein the jaw assembly has an output stroke that extends from an open configuration when the first and second jaws are fully open to a closed configuration when the first and second jaws are fully closed; wherein the displacement of the input lever relative to the handle body corresponding to the first part of the input stroke actuates the handle output which in turn actuates the jaw input via the transmission cable, which in turn closes the first and second jaws until the first and second jaws reach a hard stop, and thereafter the displacement of the handle lever relative to the handle body corresponding to the second part of the input stroke stretches the transmission cable, wherein the resulting tension in the transmission cable is converted by the jaw mechanism to a force between the first and second jaws; and a transmission guide extending between the handle assembly and the elongate shaft, wherein the transmission cable extends from the handle assembly, through the transmission guide to the jaw assembly. FIGS. 10, 14, 15 and 16 illustrate one example of such an apparatus.

In FIG. 10, a medical device apparatus includes a jaw closure transmission as described above. The exemplary apparatus includes a tool frame 525, which includes a tool shaft 526 and a forearm attachment portion at the proximal end 527. A cuff (not shown) having a passage therethrough that is configured to hold a wrist or forearm of a user may be coupled to the forearm attachment portion, in some variations via a bearing between the forearm attachment portion of the frame and the cuff that is configured to slide or roll so that there is a roll rotational degree of freedom between the frame and the cuff about the tool axis. A proximal handle assembly may be connected to the tool frame by an input joint. The input joint may be configured to encode motion between the tool frame and the handle assembly, as shown in FIG. 10. In this example, the input joint includes a pair of transmission strips 533, 534 that connect to respective pivoting joints (not shown) in parallel to separately encode pitch and yaw rotations of the handle assembly. The output joint 583 (an end-effector articulation joint configured as a jaw assembly), as shown in FIG. 14, may be any of the multi-cluster joints described herein and is between the jaw assembly and the tool frame (e.g., tool shaft) and receives transmission input (e.g., cables, not shown) from the output joint (including transmission strips 533, 534 of the output joint) to articulate the jaw assembly.

In this example, the handle assembly includes an ergonomic palm grip portion 501 (handle shell) that connects to the rotation dial 502. The handle assembly also includes a control (lever) 549 input]]) that is configured as a handle lever and acts as a rigid extension of the internal push rod. A transmission cable 566 connects to the shuttle and acts as a jaw closure actuation transmission member extending from the shuttle and through the tool shaft 526 to the jaw assembly. This transmission cable may be enclosed by a protective and/or supporting sheath or cover or conduit, for some or the entire portion of its length. The end-effector is a jaw assembly including a first (ground) end-effector portion, in this example, including a fixed jaw 569 to which a pivoting second end-effector portion (moving jaw 568) is attached. The transmission cable 566 may couple to the moving jaw 568 at the end-effector closure output 577.

In FIG. 10, rotation of the dial portion 502 of the handle assembly when the user's forearm is mounted to the proximal end and the palm grip region 501 is held in the user's hand so that the user can rotate the dial between the thumb and fingers, rotates the entire tool frame, and therefore the end-effector that is attached to the distal end of the tool shaft 526 via an end-effector output articulating joint 583. Thus, the handle may rotate about first axis 511, referred to as the handle articulated roll axis (axis 1), to cause the tool shaft to rotate in a third axis 515, referred to as the tool shaft roll axis (axis 3), in turn causing the end-effector to roll about a second axis 513, referred to as an end-effector articulated roll axis (axis 2).

The rotation dial 502 as shown in FIG. 10 is rotated about the first axis 511. The rotation leads to rotation of tool frame 525 via transmission strips 533, 534 (as they constrain rotation DoF), rotation of the tool shaft 526 (about the third axis 515), and therefore, the rotation of the end-effector (about the second axis 513). When the handle is articulated using the input articulating joint, the output joint (multi-cluster joint 583) and the end-effector articulate via the output articulating joint 583. The center axis (axis 2) 513 for the end-effector is different from the axis 3, the shaft axis 515. The intermediate transmission mechanism consists of but is not limited to a cam mechanism as seen in FIG. 3B. The intermediate transmission mechanism could be a linkage, gear, cog etc. During input stroke A, the force is not being amplified through the intermediate transmission mechanism, however at the transition from stroke A to stroke B the first transmission member lifts off the hub 353 and rides a surface farther away from the cam's center of rotation, creating a force amplification from the first transmission member to the second transmission member. This force amplification increases the mechanical advantage of the system. This mechanism is shown in the structure of the device in FIG. 3C (e.g., including transmission cam 361, transmission members 362, return pulley 363 and return spring 364). While this transmission system invention is specifically embodied as a laparoscopic, endoscopic, or other minimally invasive surgical jaw closure device, it is understood that those skilled in the art can alternately translate the invention, without departing from the scope, to alternate embodiments for transmission systems such as those that require end-effector clamping action like grasping, holding, or clamping instruments.

For example, described herein are apparatuses, e.g., devices and systems (including, but not limited to medical devices) that include a jaw assembly actuated by a transmission cable having a finite stiffness in a transmission direction, the apparatus comprising: an elongate transmission guide, wherein the transmission cable is routed through the elongate transmission guide; an input assembly at a proximal end of the elongate transmission guide, the input assembly comprising an input body and an input member, the input member coupled to the proximal end of the transmission cable, wherein the input member has an input stroke relative to the input body that is divided into a first part and a second part, wherein the first part corresponds to a displacement of 30% to 70% of the full displacement of the input member and the second part corresponds to the remaining displacement of the input member; and wherein the jaw assembly is distal to the elongate transmission guide, the jaw assembly having a first jaw, a second jaw, and a jaw input coupling the transmission cable to the second jaw or the first and second jaw, wherein the jaw assembly has an open configuration when the first and second jaws are fully open relative to each other and a closed configuration when the first and second jaws are closed; further wherein the displacement of the input member relative to the input body corresponding to the first part of the input stroke actuates the proximal end of the transmission cable which in turn actuates the jaw input, which in turn closes the first and second jaws until the first and second jaws reach a stop, and thereafter the displacement of the input member relative to the input body corresponding to the second part of the input stroke stretches the transmission cable, wherein the resulting tension in the transmission cable is converted by the jaw mechanism to a force between the first and second jaws.

Any of these apparatuses may include an intermediate transmission, wherein intermediate transmission is configured to provide a first mechanical advantage during the first part of the input stroke and a second mechanical advantage that is greater than the first mechanical advantage during the second part of the input stroke.

As described herein, in some variations the input assembly includes (or is configured as) a handle assembly, which may receive input from a user's hand. Alternatively, in some variations the input assembly may be configured to couple with a handle. For example, the input body may be configured to removably couple with a handle assembly. The input body may be configured to couple to a handle shell, which may form part of an outer housing of a handle. In some variations the input body configured as the handle shell or a portion of a handle shell. The input member may be an input that may be manipulated directly or indirectly by a user. For example, in some variations the input member includes an input machine, such as an input lever; the input member may be part of a handle or may be configured to couple with a portion of a handle such as an input machine (e.g., input lever, also referred to in some examples herein as a handle lever or input handle lever). As mentioned, in some variations the input member is configured to couple with a handle assembly. For example, the input member may couple to a handle assembly, including coupling to an input lever when the input body is coupled with the handle assembly.

The input assembly may include a linkage (e.g., a six-bar linkage) and/or a cam. The input assembly may also include an input assembly output coupled to the proximal end of the elongate transmission guide. In some example, the input assembly output comprises one or more of: a shuttle, a push rod, or a pull rod.

The elongate transmission guide may include a conduit that is flexible in bending and/or is stiff at least along a region through which the transmission cable is routed.

Any of these apparatuses may include an output assembly, such as a jaw assembly. For example, a jaw assembly may include a jaw base to which either or both the first and second jaws are pivotally coupled. The jaw input may include a jaw pulley, and the jaw mechanism comprises a cam surface between the jaw pulley and the second jaw.

Any of these devices may include a releasable latching mechanism configured to hold the input member locked in a closed position at the end of the input stroke.

Also described herein are methods of operating any of these apparatuses. For example, described herein are methods of operating a medical device to close a jaw assembly of the medical device, wherein the medical device comprises an elongate transmission guide, a transmission cable within the transmission guide, and an input assembly at the proximal end of the transmission cable, the input assembly having an input member coupled to the transmission cable, wherein the transmission cable is coupled to a jaw input of the jaw assembly, wherein the jaw assembly is distal to the elongate transmission guide, the method comprising: actuating the input member to apply tension to the transmission cable during a first part of an input stroke of the input assembly to close a first and second jaw of the jaw assembly from an open configuration until the first and second jaws reach a stop; continuing to actuate the input member during a second part of the input stroke after the first and second jaws have reached the stop and stretching the transmission cable; wherein the input stroke consists of a displacement of the input member, and further wherein the input member transitions from the first part of the input stroke to the second part of the input stroke when the input member is between 30% and 70% displaced; and applying a first mechanical advantage during the first part of the input stroke and applying a second mechanical advantage that is greater than the first mechanical advantage during the second part of the input stroke.

The first mechanical advantage and the second mechanical advantage may be applied by an intermediate transmission coupled to the transmission cable between the input assembly and the jaw assembly. Any of these apparatuses may include grasping an object between the first and second jaws, wherein the first and second jaws reach the stop when the object is secured between the first and second jaws.

The methods may include locking the input member in a fully closed position. Any of these methods may also include releasing the input member to transition from the second part of the input stroke to the first part of the input stroke, reducing the tension on the transmission cable and reducing the stretch of the transmission cable before translating the transmission cable so that the first and second jaws open.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 shows various cross-sections for needles that are commonly used in minimally invasive surgery and that may be grasped by an apparatus including any of the jaw closure transmission systems described herein.

In FIG. 11, the end-effector assembly may include a movable jaw 1101 (having an engagement surface 1102, jaw pivot 1103, clearance slot 1104, and drive slot 1105), a pulley 1103 (having a drive pin 110) that connects to a cable 1109, and a fixed jaw 1111 (having an engagement surface 1112, pulley pivot pin 1114, and movable jaw pivot pin 1113).

FIG. 12A shows a detailed view of an end-effector assembly where the moveable jaw is in open condition.

FIG. 12B shows a detailed view of an end-effector assembly where the moveable jaw is grasping a needle.

FIGS. 21A-21C illustrate operation of a transmission cam that may be included as part of a transmission mechanism as described herein. FIGS. 21A-21C illustrate the rotation of the transmission cam as the input stroke changes.

FIGS. 22A-22F show six examples of transmission mechanisms that may be used, including as part of an intermediate transmission mechanism, as described herein.

In FIG. 24, a virtual control unit (VCU) assembly, which is configured as a handle assembly, may be coupled on the proximal end of the device to the input member. The device also shown a cartridge assembly on the distal end. The cartridge assembly includes the elongate transmission guide, transmission cable and output assembly (e.g., jaw assembly) as well as an intermediate transmission.

FIG. 26A shows the minimally invasive surgical device with the device (e.g., "cartridge") uncoupled from the handle assembly, while FIG. 26B illustrates the minimally invasive surgical device with the device coupled to the handle assembly.

In FIG. 28, an interface is positioned between the output sub-system and the input and transmission sub-systems to form one larger jaw closure transmission system at the distal end of the shaft.

FIG. 31B includes a jaw assembly with a jaw return spring while in FIG. 31A the jaw assembly does not include a return spring.

FIGS. 32A-32G illustrated an output assembly configured as a jaw assembly which may be used for cutting material as the blade translates within the jaws. FIGS. 32A-32C show an example with the blade disengaged while FIGS. 32D-32F shows an example with the blade activated. FIG. 32G shows an isometric view of the jaw assembly.

FIGS. 33A-33C illustrate the interaction of a translating shuttle as a coupler between an input member and an output member. FIGS. 33A and 33B show the coupler disengaged and engaged with the jaw closure crimp respectively while FIG. 33C shows the jaw closure crimp in detail in an isometric view.

FIGS. 34A-34B show an example of a coupler mechanism which uses rotation to transfer motion from an input to an output. FIG. 34A and FIG. 34B show the coupler disengage and engaged with the output member, respectively.

FIGS. 35A-35B show an example of a coupler mechanism which uses a lead screw to transfer the motion from an input to an output. FIGS. 35A and 35B show the coupler disengage and engaged with the output member, respectively.

DETAILED DESCRIPTION

Described herein are jaw closure transmission systems and apparatuses including them. For example, described herein are transmission systems (jaw closure transmission systems) for a remote access tool which incorporates a transmission member with finite transmission direction stiffness (or equivalently, a compliant transmission member) that interfaces with the input and output mechanisms of the remote access tool. The transmission systems described herein are configured to operate together to achieve improved performance.

In general, described herein are apparatuses having an output assembly (e.g., jaw assembly) actuated by a transmission cable having a finite stiffness in a transmission direction, in which the device may include: an input assembly at a proximal end (e.g. proximal to an elongate transmission guide), the input assembly comprising an input body and an input member, the input member may have an input stroke that is divided into a two or more parts (e.g., first part and a second part, wherein the first part corresponds to a displacement of 30% to 70% of the full displacement of the input member and the second part corresponds to the remaining displacement of the input member). The jaw assembly may be distal to the elongate transmission guide. The jaw assembly may have a first jaw, a second jaw, and a jaw input coupling the transmission cable to the second jaw or the first and second jaw. The jaw assembly may have an open configuration when the first and second jaws are fully open relative to each other and a closed configuration when the first and second jaws are closed. In any of these apparatuses, the displacement of the input member relative to the input body corresponding to the first part of the input stroke may actuate the proximal end of the transmission cable which in turn actuates the jaw input, which in turn may close the first and second jaws until the first and second jaws reach a stop, and thereafter the displacement of the input member relative to the input body corresponding to the second part of the input stroke stretches the transmission cable. The resulting tension in the transmission cable may be converted by the jaw mechanism to a force (e.g., holding force, gripping force, cutting force, grasping force, etc.) between the first and second jaws.

Figure 1:
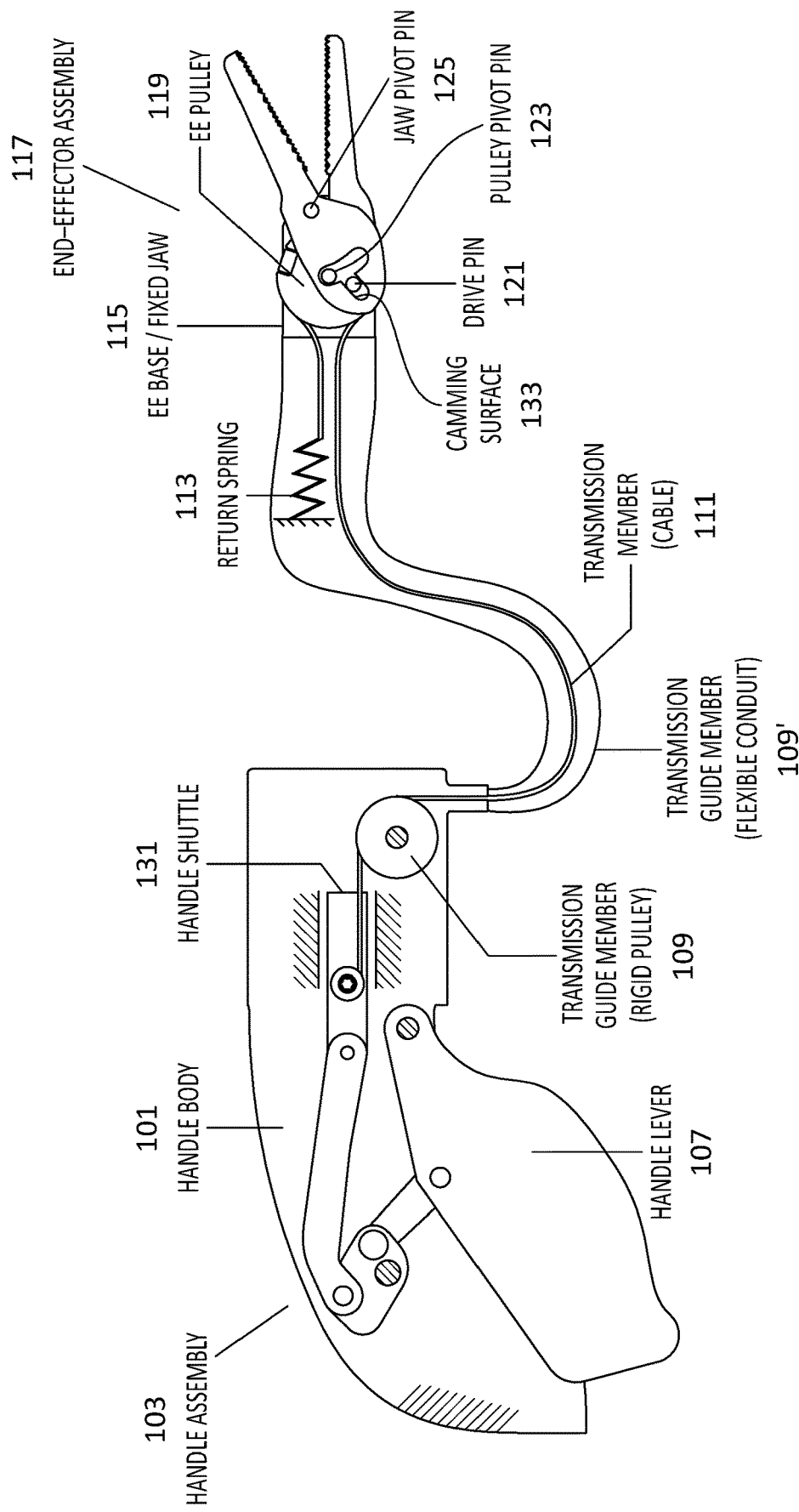
FIG. 1 shows an example of a system diagram of a jaw closure transmission system consisting of an input sub-system, a flexible transmission sub-system and an output sub-system.
Figure 2:
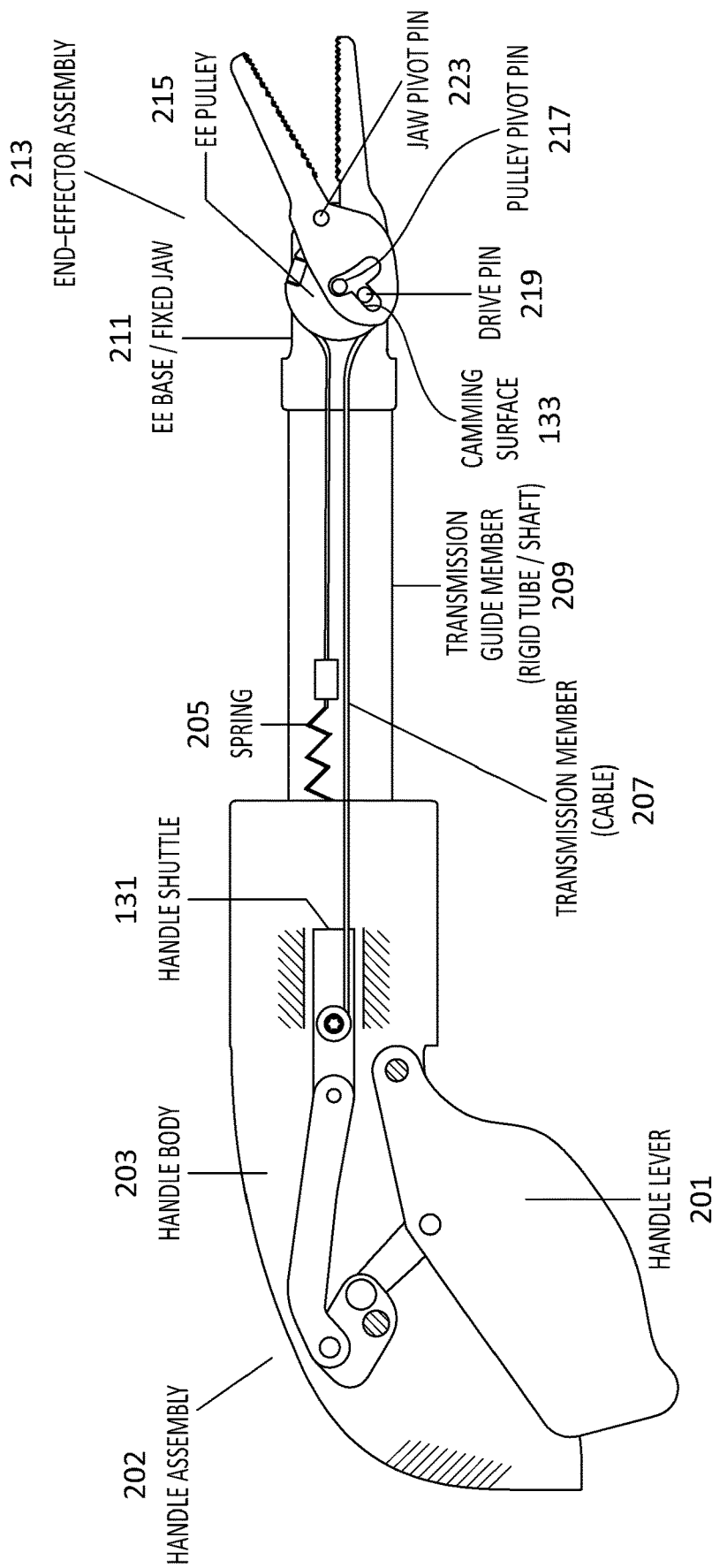
FIG. 2 is another diagram showing an example of a jaw closure transmission system consisting of an input sub-system, a rigid transmission sub-system and an output sub-system.

The assemblies (e.g., input assembly, output assembly, transmission assembly, etc.) may be sub-assemblies of the apparatuses described herein. For example, FIG. 1 shows an example of a device having an output sub-assembly configured as a jaw assembly. The jaw assembly is actuated by the transmission member (transmission cable) that passes through an elongate transmission guide. The device in FIG. 1 also includes an input assembly (input sub-assembly) that is configured, in this example, as a handle assembly. The input assembly includes an input body and an input member. The input body in this example is shown as a handle body, while the input member includes an input lever, shown a handle lever. The input lever is coupled to the transmission cable through a linkage in FIG. 1. As described above, these components are coupled together so that the displacement of the input member (e.g., handle lever) relative to the input body pulls the transmission cable. The first part of the input stroke actuates the jaw input, which closes the jaws until they reach a stop; thereafter the apparatus is configured so that further displacement of the input member relative to the input body is possible (e.g., the handle moves), but the jaw does not further move. This further movement corresponds to the second part of the input stroke and result in stretching the transmission cable, wherein the resulting tension in the transmission cable is converted by the jaw mechanism to a force between the first and second jaws. The transmission sub-system, which may include one or more intermediate transmissions (e.g., intermediate transmission mechanisms), that may adjust the mechanical advantage during the first part of the input stroke relative to the second part of the input stroke. For example, the intermediate transmission may be configured to provide a first mechanical advantage during the first part of the input stroke and a second mechanical advantage that is greater than the first mechanical advantage during the second part of the input stroke, as described below in reference to FIGS. 8 and 9.

In some examples these apparatuses (e.g., device, systems, etc.) are configured as needle drivers. Surgical needle drivers are typically one-handed devices which require high clamping loads at jaw clamping surfaces in order to drive various needles through tissues. It is important to understand the various types of needles because the design of a compliant transmission member can protect the needle from damage when overdriving the jaws. FIG. 4 shows various needle types that are selected based on the medium that they are driven through. The body of the needle is just as important as the tip, in that, as the needle is driven through the tissue, there is an interaction between the needle in its entirety and the tissue. The jaws of a needle driver are designed with a pattern intended to increase the needle retention without requiring high jaw clamping loads. However, if a large enough clamping load is applied to the needle, the clamping surfaces will damage the needle body, leaving permanent impressions on the needle surface. When the surface of the needle is damaged, it will no longer slide smoothly through the tissues, which will result in resistance felt by the surgeon and unnecessary damage to the patient.

Figure 5:
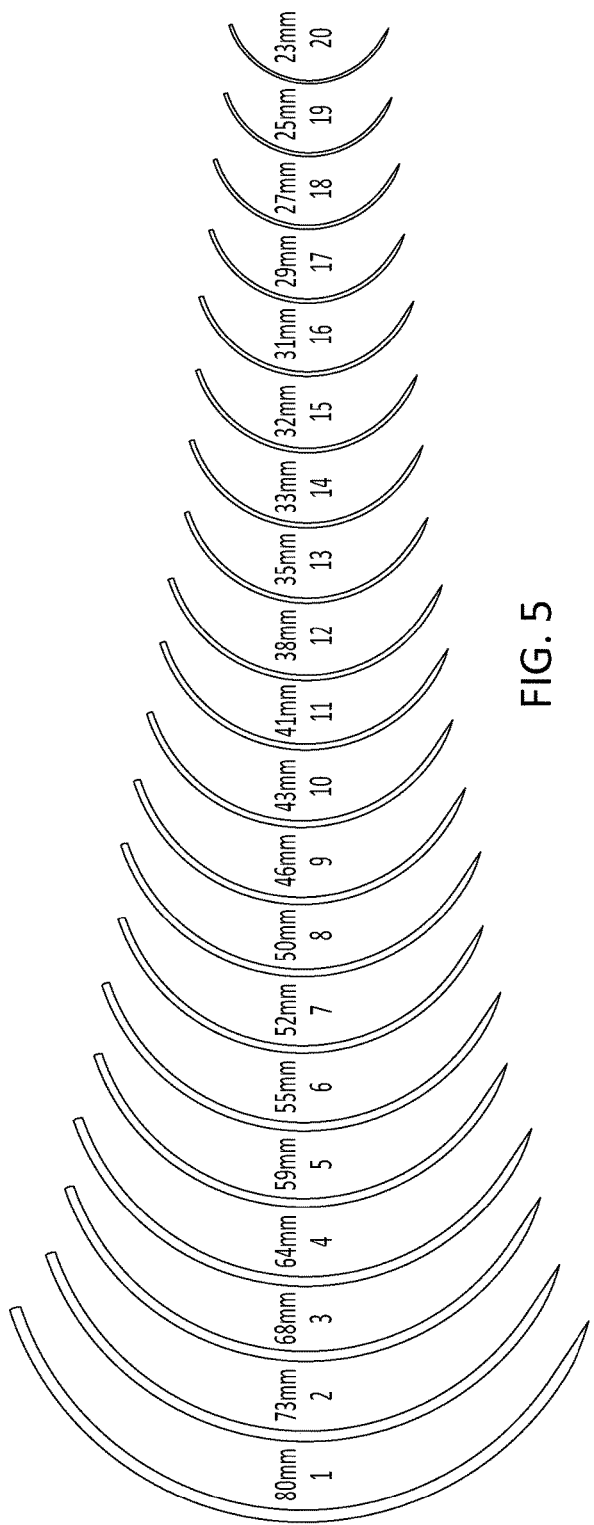
FIG. 5 illustrates various needle sizes that are commonly used in minimally invasive surgery.
Figure 7:
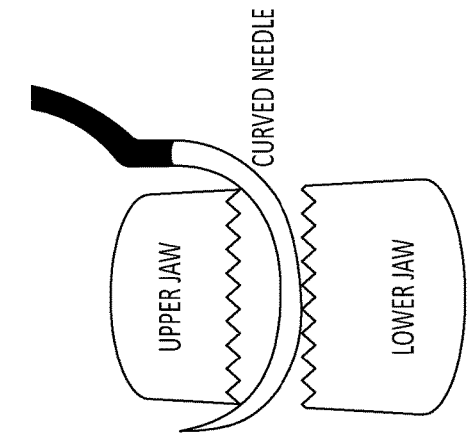
FIG. 7 is a front view of needle driver jaws clamping down on a curved needle.
Figure 6:
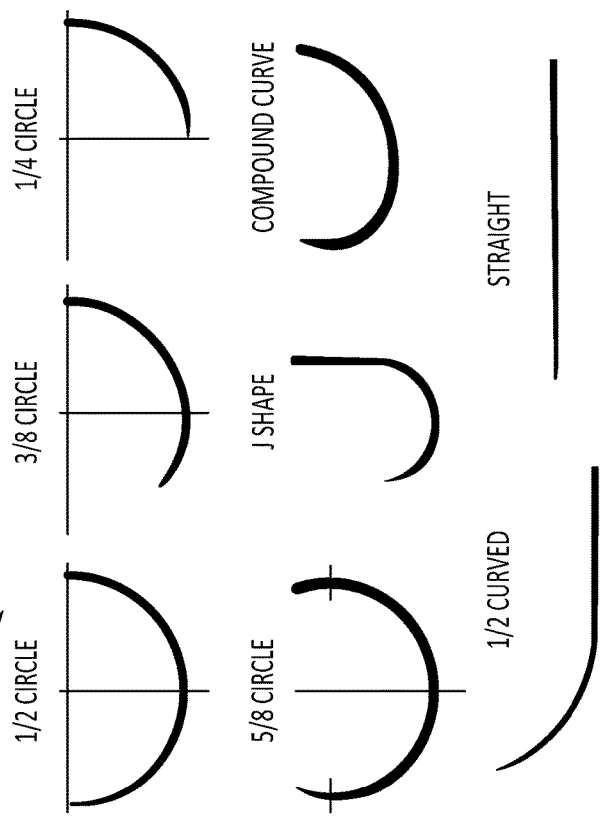
FIG. 6 shows various needle geometries that are commonly used in minimally invasive surgery.

In addition to surface damage on the needle, an overload in clamping force could cause the shape of the needle to permanently deform. Needles used for minimally invasive surgery also come in various shapes and sizes, as seen in FIG. 5 and FIG. 6 respectively. The jaws of the needle driver are designed to be wide enough to not allow the needle to rotate; as a result, needles with a larger curve and smaller diameter can be easily deformed and straighten out by large clamping loads. FIG. 7 showed a curved needle being held by the upper and lower jaws of a needle driver; as a larger clamping load is applied, the needle would straighten in that region due to three-point bending, causing the needle to not drive through the tissue in a true arc.

The needle location in the jaws also influences the corresponding jaw clamping force and impacts its ability to adequately secure a needle. The needle can be placed anywhere along the jaw length which could mean at the very tip of the jaws or at the mouth of the jaws; this significantly changes the effort required by the user to actuate the input member completely to full stroke. In some configurations full stroke should not be achieved due to potential damage to the needle, therefore typical needle drivers incorporate an input ratcheting system, where the stroke of the handle can be broken up into finite segments in between ratchets to allow the user to hold the needle at various input lever locations.

Figure 8:
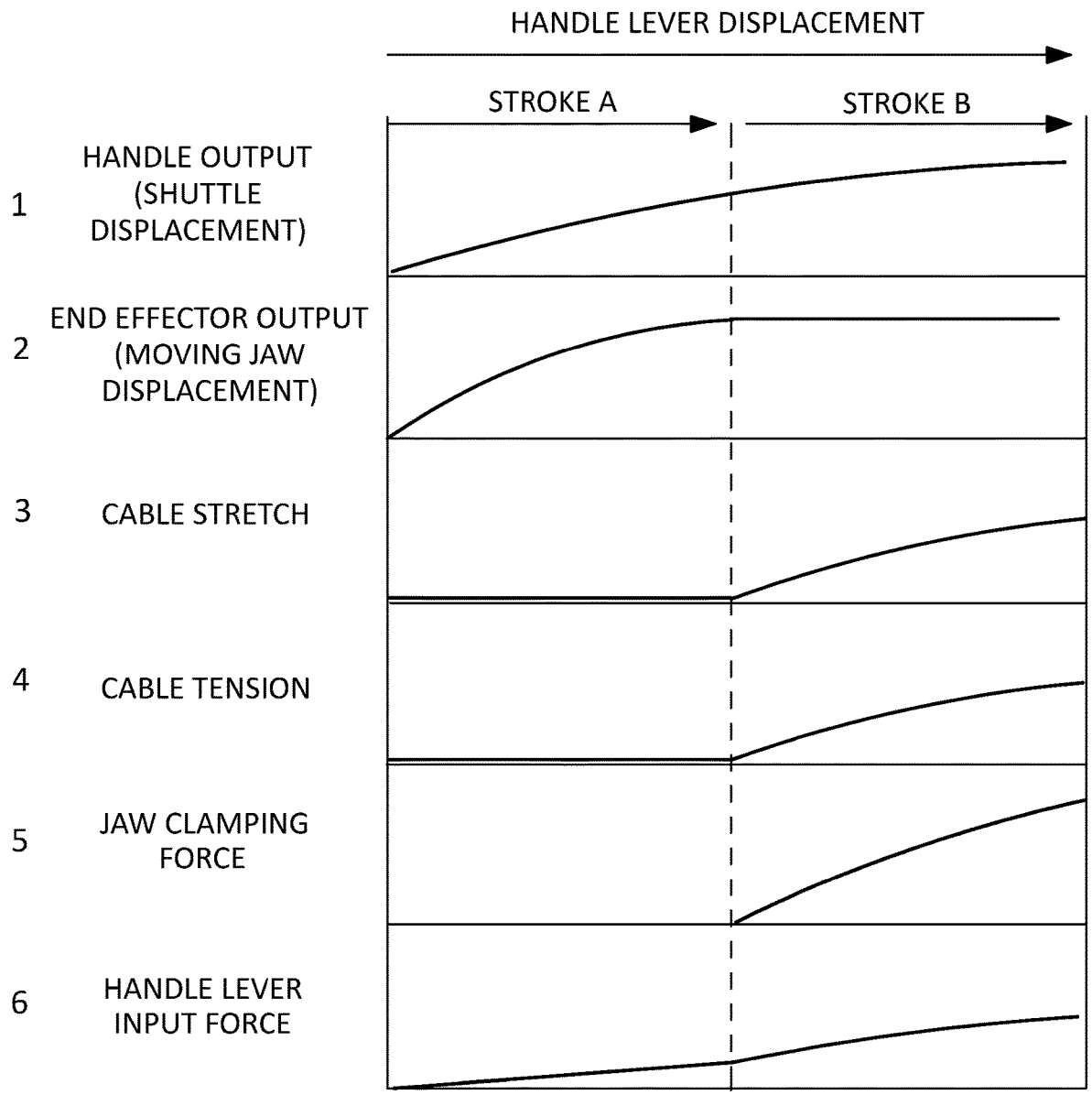
FIG. 8 shows graphs illustrating the transmission system of a needle driver's input stroke.

The use of a compliant transmission member solves these problems and eliminates the discrepancy among uses users in the amount of input used to adequately hold the needle. A compliant transmission member acts as an energy storage member so that the user can actuate the input handle lever completely without having to worry about over-driving the jaws and damaging the needle. If a large needle is placed within the mouth of the jaws, a full stroke can still be achieved at the handle input lever while in a needle driver with a stiff transmission member, full stroke would not be achievable without causing damage to the instrument or the needle. This reduces the need for a multiple ratchet system which can provide discrepancies to users on whether adequate jaw clamping force is achieved. The handle lever displacement (input stroke) can be broken up into two different phases, stoke A and stoke B. Whereas the transition from stoke A to stoke B occurs when the jaws reach a hard stop, such that stoke A is before jaw hard stop and stoke B is after the jaw hard stop. Jaw hard stop could occur at various handle lever displacements depending on the needle type, needle location or even needle presence. FIG. 8 shows various graphs that help explain what happens in the system as a fully input stroke is achieved.

Figure 9:
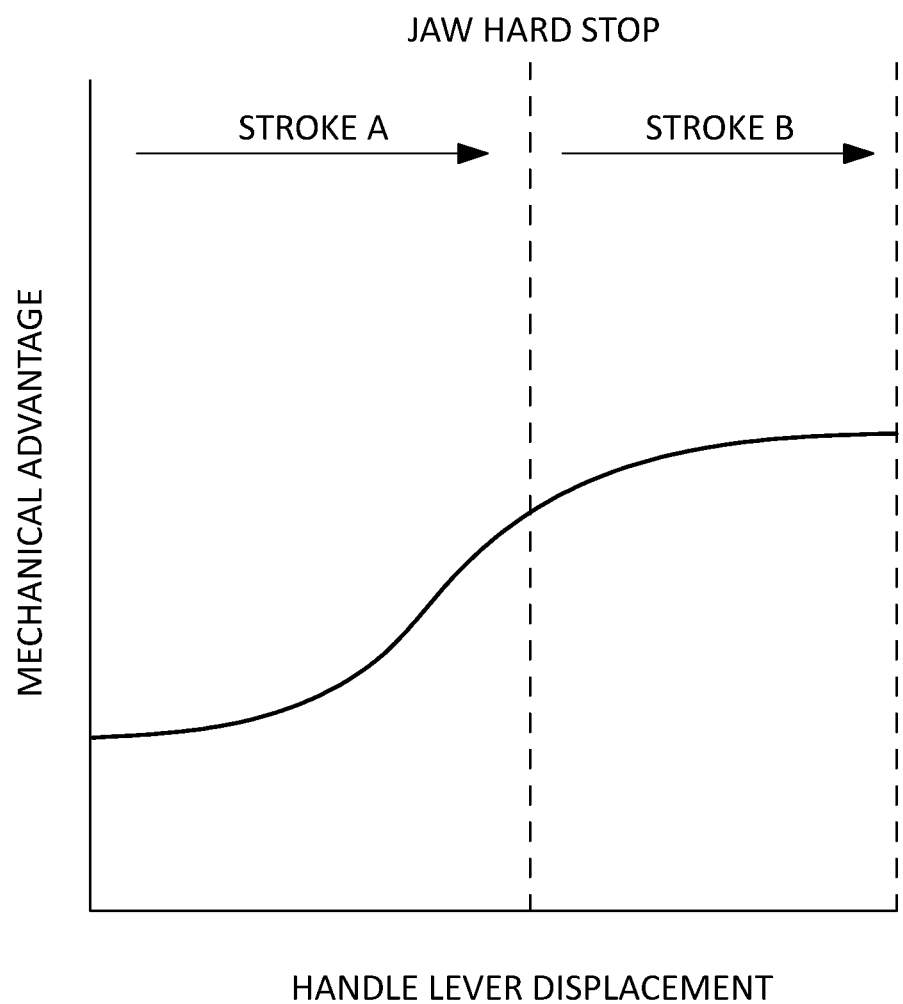
FIG. 9 shows a mechanical advantage profile for the entire system as a function of the input handle lever displacement.
Figure 10:
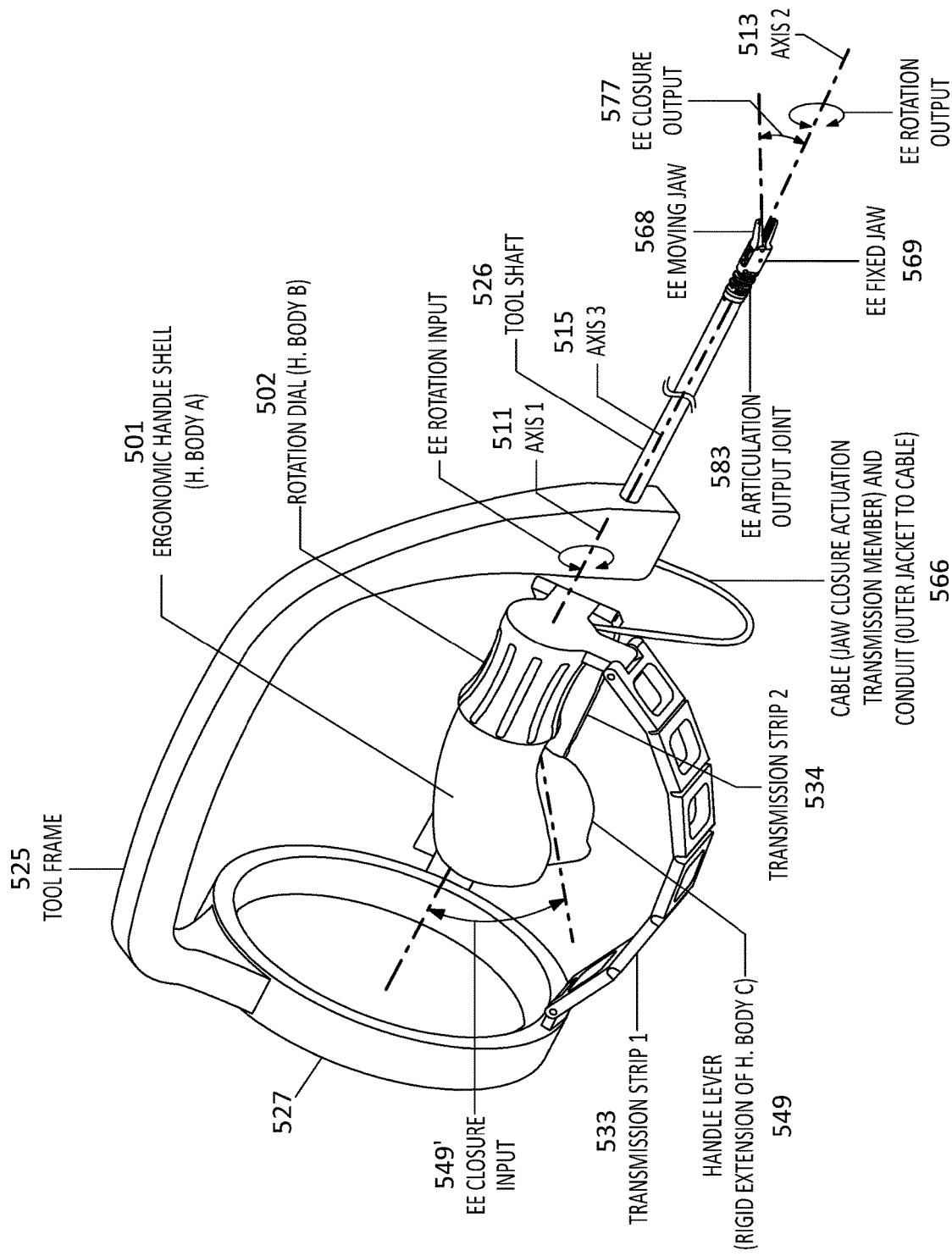
FIG. 10 illustrates one example of a medical device incorporating a jaw closure transmission system as described herein.
Figure 11:
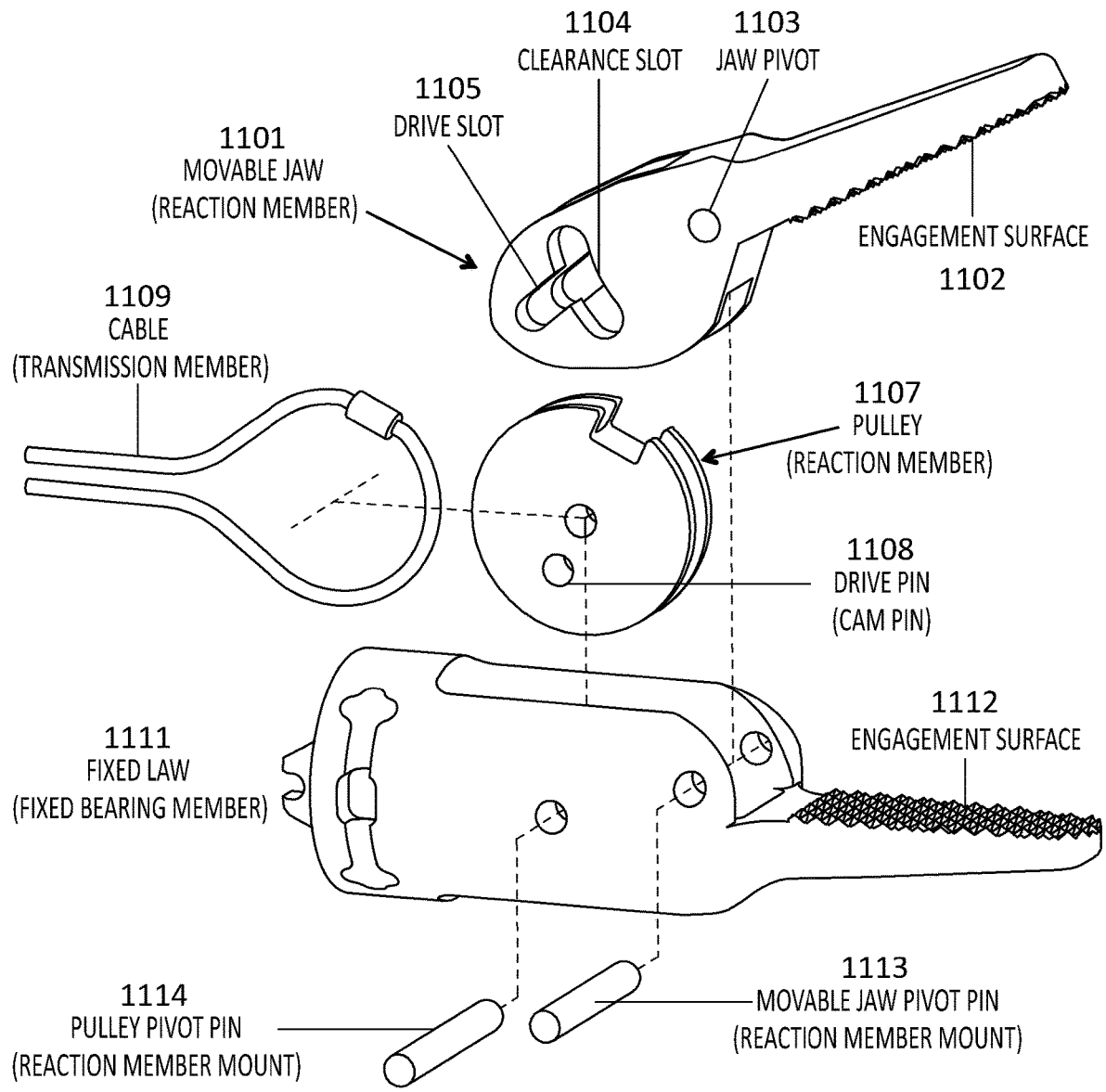
FIG. 11 shows an exploded view of an end-effector assembly.

FIG. 8, graph 1, shows the handle output; the profile of this curve is achieved through the geometry of the handle mechanism. This graph indirectly shows the mechanical advantage and the transmission ratio of the handle mechanism. This profile is extremely important as it is a non-constant mechanical advantage which consists of a low mechanical advantage at the beginning of the input stroke and then increases the mechanical advantage towards the end of the stroke. Due to ergonomic reasons (or limits), the input displacement and force at the handle varies throughout the lever stroke (through the range of angular displacement). A varying mechanical advantage in the system means that stroke A can have a completely different transmission ratio than in stroke B. During stroke A, the jaws are freely rotating in space, and therefore a high transmission ratio and low mechanical advantage can be implemented into the design during this phase which enables the jaws to achieve a wide opening angle. While in stroke B, when the jaws reach a hard stop, a higher mechanical advantage is desired such that a large clamping load at the output can ergonomically be applied from the input. This system transmission ratio comes from two sources, the handle mechanism and the jaw mechanism. The jaw mechanism which is seen in FIG. 8 graph 2, has a similar mechanical advantage and transmission ratio curve as the handle mechanism, a low mechanical advantage to start, and then a high mechanical advantage to end the stroke. However, the jaw mechanism has a different stroke than the input member. The entirety of the jaw mechanism stroke is contained within stroke A, because the transition between stroke A and stroke B happens when the jaws reach a hard stop and the mechanism thereon remains fixed providing a constant mechanical advantage for the rest of the input stroke. The profile of the system's net mechanical advantage curve is seen in FIG. 9. This profile allows the user to apply a large clamping load with very little effort at the handle while still achieving a large jaw opening angle.

In general, the apparatuses and methods described herein may apply different mechanical advantages during different portions of the input stroke to the apparatus, based at least in part on the transmission assembly (including any transmission mechanisms/members, such as cams, etc.). As used herein the term "mechanical advantage" may refer to the mechanical advantage profile, similar to that shown in FIG. 9. For example, where a first mechanical advantage during the first part of the input stroke is greater than the applied second mechanical advantage during the second part of the input stroke, the instantaneous mechanical advantage at any time during the first part of the input stroke may be greater than the instantaneous mechanical advantage at any time during the second part of the input stroke. Thus, it should be understood that the mechanical advantage does not need to be a constant, but may refer to the profile (e.g., over time), as used herein.

FIG. 8 shows the performance of the compliant transmission member (cable). Since there is no force build up in stroke A, the cable does not stretch; however in stroke B, the cable is stretched because the jaw mechanism has reached its hard stop at the distal end while the input handle mechanism is still able to produce more cable displacement as the handle input lever reaches a full displacement (full stroke). A system with a much stiffer transmission member, such a steel rod or a flexible control wire, will not perform in this manner, as displacement at the input handle would be really hard to generate because the forces would directly relate to the clamping forces on the needle. A compliant transmission member allows for a soft buildup of force at the handle over a displacement to generate the closure force required. Cable tension is shown in graph 4. During stroke A the force felt at the handle input is the handle return spring which is shown in FIG. 8 to have a linear spring constant, K. As the stroke transitions to stroke B, the handle force is now the sum of the return springs in the system and the tension in the cable, the more compliant the transmission member the less drastic the increase of input force is at the stroke A to B transition. As shown in graph 5, as the handle input lever achieves full stroke, the needle clamping force increases greatly based on the compliance of the cable and the amount of handle lever displacement left in stroke B. A transmission member that is too compliant would mean inadequate clamping load while a transmission member that is too stiff would require a ratcheting system and could damage the needle. As shown in graph 6 of FIG. 8, even as the needle clamping force increases, the handle lever input force doesn't increase as much due to the increasing high mechanical advantage of the handle mechanism and the fixed mechanical advantage of the jaw mechanism. This gradual increase in handle force while achieving optimal jaw closure eliminates the need of the multiple ratchet system that is required on needle drivers with a really stiff transmission member. The use of multiple intermediate transmission members may allow optimization of the jaw closure transmission system. As described, there are many benefits of incorporating a highly flexible cable as the transmission member. Incorporating such a transmission member into the jaw closure transmission system has many challenges, which may be overcome with additional transmission mechanisms. Additional transmission members may also make the design of input sub-system and output-system less critical and allow the transmission profile of the jaw closure system to be modified by the additional transmission mechanisms. This may, in turn, allow sub-systems configurations with improved packaging (smaller size), fewer components, and which may be less expensive to manufacture.

As will be described in greater detail below, in some variations these apparatuses may be modular. Any of the sub-systems described herein may be modular and may be interchangeably used with different components of the system. For example, a modular (e.g., multibody) system may be configurable to use various jaw closure transmission systems, which may be highly beneficial as medical device. Modular devices may allow the user to customize the performance of the jaw closure transmission system for the desired action which they are trying to perform during surgery. A customizable device also enables the use of various configurations which incorporates user preference.

As used herein a transmission mechanism refers to a different body than a transmission member. A transmission member is a single body member which is used to transfer mechanical energy between two parts (e.g., from point A to point B). Transmission members are not required to be rigid or semi rigid but could be flexible in one or more DOF. As described above, a transmission member could be a transmission cable. The transmission cable may be semi-compliant in the axial direction and highly flexible in bending. Transmission members may be utilized along the transmission path of the system to transmit the displacement and/or force from one part to another which could be aided by transmission guides which may be used to route the transmission members throughout the device from an input sub-assembly to an output sub-assembly.

A transmission mechanism may be a multi-body member which may or may not be used to intentionally modify the transmission ratio/mechanical advantage of the input to the output. Transmission mechanisms described herein may be included in the input sub-system and/or in the output sub-system, and/or between the input and output sub-assemblies. While shown in the input sub-system, the transmission mechanism may be referred to as a handle mechanism or handle transmission mechanism; these terms may be used to describe the location of the transmission mechanism within the system. A transmission mechanism may include a body member and one or more transmission guides which are used to route the transmission of forces throughout the assembly. A transmission mechanism may also include an input member, and an output member (transmission input member and transmission output member). The input and outputs of a transmission mechanism may alternatively or additionally include input or output members such as levers, buttons, knobs, or jaws. For example, an input sub-system configured as a handle assembly may include a transmission mechanism to modify the transmission ratio of the system, and the input of the handle assembly may be an input member (e.g., handle lever) which takes the input of the user as the input to the transmission mechanism and the output of the transmission system is the shuttle which is linearly constrained, and which linearly translates within the handle and or dial.

An input sub-system and an output sub-system may include a transmission mechanism, however these sub-systems are not required to contain a transmission mechanism but could instead include multiple transmission members and transmission guides to route the input to the output of the sub-system. The term transmission mechanism could be used to describe the mechanism within an input sub-system and an output sub-system, but not all sub-systems are required to include transmission mechanisms.

Figure 3:
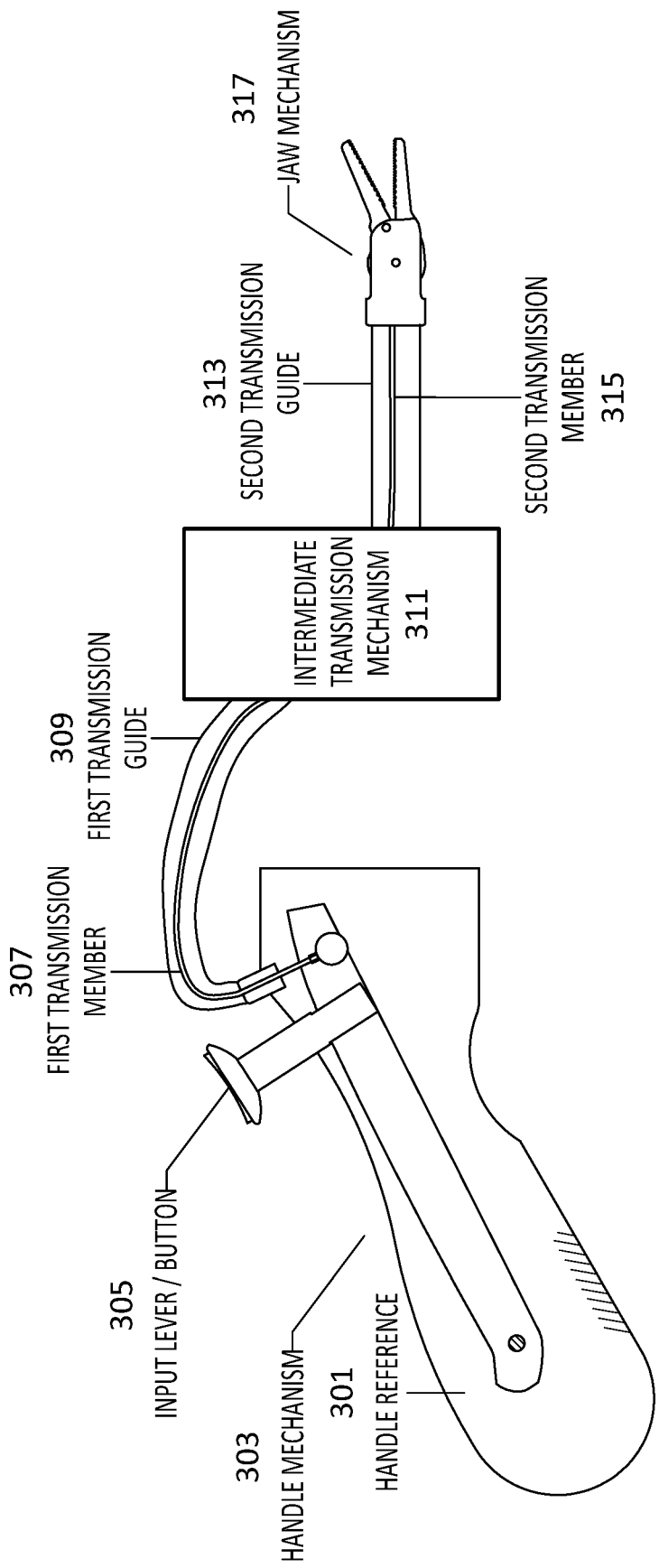
FIG. 3 is another diagram showing an example of a jaw closure transmission system with an intermediate transmission mechanism incorporated into the jaw closure transmission system.
Figure 3B:
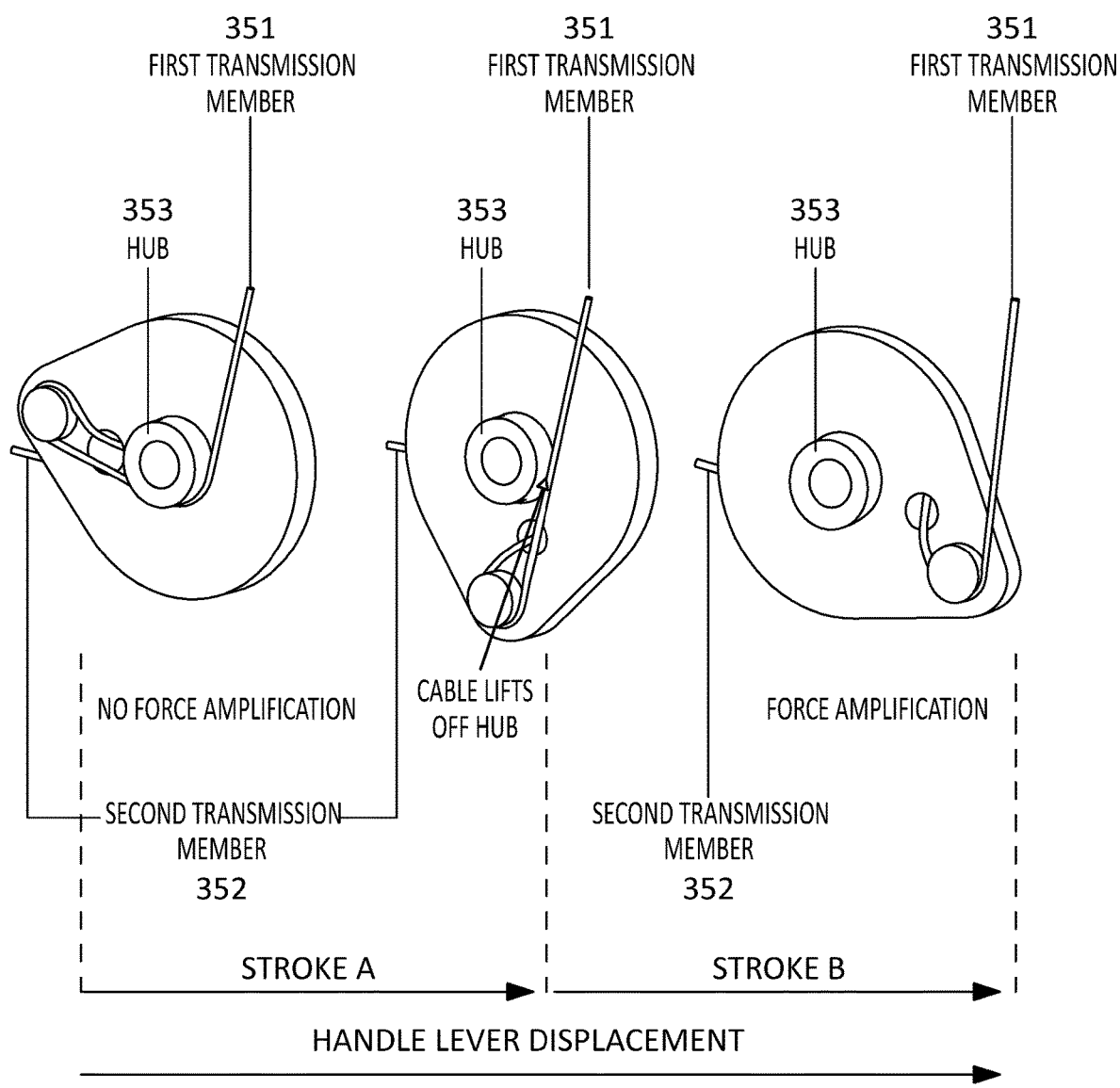
FIG. 3B shows an embodiment of an intermediate transmission cam used to create a force amplification from the first transmission member 351 to the second transmission member 352.
Figure 3C:
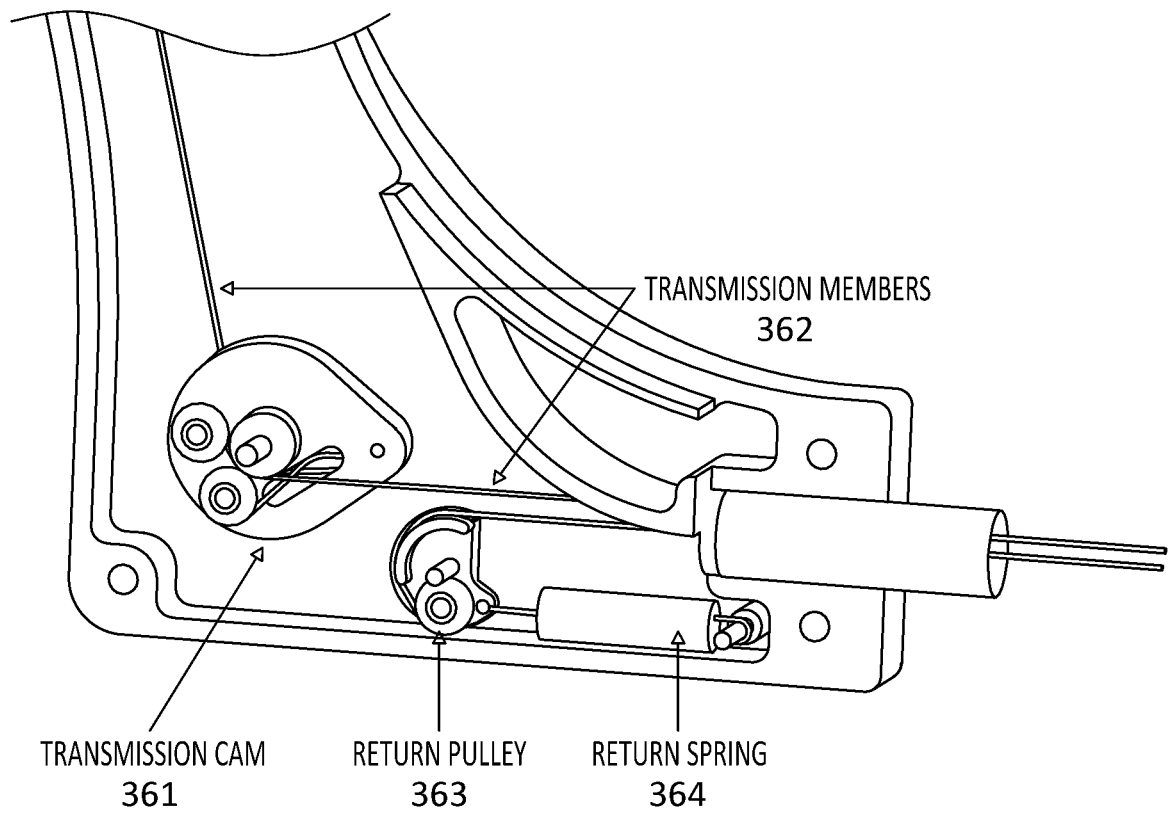
FIG. 3C shows an embodiment of an intermediate transmission mechanism located inside a device/tool.

For example, FIG. 3 shows an example of a device including an intermediate transmission (intermediate transmission mechanism). FIG. 3B shows one example of an intermediate transmission including a cam with a transmission member serving as an input and an output to the mechanism. When transmission members interact with the transmission mechanism, they may be considered part of the transmission mechanism.

Figure 16:
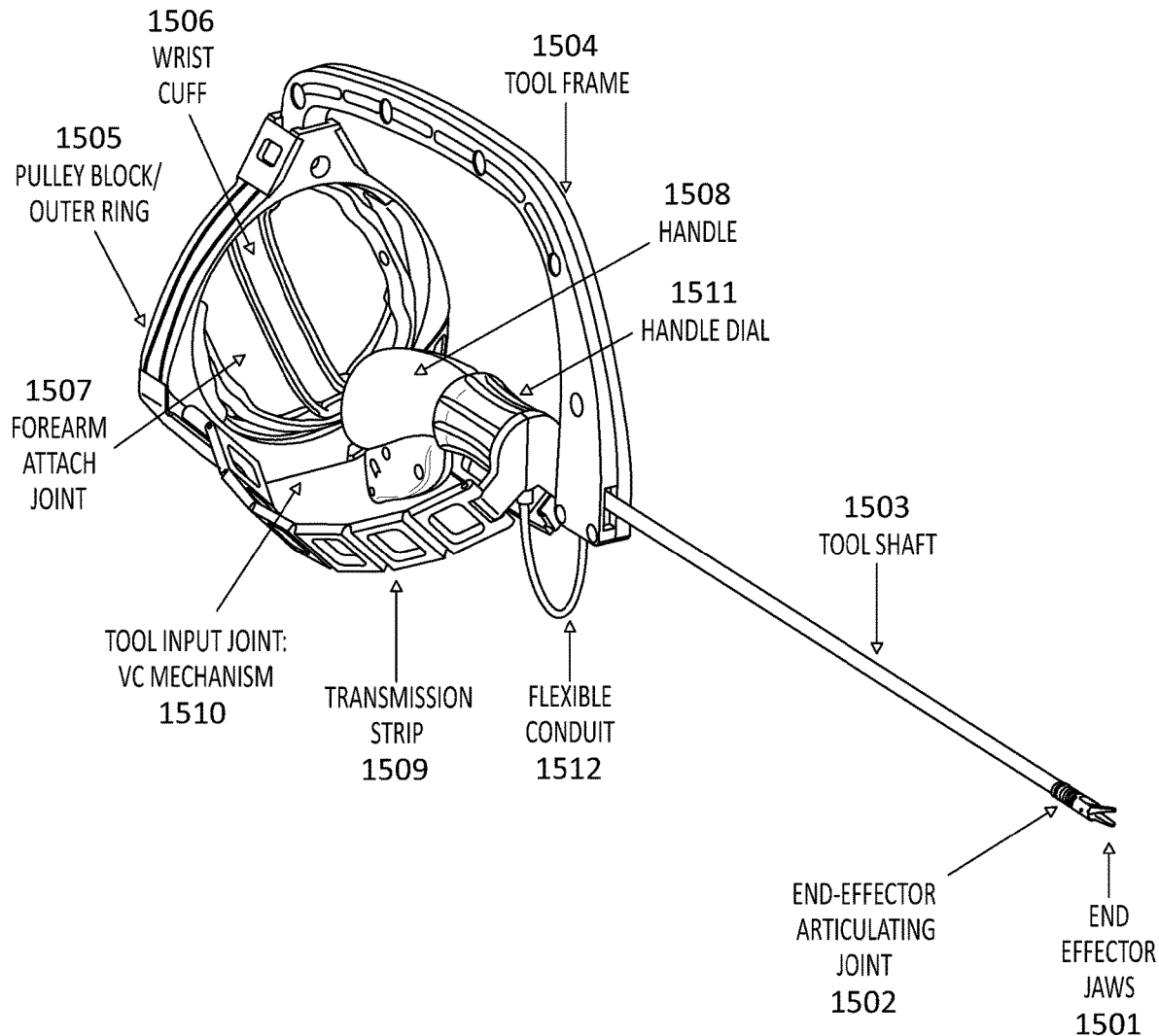
FIG. 16 shows an embodiment of a minimally invasive surgical device that incorporates a jaw closure transmission system as described here.

When describing the input stroke of an input sub-assembly, the position of the jaws may be different depending on when the split in the input stroke occurs. For example, the split in the input stroke (e.g., between a first portion of the input stroke and a second portion of the input stroke) may occur when the jaws reach a stop location in which there is no longer any movement of the output sub-assembly for a unit of input movement at the input sub-assembly. In order for there to be no movement of the output sub-assembly, which in the example, shown in FIG. 16 is the jaw assembly, the jaws are in contact with each other, which is considered fully closed. Alternatively, the jaws could be in contact with a needle or tissue (or other object or material held between the jaws. For example, when the jaws grasp a needle or tissue, they reach a full stopped position because there is no additional movement of the jaws when additional stroke is generated at the input sub-assembly. The location of the jaws when they reach this hard stop may vary depending on the size of the material or needle between the jaws. If a larger diameter needle (as shown in FIGS. 5-6) is used in surgery the jaws would reach a hard stop before they would if a smaller needle were used in surgery. The location of the needle may also determine the location the jaws when the jaws reach the hard stop in the jaw configurations described herein. Since the jaws may rotate about a jaw pivot pin, as shown in FIGS. 12A and 12B, the closer the needle is to the pivot, the sooner the jaws will reach the defined hard stop. This same principle applies to the jaws when grasping tissue or other material, when larger tissues are grasped at the proximal end of the engagement surfaces the jaw will reach a hard stop sooner. When the jaws reach a hard stop, the mechanical advantage in the jaw mechanism no longer changes with additional input stroke at the input sub-system.

The transmission system may be been described in three parts: an input sub-system, a transmission sub-system, and an output sub-system. The transmission sub-system described may include a combination of the transmission members and transmission guides. FIG. 3 shows one example of a transmission sub-system including one intermediate mechanism 311. A transmission sub-system can include a plurality of intermediate transmission mechanisms and members. A simplified version of the transmission system in FIG. 3 can be represented by the block diagram FIG. 17.

Figure 17:
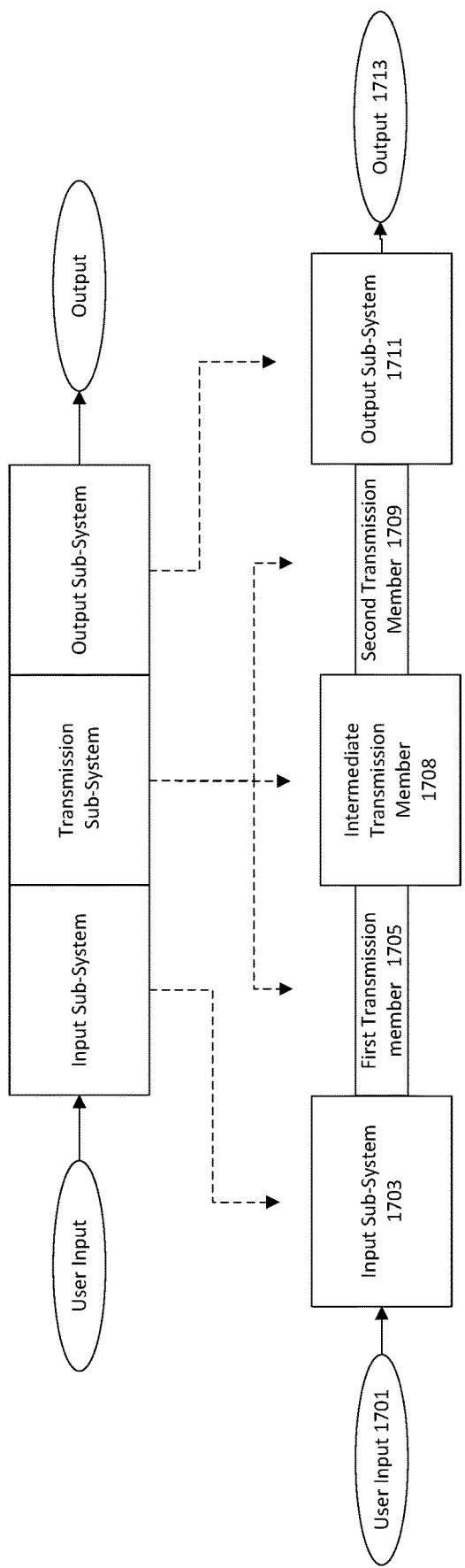
FIG. 17 shows a block diagram illustrating the interaction between sub-systems within a jaw closure transmission system at a high level and the illustrating how the transmission sub-system can consist of one or more intermediate transmission mechanism in additional to transmission members.

In FIG. 17, an input sub-system 1703 (e.g., a handle mechanism) receives an input 1701, e.g., from a user activation, and the output of the input sub-system is connected to a first transmission member 1705. The first transmission member serves as the input to the intermediate transmission member 1708 (intermediate transmission mechanism) which outputs to the second transmission member 1709. The second transmission member serves as the input to the output sub-system 1711, while the output 1713 of the output sub-system maybe, e.g., a jaw motion and resulting clamping force produced at the jaws.

Figure 18:
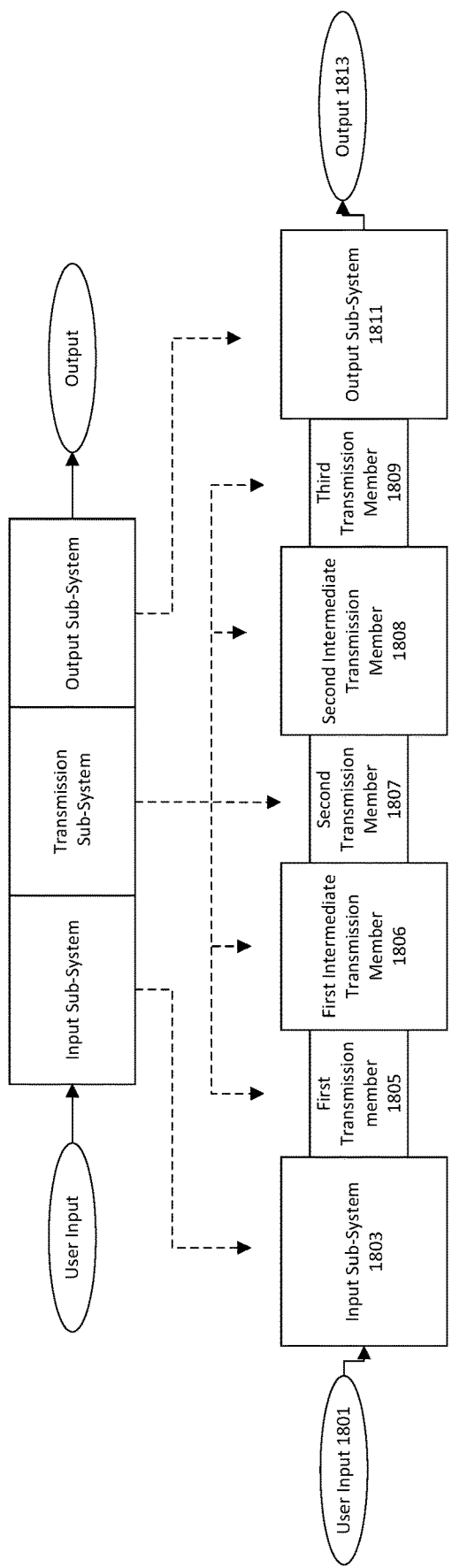
FIG. 18 shows an example of a block diagram illustrating sub-systems within a jaw closure transmission system at a high level, similar to that shown in FIG. 17, but illustrating a transmission sub-system with multiple transmission mechanisms (intermediate transmissions).

A transmission system may include more than one intermediate transmission mechanism within the transmission sub-system. In some examples multiple intermediate transmission mechanisms between the input and the output sub-system may be included, as shown by the diagram in FIG. 18, showing a first intermediate transmission member 1806 and a second intermediate transmission member 1808, connected by a second transmission member 1807. The user input 1801 is provided into the input sub-system 1803, which is input into the first intermediate transmission member 1806. The output of the second intermediate transmission member 1808 is transmitted by the third transmission member 1809 to the output sub-system 1811 and output (e.g., jaw movement) 1813.

Figure 19:
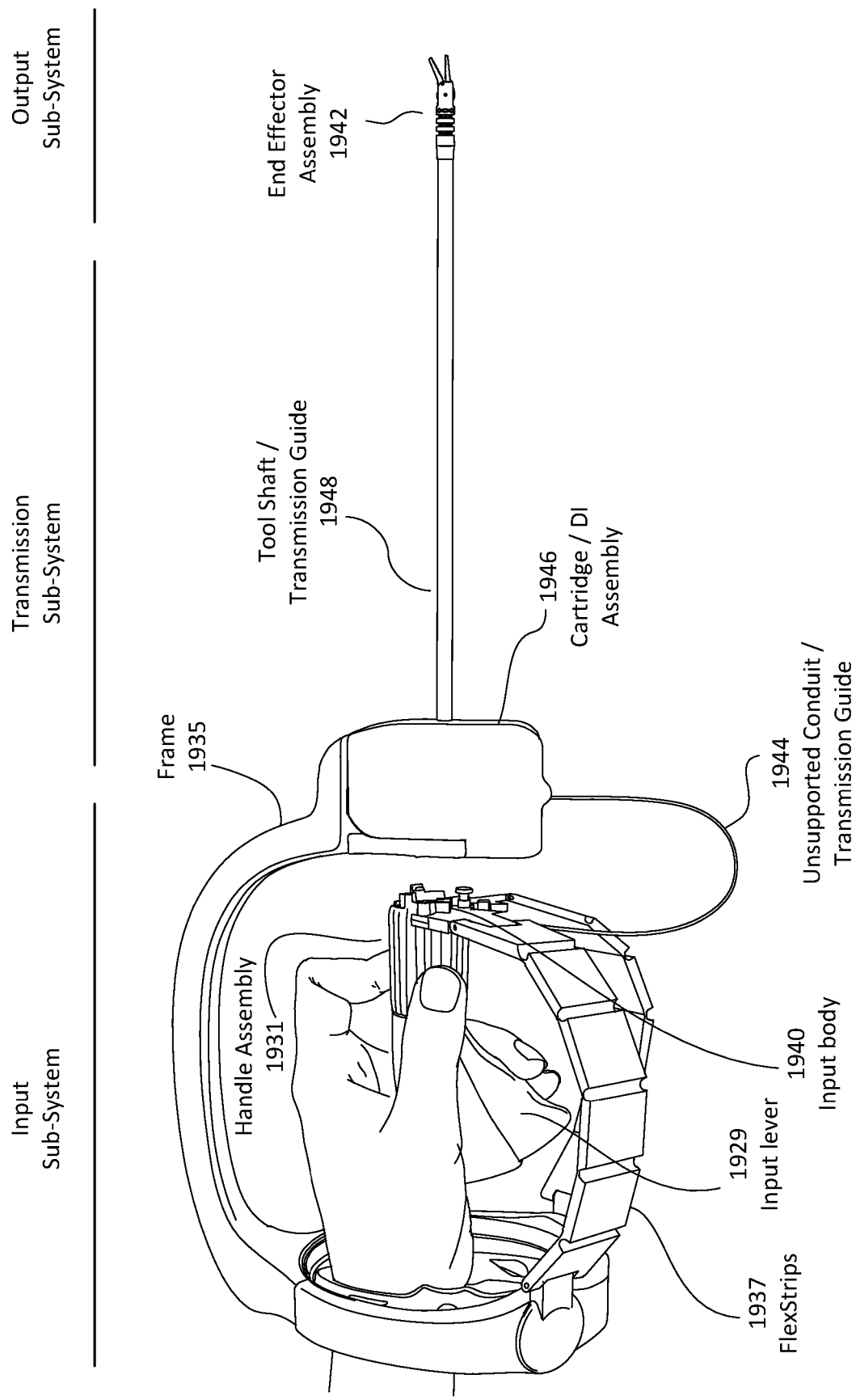
FIG. 19 shows another embodiment of a minimally invasive surgical device (similar to that shown in FIGS. 15 and 16) that incorporates a jaw closure transmission system as described here.

The addition of intermediate transmission mechanisms to the transmission system allows the transmission ratio to be finely tuned to an optimal performance. The jaw closure transmission systems described herein may be integrated into any appropriate apparatus, such as in a parallel kinematic articulation joint in which the jaw closure traverses to the frame via unsupporting conduit transmission member routes through a flexible transmission guide (as shown, e.g., in U.S. Pat. No. 8,668,702). For example, any of these embodiments may be configured as a medical device, such as shown in FIG. 19. FIG. 19 shows an example of a minimally invasive surgical device that incorporates a jaw closure transmission system such as that shown in FIGS. 15 and 16. In FIG. 19, axial compression in the transmission guide may be undesirable and could result in an inefficiency in the transmission system because the input to the output sub-system may be considerably less than the output of the input sub-system. To eliminate this inefficiency caused by the transmission guide, the transmission guide may be made rigid axially and in bending. However, it may be desirable to provide a transmission guide that is flexible in bending and has some compliance in the axial direction. To reduce axial compression and/or inefficiencies which could be caused by friction between the transmission member and any transmission guides, an intermediate transmission member may be included, as shown in FIG. 3. This transmission mechanism may be used to modify the transmission ratio of the system for instance, if the intermediate transmission mechanisms increases the mechanical advantage of the system, the first transmission member serving as an input may have more displacement and less force (tension or compression) at every finite point than the second transmission member which is the output of the intermediate transmission mechanism. By lowering the tension in the first transmission member we can reduce the impact of axial compliance of the first transmission guide and or first transmission member and create a more efficient system. Using additional transmission mechanisms can further alter the transmission profile of each transmission member allowing the desired amount of force to be transferred through each member, allowing the design of each transmission member to not be limited based on the overall transmission ratio of the system.

In FIG. 19, the device includes an input sub-system (configured as a handle assembly 1931 coupled to a frame 1935 via a pair of flex strips that may articulate the end effector assembly 1942. The transmission sub-system and the output sub-system in this example form a device that also includes an input assembly including an input member (not visible) and input body 1940. The input body couples to the handle assembly 1931 so that the input member engages a handle lever 1929, through one or more linkages within the handle assembly. The frame couples to a cartridge assembly 1946. A transmission cable connects between the input member and the end effector, passing through the unsupporting conduit 1944 and the transmission guide (tool shaft 1948). The cartridge assembly may be configured as an intermediate transmission mechanism.

Figure 15:
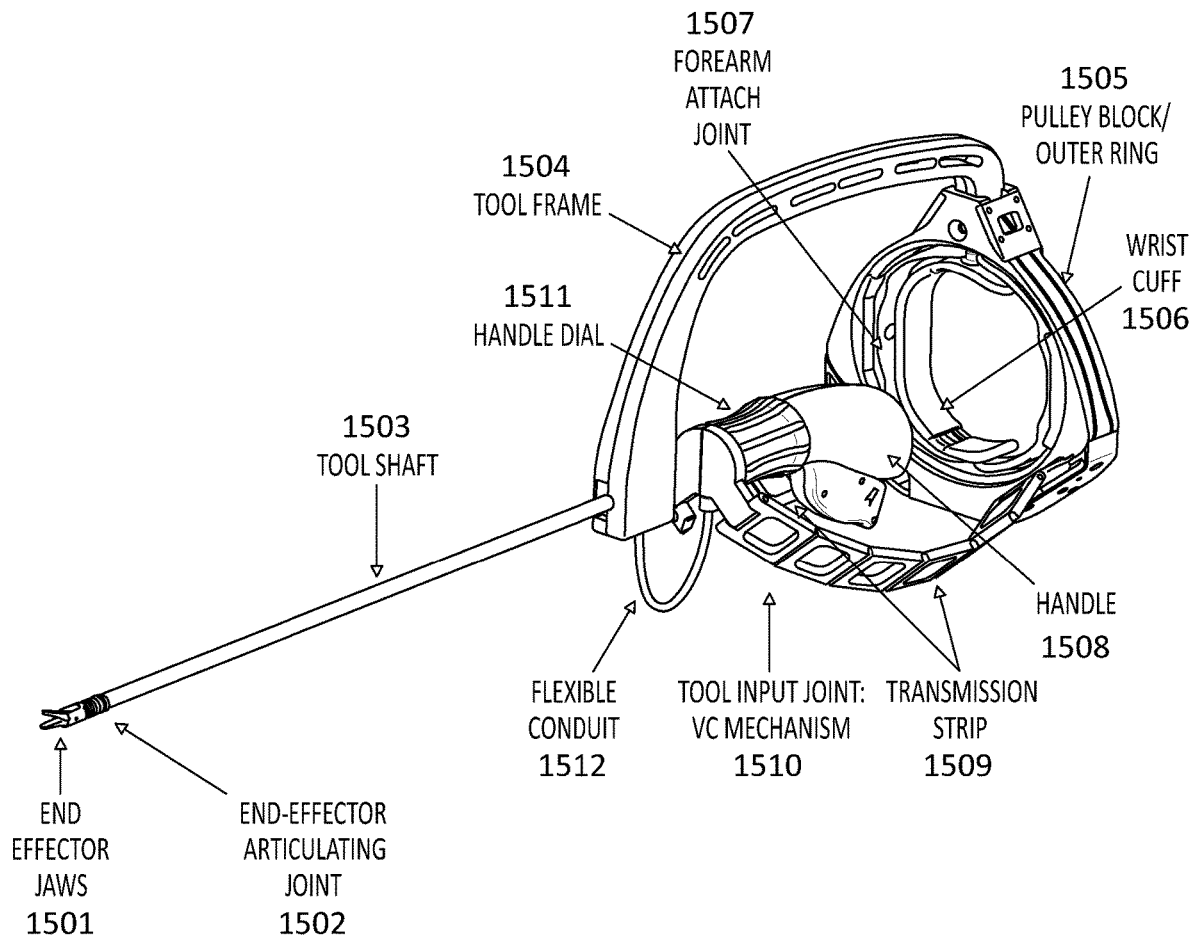
FIG. 15 shows an embodiment of a minimally invasive surgical device that incorporates a jaw closure transmission system as described here. The device includes end-effector jaws 1501, end effector articulating joint 1502, tool shaft 1503, tool frame 1504 (including outer ring 1505), wrist cuff 1506, forearm attach joint 1507, handle 1508, handle dial 1511, transmission strip(s) 1509, tool input joint 1510 and flexible conduit 1512.
Figure 24:
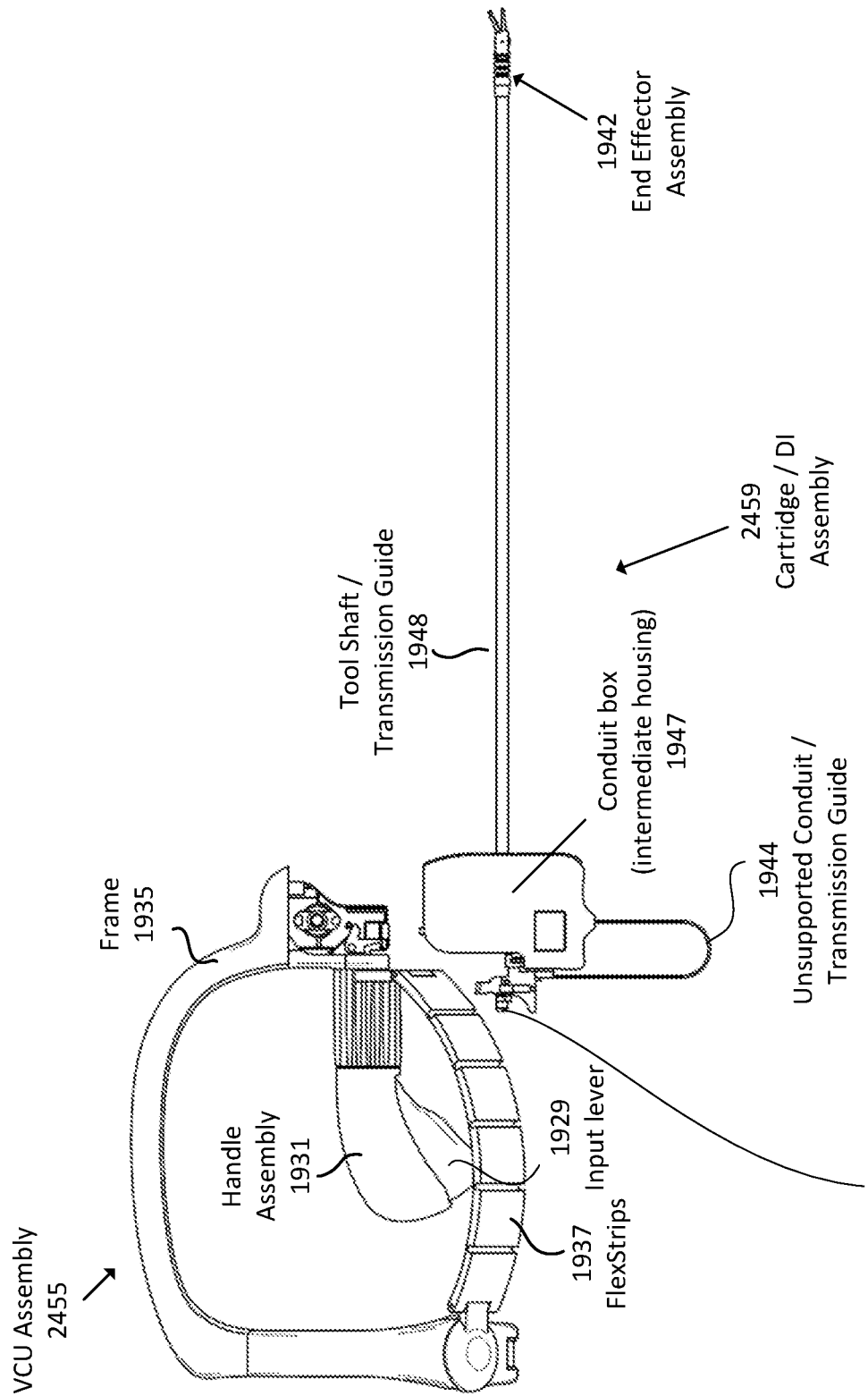
FIG. 24 shows an example of a minimally invasive surgical device (similar to that shown in FIG. 18, above) that is separated into to assemblies that may be coupled together.

In FIG. 19, the device is shown coupled to a handle assembly to form an integrated input assembly (sub-assembly). In some variations, as shown in FIGS. 15-16, described above, the handle assembly may be integrated with the input assembly; in some variations the handle sub-assembly may be separated from the rest of the input assembly. For example, the input assembly may be separated from the handle sub-assembly as shown in FIG. 24. In this example, the input member 2404 is visible, and the handle assembly ("VCU assembly") 2455 is separate from the device ("cartridge" 2459). In this example, the input member is a crimp that may couple to, e.g., a handle output.

Figure 20:
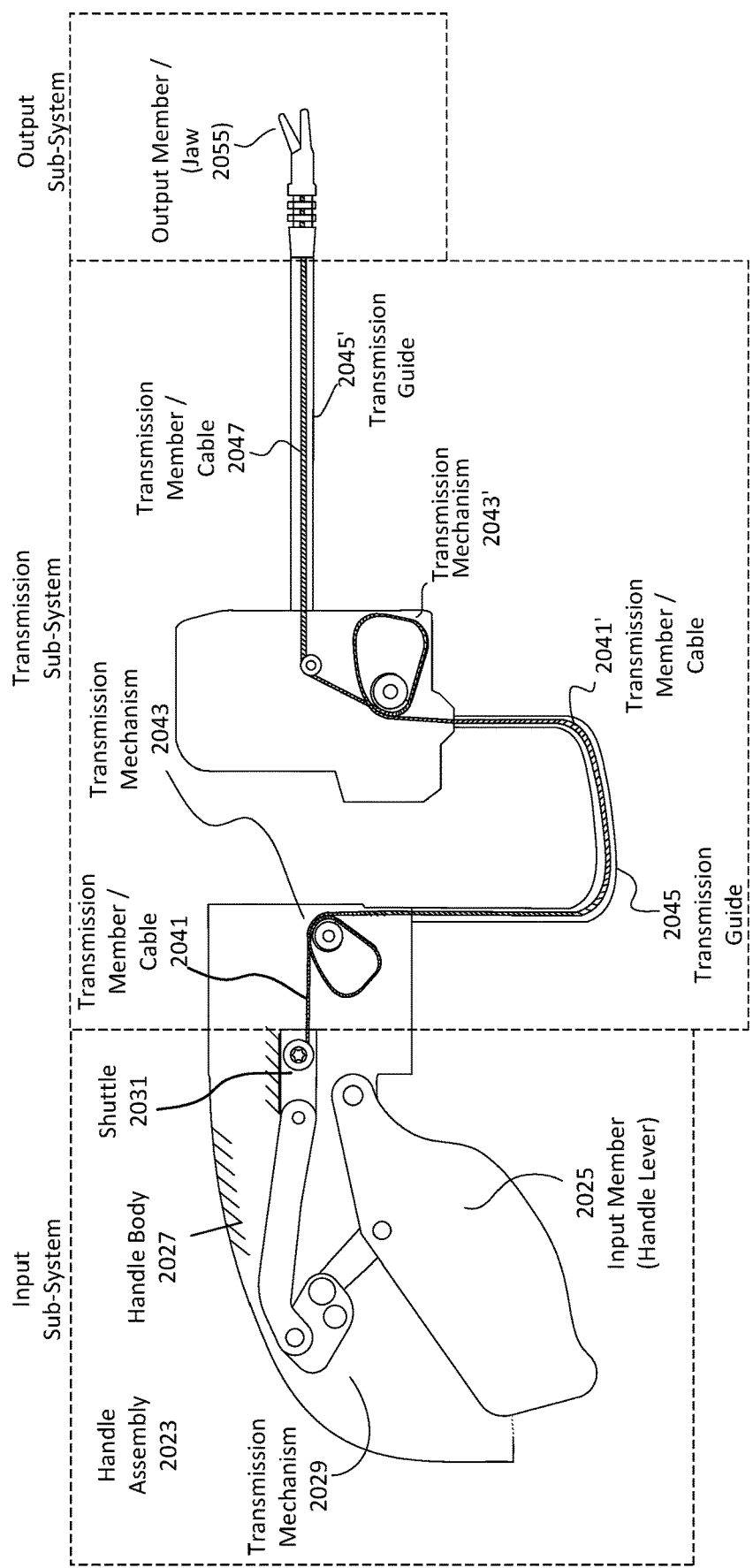
FIG. 20 illustrates another example of a minimally invasive surgical device in which sections (sub-systems) of the jaw closure transmission system are described.

FIG. 20 shows an example of a system with multiple intermediate transmission members, in which the input stroke to the input sub-system is limited by the ergonomics of the user but the input force can be considerably higher than average by having an input lever which is actuated by a power gripping motion of the human hand in which the maximum gripping force generated is greater than the gripping force of a pinch grip or similar grip. The output of the input sub-system would result in a high force and smaller displacement, which may be desired as an input to the output sub-system, however the structure of the device described previously may not be capable of transferring the high forces efficiently. To transfer the mechanical energy from the input to the output, the stroke at the first transmission member is converted from high force and low displacement to low force and high displacement by a first intermediate transmission with a low mechanical advantage or conversely a high transmission ratio. The lower force and high displacement of the second transmission member routes through a transmission guide and is then converted back to high force & low displacement with a second intermediate transmission mechanism before serving as an input to the output sub-system via third transmission member.

In FIG. 20, the example includes a handle assembly 2023 with an input lever (handle lever 2025), an input body (handle body 2027) a transmission mechanism 2029, and a shuttle 2031. The transmission sub-assembly includes a transmission cable 2041, 2041' (having) and two or more transmission mechanisms 2043, 2043'. The transmission may be housed within a flexible guide 2045 or a rigid guide 2045', or both (e.g., over different regions). The output assembly (output sub-system in FIG. 20 includes an output member (jaw 2055).

Figure 23:
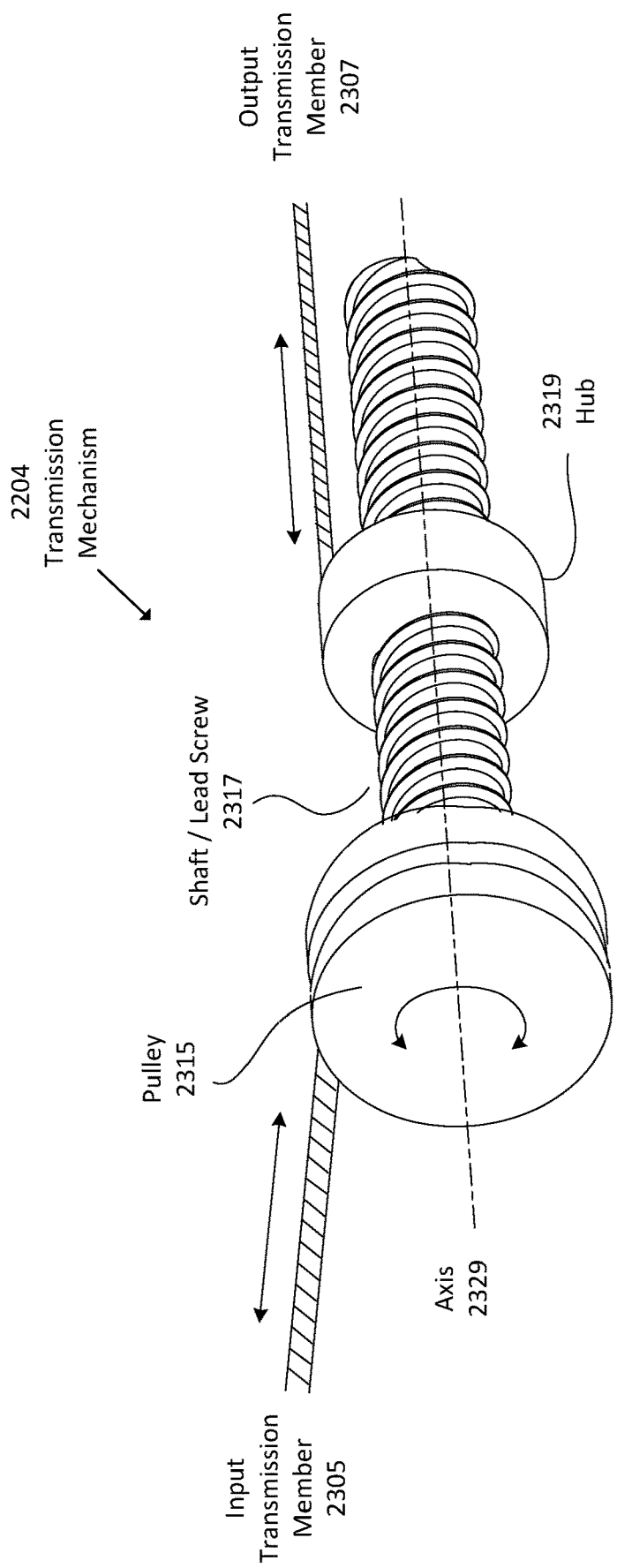
FIG. 23 shows an example of a transmission mechanism which incorporates a lead screw to drive the output transmission member which is connected to the hub of the lead screw.

FIGS. 21A-21C illustrate examples of transmission mechanisms. These transmission mechanisms may be part of an intermediate transmission mechanism, as described above. The interaction between the input and output transmission members with an example of an intermediate transmission mechanism is illustrate in FIGS. 21A-21C. In this example, the intermediate transmission mechanism includes a transmission cam, however an intermediate transmission mechanism is not limited to a cam 2103. In FIGS. 21A-21C, an input transmission member (transmission cable 2107) passes over the cam surface and exits as an output transmission member 2105. As this transmission cable is pulled, the stoke mechanical advantage changes, as shown by the arrow along the bottom of the figures. The transmission mechanism 2204 may include a lever, a four-bar linkage, a cam slot, a gear, etc. Examples of these are shown in FIGS. 22A-22F and 23, however intermediate transmission mechanisms are not limited to the mechanisms shown in FIGS. 22A-22F, or FIG. 23. For example, FIG. 23 shows a transmission mechanism configured as a pulley and screw mechanism including a pulley 2315 that receives input from the input transmission member 2305 and rotates along the axis 2329 of a threaded shaft (e.g., lead screw) 2317 on which a hub 2319 that is coupled to an output transmission member 2307 may travel.

Embodiments of transmission system may be modular, a described above, and may include one assembly or more than one that may be modularly connected. For example, FIG. 24 shows an embodiment of a modular device. Within this device, the jaw closure transmission system may be removably coupled with a handle sub-assembly so that the handle sub-assembly combines with the portion of the input assembly (input member and input body) already on the cartridge 2459. Alternatively jaw sub-systems (e.g., jaw assemblies such as shown in FIGS. 31A-31B and 32A-32G) may be swapped in/out of the apparatuses. Similarly, alternative handles may be used. In FIG. 24, the handle assembly 2455 may include a handle body to which the input body may rigidly couple, and the input member may couple with the input lever 1929, e.g., through one or more linkages (not visible in FIG. 24). In this example, the distal assembly is referenced as the cartridge or Detachable Instrument (DI) 2459. The terms cartridge and DI are used interchangeably throughout this disclosure. Within this embodiment the handle (VCU) assembly forms part of the input sub-system of the jaw closure transmission system when combined with the input assembly of the cartridge. The input assembly and/or handle assembly may include a transmission mechanism (e.g., a handle mechanism) which may receive user input. The output of the handle mechanism may be a translating transmission member, e.g., a shuttle (handle shuttle) as described above that is located within the handle assembly. The handle shuttle may be a transmission member which interfaces with the input of the cartridge. The output of the VCU is not limited to a translating member but may be a rotary transmission member which interfaces with the cartridge. The cartridge in this embodiment contains the output sub-system as well as the transmission sub-system. The output sub-system contains a transmission mechanism whose output interfaces with the environment which may consist of but not limited to ancillary devices such as but not limited to needles or mesh the output may also interface with but not limited to the patient while in use. The transmission sub-system within the cartridge also may or may not contain an intermediate transmission mechanism and a series of transmission guides which route the transmission member from the assembly's input to the assembly's output.

Any of the apparatuses described herein, such as the example shown in FIG. 24, may include an intermediate housing (e.g., conduit box) 1947. This intermediate housing may act as a connection between the flexible (e.g., "unsupporting conduit") transmission guide 1944 and the rigid (supporting tool shaft) transmission guide 1948. The intermediate housing may also include one or more transmission mechanisms (e.g., see, e.g., FIGS. 22A-22F and 23) that may adjust the mechanical advantage over the different portions of the stroke.

When the handle sub-assembly and the cartridge are brought together, they can be combined to form one larger assembly in which the jaw closure transmission system traverses the interface between the two assemblies and allows the user to actuate the handle lever on the VCU in order to trigger the jaws at the output of the cartridge. The user interaction to form the connection and disconnection of these two assemblies may include but not limited to a multiple step approach in which a series of buttons or levers must be activated to engage the transmission system.

Figure 25:
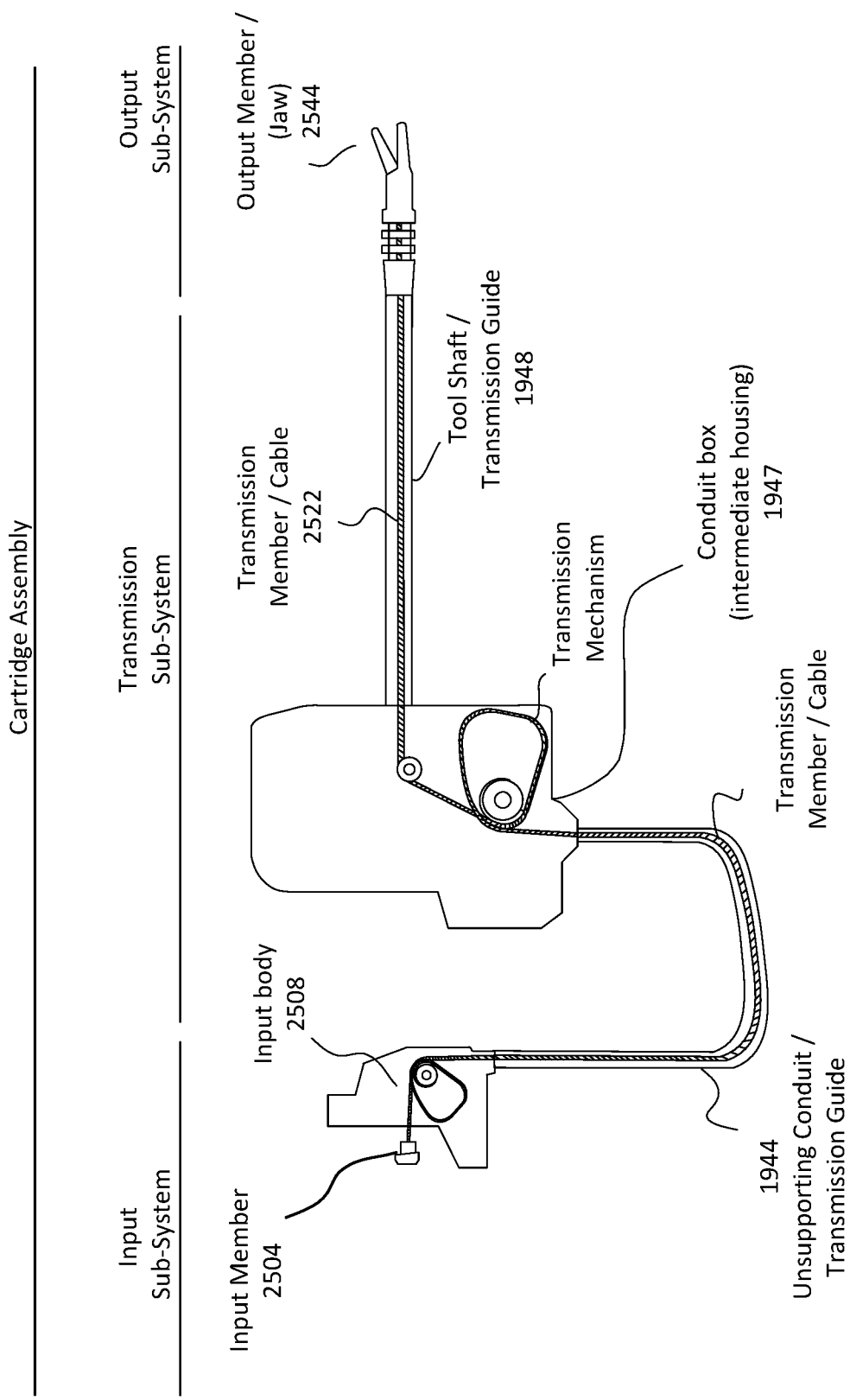
FIG. 25 illustrates an example of a cartridge assembly (such as the one shown in FIG. 24) uncoupled to the handle assembly. This example includes a jaw closure transmission system, comprising of an input sub-system, a transmission sub-system, and an output sub-system.

The transmission systems which have been defined consist of an input sub-system, transmission members and an output mechanism which may or may not include multiple intermediate transmission mechanisms. FIG. 25 shows an embodiment of a complete transmission system by these definitions is shown below in which the cartridge input member is activated by the user rather than being inserted into the VCU. In FIG. 25, the cartridge assembly includes an input assembly (input sub-system) including an input member ("input member" 2504 and an input body 2508, housing a transmission mechanism (e.g., cam). The transmission assembly (transmission sub-system) includes one or more transmission mechanisms, including an intermediate transmission, the transmission cable and one or more transmission guides, including a flexible transmission guide and a rigid transmission guide. The device also includes an output assembly including an output member (jaw).

In FIG. 25, the device is configured as a cartridge assembly ("UI") that includes the input assembly including an input member 2504 configured as part of a coupler (similar to that shown in FIG. 33A-33C), shown in FIG. 25 as a crimp, and an input body 2508. The input member may move through a stroke length relative to the input body. The input body may be configured to removably couple to a handle assembly (not shown), and the input member may couple to an output of the handle assembly (e.g., to a shuttle or linkage of the handle so that it is driven by the input, e.g., an input lever, of the handle assembly). In FIG. 25 the transmission assembly (transmission sub-system) includes a first region of transmission guide 1944 that is flexible (e.g., unsupporting) and a second region of the transmission guide 1948 that is rigid (e.g., a tool shaft). The transmission member (cable 2522) is housed within both the first and second region. An intermediate housing (conduit box) 1947 is positioned in series between the flexible and rigid regions of the transmission guide. The output assembly (output sub-system) includes a pair of jaws 2544.

Figure 26A:
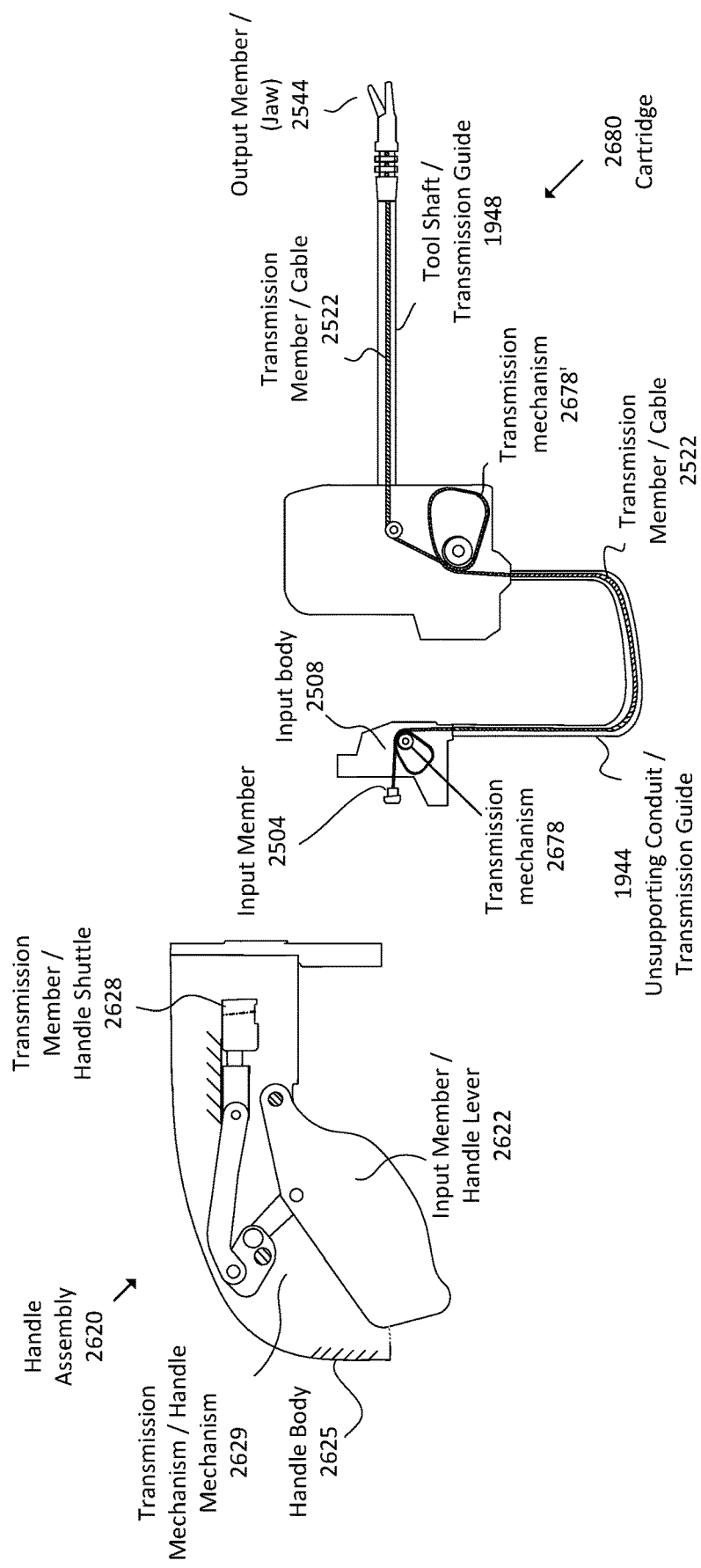
FIGS. 26A-26B illustrate one example of a minimally invasive surgical device configured to removably couple an input assembly to a handle assembly.
Figure 26B:
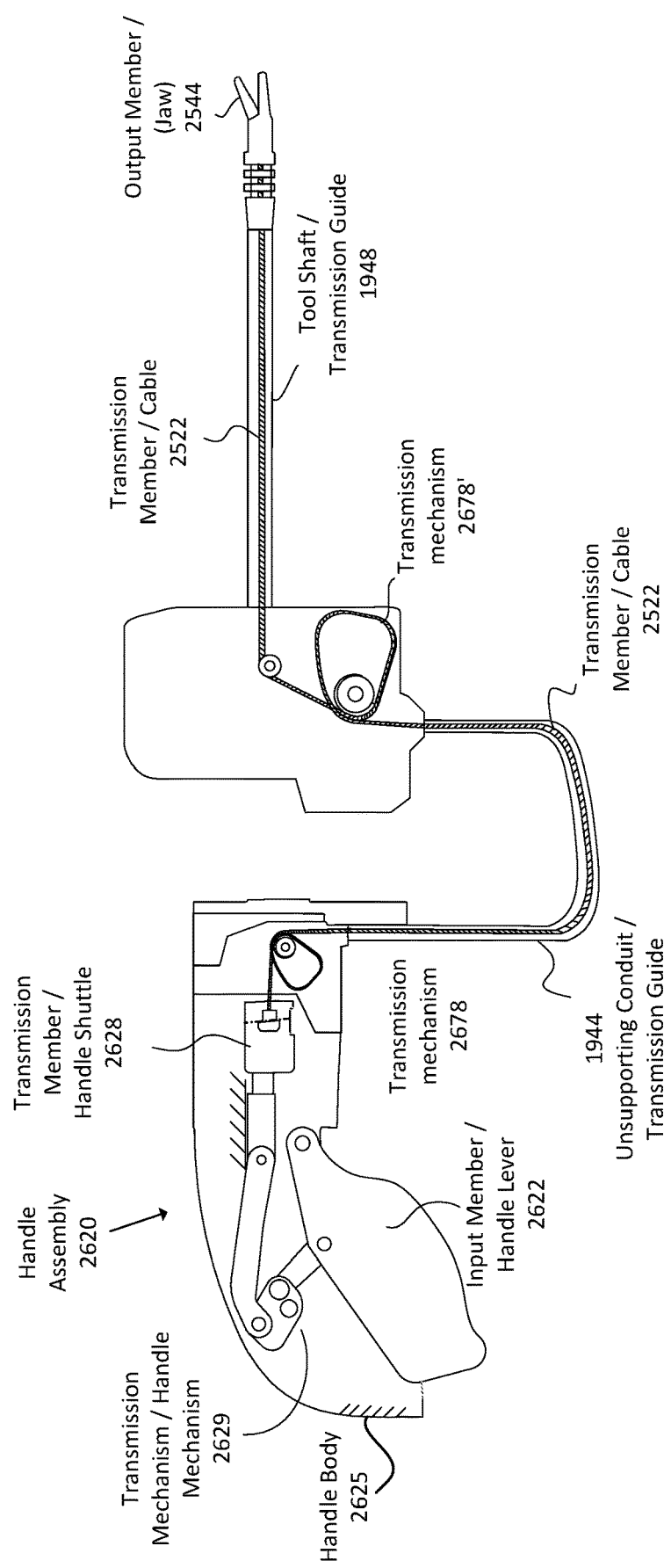

In this embodiment of the transmission system the device is fully functional, and the user can actuate the output sub-system via the input sub-system. In addition to being a complete transmission system the input sub-system is modular and configurable meaning it can be attached to another transmission member and transmission mechanism. The disassembled configuration is shown in FIG. 26A. This enables the input to the sub-system to serve as the intermediate transmission mechanism to a larger transmission system. FIG. 26B shows the input sub-system of the cartridge installed into the output of a handle assembly (this device may also include a frame, as shown in FIGS. 15-16 and 19). When installed as shown in FIG. 26B, the handle assembly becomes the new input sub-system of the jaw closure transmission system and the cartridge input becomes part of the transmission sub-system. The addition of new transmission mechanisms to a device are used to alter the transmission system profile and result in a different performance at the output sub-system. For instance, if the output sub-system requires more force than is applicable at the input sub-system an additional transmission system can be added to the jaw closure transmission system to serve as the new input sub-system. In addition to offering a different transmission profile, the new transmission member could have other benefits to the user which may consist of but is not limited to ergonomics and or additional functionality. In FIG. 26, the handle assembly 2620 includes an input member (shown as a handle lever) 2622, a handle body 2625, and a handle transmission mechanism (handle mechanism 2629), configured as a linkage, such as four-bar or six-bar linkage. The handle transmission mechanism connects the input member of the handle 2622 to an output, configured as a transmission member (handle shuttle) 2628 that may couple with the input member 2504 of the cartridge 2680, as shown in FIG. 26B. The input body houses a transmission mechanism (shown in this example as a cam 2678). As shown in FIG. 25, the cartridge also includes a transmission assembly including the transmission mechanism 2678 in the input body and a transmission mechanism 2678' in an intermediate housing that supports the first flexible transmission guide 1944 and a second stiff or rigid transmission guide 1948 through which the transmission member (cable) 2522 passes before coupling to the output member 2544 (jaw).

Figure 27:
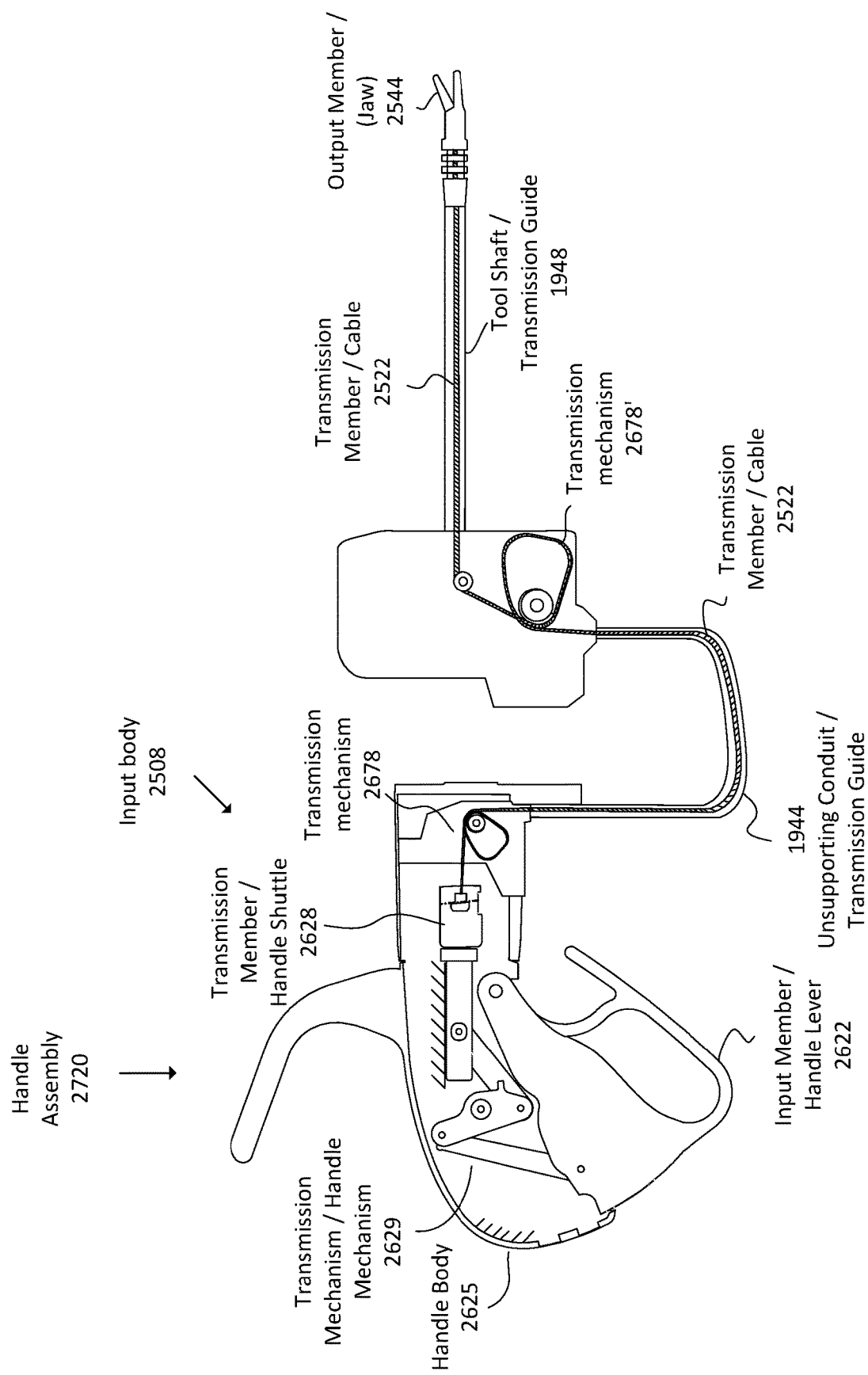
FIG. 27 shows another example, in which the cartridge device is coupled to a handle assembly; this handle assembly is different from that shown in FIGS. 26A-26B, though the cartridge device may be similar or identical, illustrating the modular jaw closure transmission system.

The modularity of the jaw closure transmission system may enable the incorporation of a platform or family of instruments which can be assembled to form different variations of the jaw closure transmission system. For example, there could be a series of handle assemblies which are compatible with the cartridge such that the user has the option to assemble jaw closure systems with different closure profiles. FIG. 27 shows a different handle assembly 2720 attached to the cartridge. The handle assembly in FIG. 27 has different handle mechanism which is capability for producing a greater displacement with a different transmission profile than the handle shown in FIGS. 26A-26B. In addition to having a different transmission profile the handle shown in FIG. 27 incorporates a new feature for user ergonomics which may be preferred by certain users.

Figure 13:
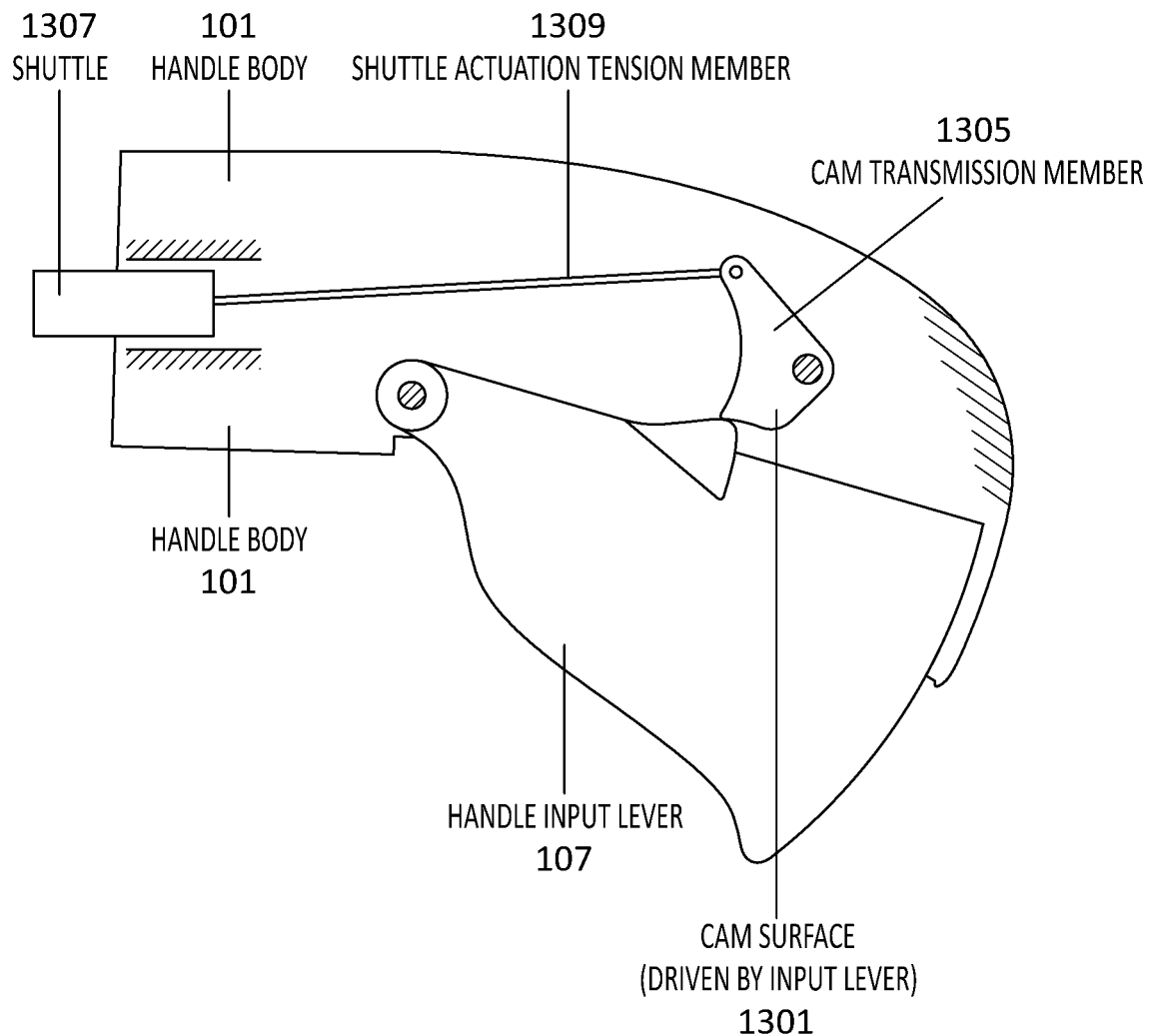
FIG. 13 shows an input sub-system comprising a cam in the handle mechanism.
Figure 14:
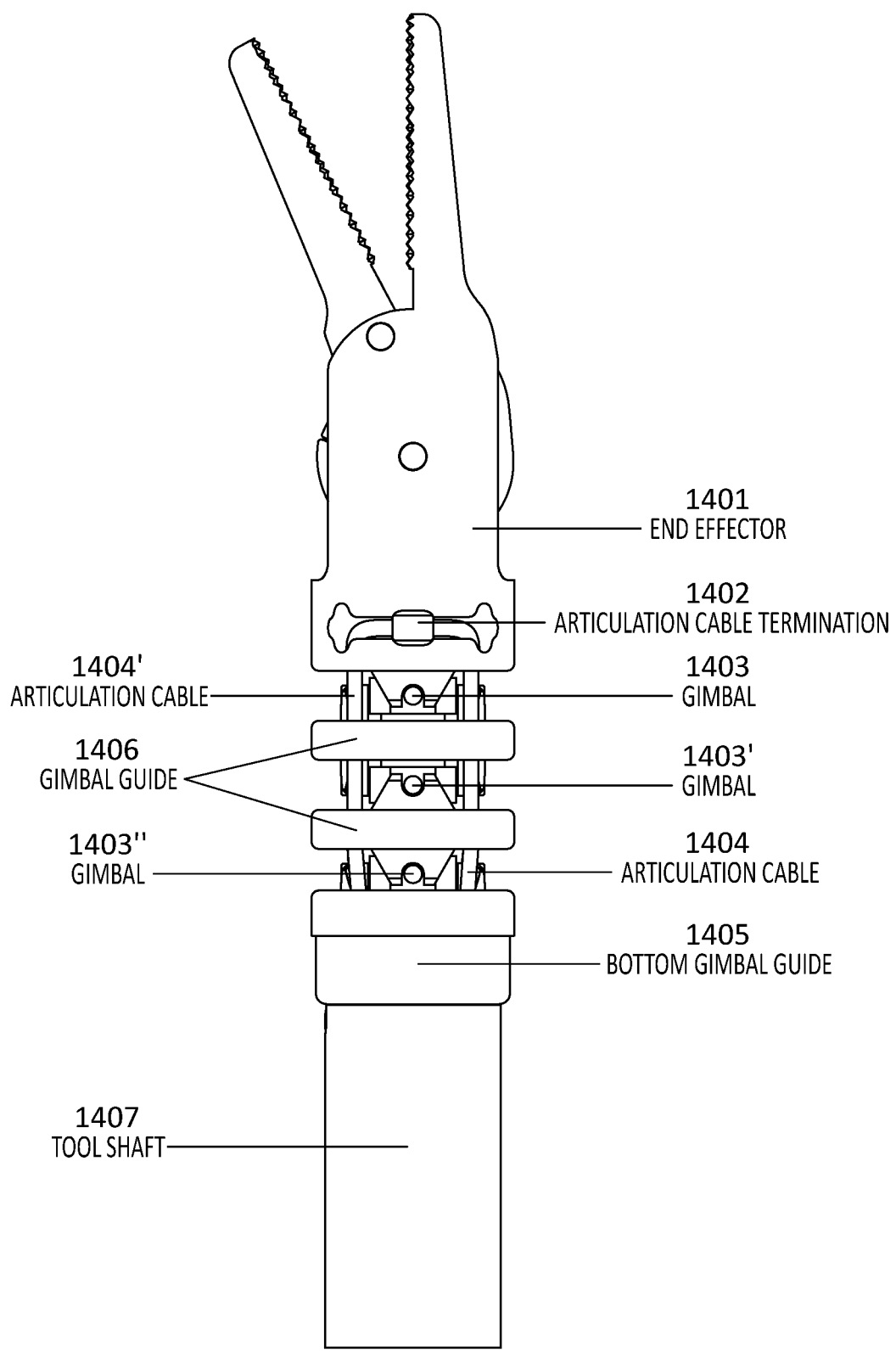
FIG. 14 shows an embodiment of an end-effector assembly including an output articulation joint (including gimbals 1403, 1403', 1403", gimbal guides 1406, articulation cables 1404, 1404', and bottom gimbal guide 1405) and including an end-effector 1401, articulation cable termination 1402, and tool shaft 1407.

Attaching a new handle assembly to the cartridge enables surgeon to optimize the device for the actions in which they are performing in surgery. FIG. 13 and FIG. 27 are additional examples of other handle assembly embodiments which output could be coupled to the input of another transmission system namely herein the cartridge.

Figure 28:
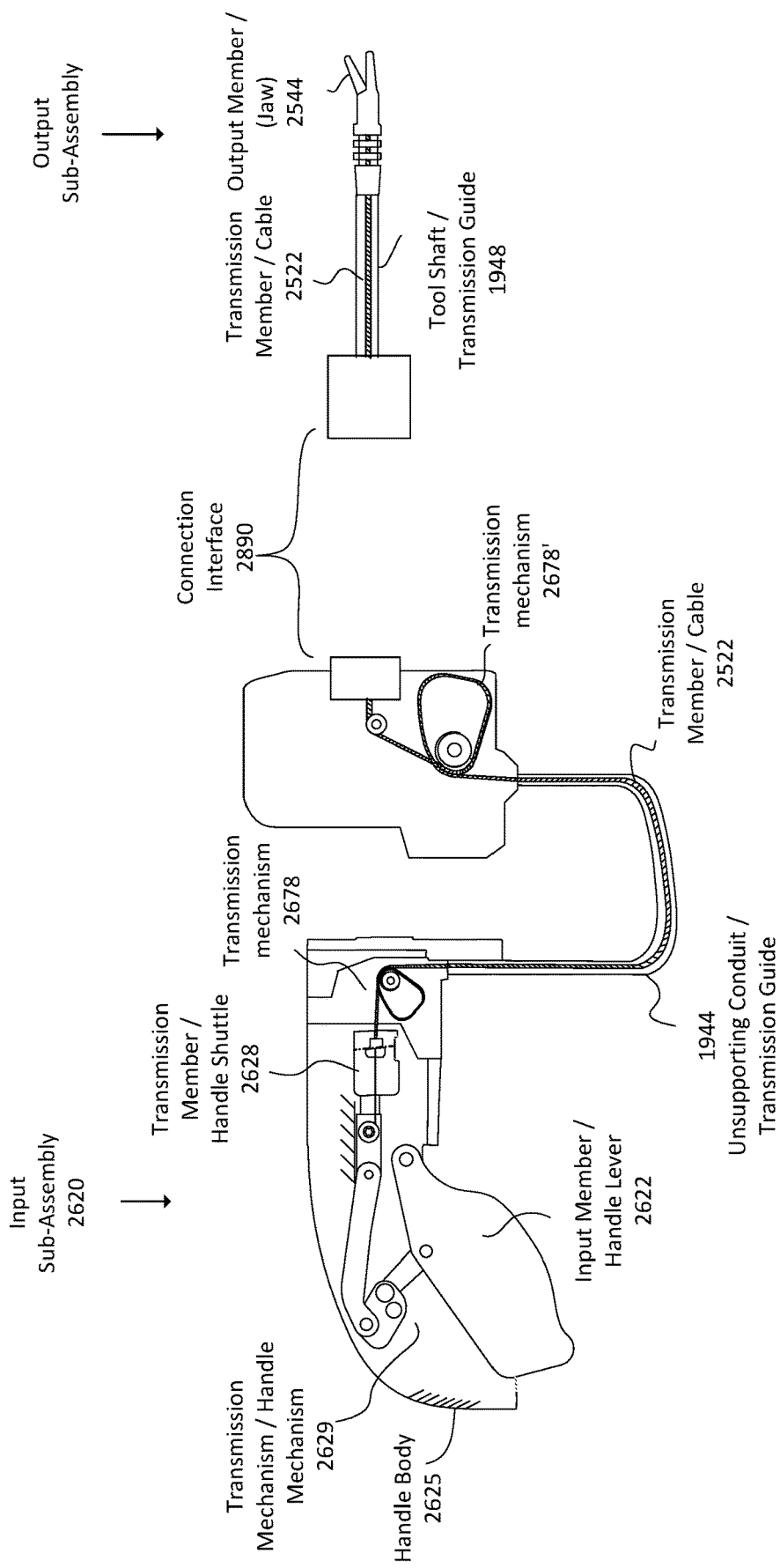
FIG. 28 illustrates an example of a device in which the output sub-system is modularly connected to the transmission and input sub-systems.
Figure 29:
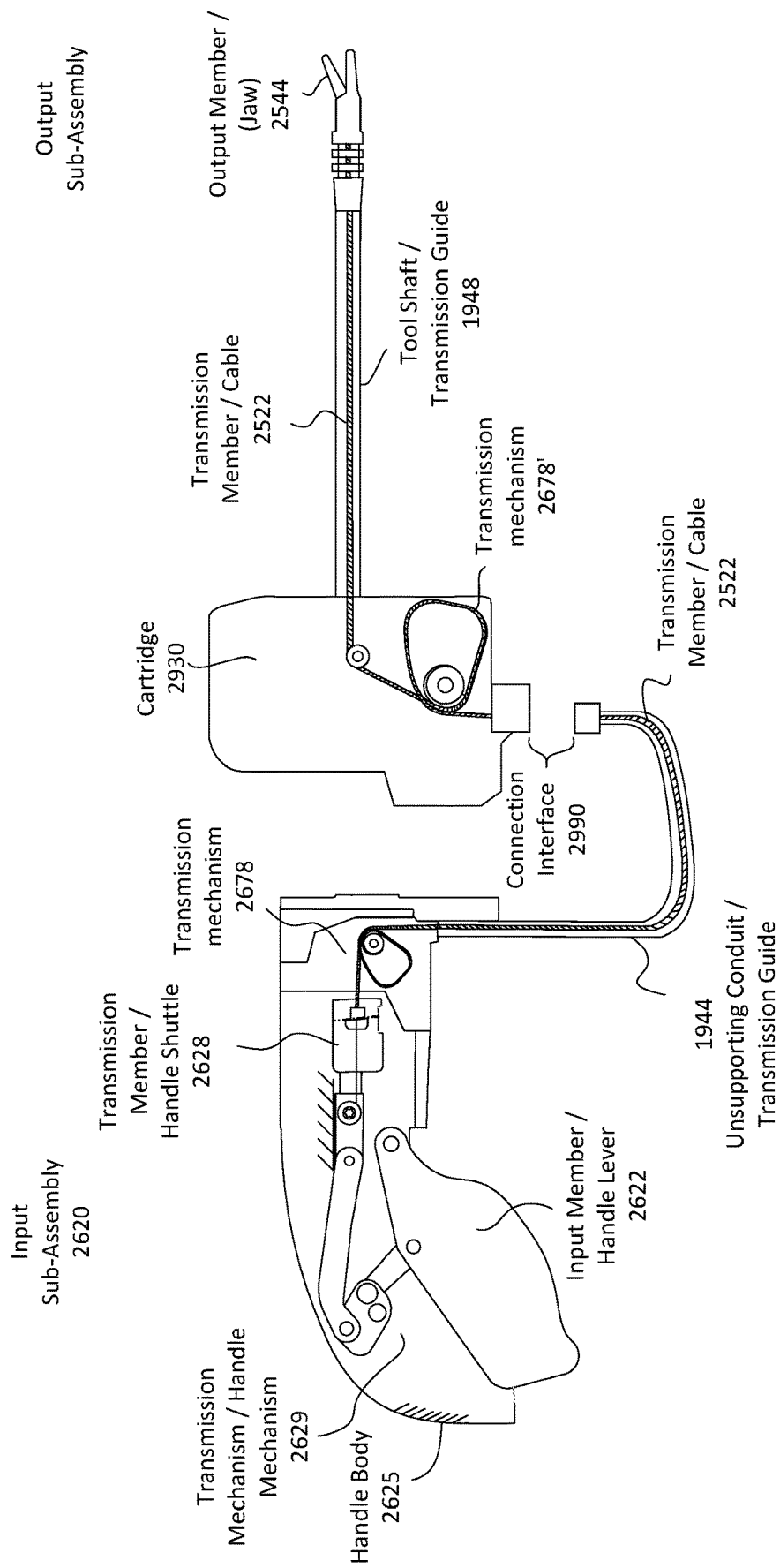
FIG. 29 illustrates an example of a device in which an interface between two assemblies (sub-systems) to form one larger jaw closure transmission system occurs at the proximal end of the flexible transmission member and flexible transmission guide.
Figure 30:
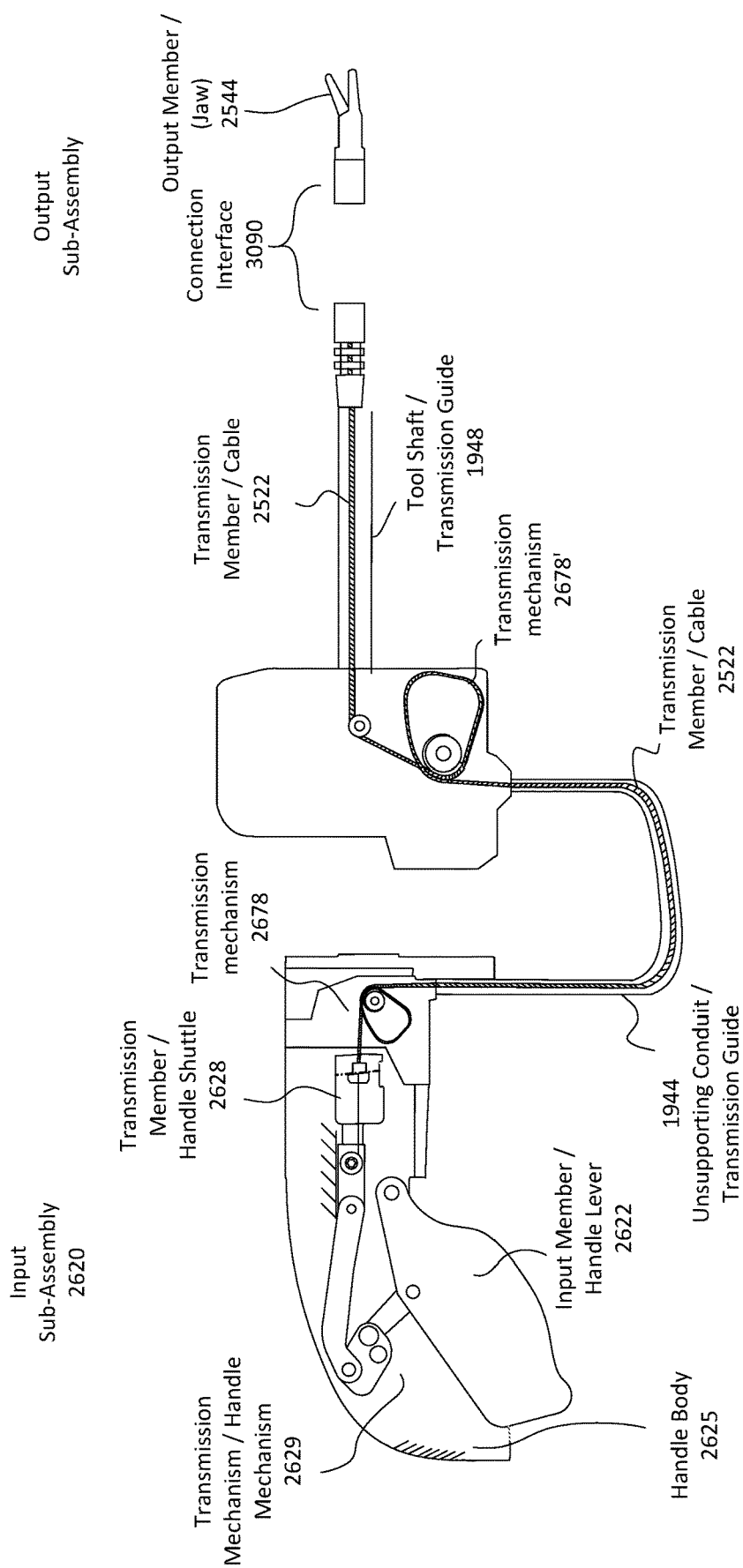
FIG. 30 illustrates that the interface between two assemblies to form one larger jaw closure transmission system can occur at the output sub-system.

The connection between the VCU and the cartridge shown in FIG. 24 occurs at the output of the handle assembly and forms the two sub-systems. The separation between the two assemblies is not required to be at that handle, and other representations of the devices are seen in FIGS. 28, 29, 30. Within these embodiments the interface which separates the device into multiple parts occurs at various locations. Within FIG. 28 the connection 2890 occurs at the proximal region of the elongate shaft member. This location for a separation in the system is natural as it divides the system into a proximal portion which will remain outside of the patent and will not contact the patient and a distal portion which will be inserted into the patent to perform the desired actions. Regarding the input, transmission, and output sub-system this transition between proximal assembly and distal assembly occurred in the middle of the transmission sub-system rather the at the interface between two sub-systems which was demonstrated in the FIG. 24. As FIG. 28 splits the jaw closure transmission system into two assemblies during the transmission sub-system each sub assembly, proximal and distal, will still consist of an input, transmission, and output sub-system. While the proximal assembly includes a transmission cable which is highly flexible in bending while the distal assembly may or may not include a transmission cable which is highly flexible in bending. The flexibility of this embodiment for a jaw closure transmission system enables the use of a solid wire in the distal assembly rather than a highly flexible cable which is easier to clean and reprocess than a cable due to absent of braids and small crevasses within the transmission member.

Another example in which the split in the sub-assemblies occurs at the proximal of the elongate member but distal of the flexible transmission guide is FIG. 29. In this embodiment the distal end of the flexible transmission member has a connector 2990 which interfaces with the cartridge 2930. The transmission sub-system has been split in this embodiment similarly to FIG. 28, however, in this embodiment the there is a transmission mechanism on both the proximal assembly and the distal assembly.

The separation of the jaw closure transmission system is not limited to two assemblies but rather the jaw closure transmission system could be separated into multiple assemblies which achieved the disclosed transmission system when properly assembled.

Figure 31A:
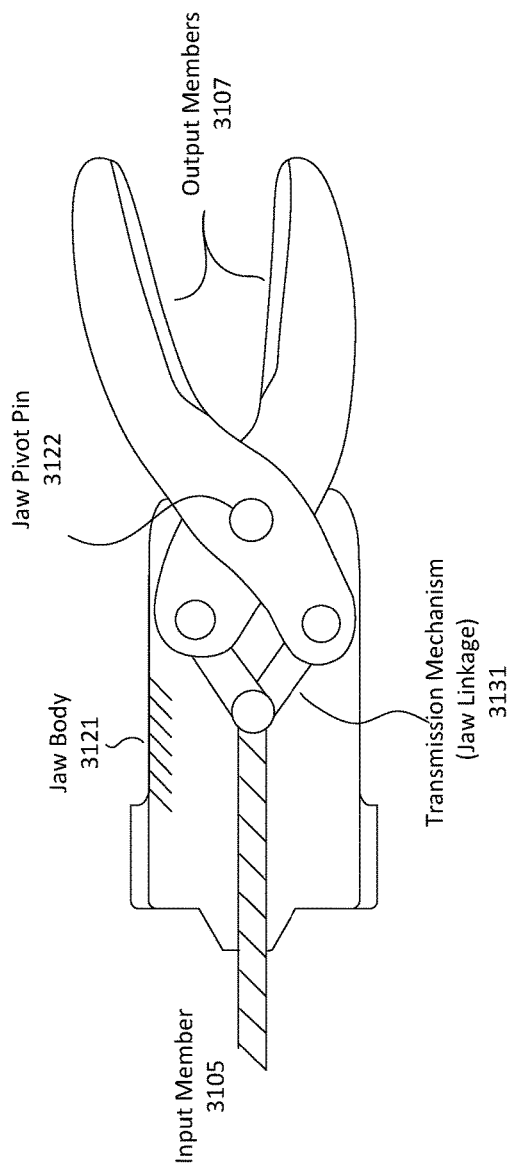
FIGS. 31A-31B show two examples of jaw assemblies.
Figure 31B:
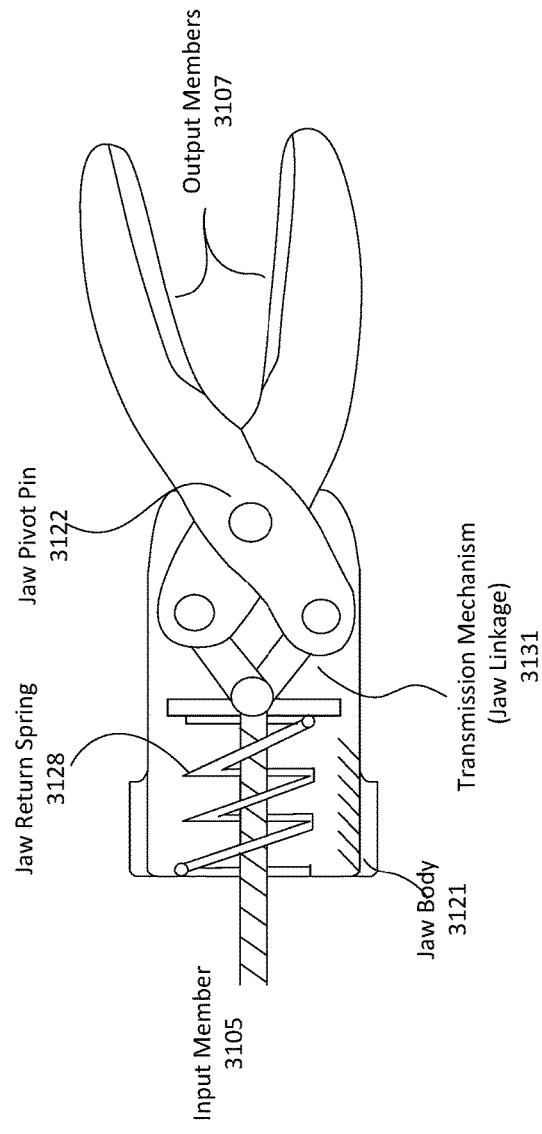

The transition between the different modules (assemblies) can occur between the output sub-system and the transmission system as shown in FIG. 30, similar to what was described above in FIG. 24. The connection interface 2930 is between the jaws 2544 of the jaw assembly (output assembly) and an articulation portion of the jaw assembly. This embodiment may allow for a greater portion of the jaw transmission system to be preserved while the jaw assembly can be replaced. The jaw assembly can be replaced with a variety of jaw configurations which are compatible to the jaw closure transmission system in the proximal assembly. These variations of jaws could consist of jaws which are smaller and optimized to grasp smaller needles or tissues as well larger jaws to grasp larger needles and tissues. Jaw variations are not limited to grasping of ancillary devices and patient material but could consist of profiles optimized other functions which could consist of not limited to cutting. Jaw assemblies which consist of different profiles are shown in FIGS. 31A-31B and 32A-32G. The engagement surfaces in FIGS. 31A-31B could be sharp or blunt, if sharp the jaws would be utilized for cutting while blunt engagement surfaces the jaws could be used for grasping. FIG. 31B incorporates a jaw return spring within the jaw assembly which could be included to aid in the opening of the jaws. Within FIGS. 32A-32G there are three images, FIGS. 32A, 32B and 32C, of the same jaw embodiment but are used to demonstrate the actuation of the mechanism. In FIGS. 31A and 31B, the input member 3105 is housed in the jaw body 3121 and couples to the transmission mechanism (jaw linkage 3131) that operates the jaw pivot pin 3122 driving the movement of the output members 3107.

Connections between two separate assemblies have been shown between an output of one assembly serving as a coupler which engages with the input member of the other assembly. An example of a coupler is described in FIGS. 26A-26B and shown in detail in FIGS. 33A-33C as a handle shuttle which translates linearly when actuated by the handle mechanism. FIGS. 33A and 33B show the interaction between the shuttle and the jaw closure crimp. The shuttle 3329 and jaw closure crimp 3331 in FIG. 33C are designed with engagement surfaces which help eliminate any slack in the transmission system when members are properly assembled. In FIG. 33A-33C, the input member 3305 is coupled to the shuttle 3329 and the output member 3307 is coupled to the jaw closure crimp 3331. The coupling member is not limited to exist only as the output of the handle assembly but could also be located at other locations throughout the transmission system depending on where the interface between two assemblies occur as showing in FIGS. 28, 29, and 30. Additionally, the coupling of the jaw closure transmission system between assemblies is not limited to a translating member, and the coupling of the transmission system can occur by various mechanisms with different engagement features. FIGS. 34A-34B shows a coupling mechanism in which transfers the input 3405 to the attached output 3407 via rotary motion rather than linearly translating. FIGS. 34A and 34B show the coupling mechanism 3474 engaged and disengaged respectively. Coupling mechanisms cannot only be used to transfer motion with a 1:1 transmission ratio from input to output but could be configured to modify the mechanical advantage of the input to the output (e.g., providing other transmission ratios).

Another example of a coupling mechanism 3577 is shown in FIGS. 35A-35B. In this embodiment the input member 3505 and output member 3507 translate linearly however the motion is transferred via rotary motion of the mechanism. The translation of the input member causes the shaft 3564 to rotate (about axis 3569) when the input member is engaged with the gear 3565, the rotation of the shaft which is formed as a lead screw 3564 causes the linear displacement of the hub 3568 which the output member 3507 is connected to. The input member and gear are engaged when the bodies are brought together which is shown in FIG. 35B.

A configurable transmission system is not limited to the addition of transmission mechanisms to achieve the desired performance but may also include replacing existing transmission mechanisms of the system to achieve a different performance of the device. An example of an embodiment which replaces a transmission mechanism includes a device in which the output sub-system is replaced. The embodiments previously shown include a medical device with a needle driver Jaw. By incorporating a configurable transmission system, the needle driver jaw could be replaced with a pair of smaller or larger jaws optimized for driving various needles, the jaws could also be replaced with but not limited to; a pair of jaws capable of applying medical clips, cutting tissue, or even griping tissue shown in FIGS. 31A-31B and 32A-32G. By conserving most of the transmission system of the device and only replacing select transmission mechanisms, the same device can be used for multiple applications eliminating the need for multiple instruments during a case. Reducing the number of instruments required for a case can be very cost effective to the hospital as each instrument used is required to either be cleaned after use or discarded after every use. In FIG. 32A the input member 3205 operates a mechanism (shown as a pulley) within the jaw body 3221 that drives movement of the output member (blade 3207).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be conjointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a subset of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device having a jaw assembly actuated by a transmission cable, the device comprising:
    an elongate, flexible transmission guide, wherein the transmission cable is routed through the elongate, flexible transmission guide;
    an input assembly at a proximal end of the elongate, flexible transmission guide, the input assembly comprising an input body and an input member, the input member coupled to the proximal end of the transmission cable, wherein the input member has an input stroke relative to the input body, further wherein the input stroke includes a first part that corresponds to a displacement of 30% to 70% of the full displacement of the input member and a second part that corresponds to the remaining displacement of the input member; and
    wherein the jaw assembly is distal to the elongate, flexible transmission guide, the jaw assembly having a first jaw, a second jaw, and a jaw input coupling the transmission cable to the second jaw or the first and second jaw, wherein the jaw assembly has an open configuration when the first and second jaws are fully open relative to each other and a closed configuration when the first and second jaws are closed;
    further wherein displacement of the input member relative to the input body corresponding to the first part of the input stroke actuates the proximal end of the transmission cable which in turn actuates the jaw input, which in turn closes the first and second jaws until the first and second jaws reach a stop, and thereafter the displacement of the input member relative to the input body corresponding to the second part of the input stroke stretches the transmission cable, wherein the resulting tension in the transmission cable is converted by the jaw assembly to an increasing force between the first and second jaws.

2. The device of claim 1, further comprising one or more intermediate transmissions, wherein the one or more intermediate transmissions are configured to provide a first mechanical advantage during the first part of the input stroke and a second mechanical advantage that is greater than the first mechanical advantage during the second part of the input stroke.

3. The device of claim 1, wherein the input assembly comprises a handle assembly, and wherein the input body is formed by a handle body or is removably coupled to the handle body.

4. The device of claim 3, wherein the handle assembly includes an input lever coupled to the input member when the input body is removably coupled with the handle body.

5. The device of claim 1, wherein the input assembly comprises a linkage or a cam.

6. The device of claim 1, wherein the input assembly comprises a handle assembly and further wherein the input member comprises an input lever.

7. The device of claim 1, wherein the elongate transmission guide comprises a first region of conduit that is flexible in bending.

8. The device of claim 1, wherein the elongate transmission guide is stiff at least along a region through which the transmission cable is routed.

9. The device of claim 1, wherein the input assembly further comprises an input assembly output coupled to the proximal end of the transmission cable, further wherein the input assembly output comprises one or more of: a shuttle, a push rod, or a pull rod.

10. The device of claim 1, further comprising a jaw base to which either or both the first and second jaws are pivotally coupled.

11. The device of claim 1, wherein the jaw input comprises a jaw pulley, and the jaw assembly comprises a cam surface between the jaw pulley and the second jaw.

12. The device of claim 1, further comprising a releasable latch configured to hold the input member locked in a closed position at the end of the input stroke.

13. The device of claim 1, wherein one or both of the jaw assembly and the input assembly are modularly connected to the elongate transmission guide and the transmission cable of the device.

14. A device having a jaw assembly actuated by a transmission cable having a finite stiffness in a transmission direction, the device comprising:
  an elongate, flexible transmission guide, wherein the transmission cable is routed through the elongate, flexible transmission guide;
  an input assembly at a proximal end of the elongate, flexible transmission guide, the input assembly comprising an input body and an input member, the input member coupled to the proximal end of the transmission cable, wherein the input member has an input stroke relative to the input body, further wherein the input stroke includes a first part that corresponds to a displacement of 30% to 70% of the full displacement of the input member and a second part that corresponds to the remaining displacement of the input member;
  an intermediate transmission coupled to the transmission cable and configured to provide a first mechanical advantage during the first part of the input stroke and a second mechanical advantage that is greater than the first mechanical advantage during the second part of the input stroke; and
  wherein the jaw assembly is distal to the elongate, flexible transmission guide, the jaw assembly having a first jaw, a second jaw, and a jaw input coupling the transmission cable to the second jaw or the first and second jaw, wherein the jaw assembly has an open configuration when the first and second jaws are fully open relative to each other and a closed configuration when the first and second jaws are closed;
  further wherein the displacement of the input member relative to the input body corresponding to the first part of the input stroke actuates the proximal end of the transmission cable which in turn actuates the jaw input, which in turn closes the first and second jaws until the first and second jaws reach a stop, and thereafter the displacement of the input member relative to the input body corresponding to the second part of the input stroke stretches the transmission cable, wherein the resulting tension in the transmission cable is converted by the jaw assembly to an increasing force between the first and second jaws.

15. The device of claim 14, wherein the input assembly is configured to removably couple to a handle assembly so that the input body couples to a handle body and the input member couples to an input lever of the handle assembly.

16. The device of claim 14, wherein the input assembly comprises a linkage or a cam.

17. The device of claim 14, wherein the input assembly comprises a six-bar linkage.

18. A method of operating a medical device to close a jaw assembly of the medical device, wherein the medical device comprises an elongate transmission guide, a transmission cable within the transmission guide, and an input assembly at the proximal end of the transmission cable, the input assembly having an input member coupled to the transmission cable, wherein the transmission cable is coupled to an input of the jaw assembly, wherein the jaw assembly is distal to the elongate transmission guide, the method comprising:
  actuating the input member to apply tension to the transmission cable during a first part of an input stroke of the input assembly to close a first and second jaw of the jaw assembly from an open configuration until the first and second jaws reach a stop;
  continuing to actuate the input member during a second part of the input stroke after the first and second jaws have reached the stop and stretching the transmission cable;
  wherein the input stroke consists of a displacement of the input member, and further wherein the input member transitions from the first part of the input stroke to the second part of the input stroke when the input member is between 30% and 70% displaced; and
  applying a first mechanical advantage to the first and second jaws during the first part of the input stroke and applying a second mechanical advantage to the first and second jaws that is greater than the first mechanical advantage during the second part of the input stroke.

19. The method of claim 18, wherein the first mechanical advantage and the second mechanical advantage are applied by an intermediate transmission coupled to the transmission cable between the input assembly and the jaw assembly.

20. The method of claim 18, further comprising grasping an object between the first and second jaws, wherein the first and second jaws reach the stop when the object is secured between the first and second jaws.

21. The method of claim 18, further comprising locking the input member in a fully closed position.

22. The method of claim 18, further comprising releasing the input member to transition from the second part of the input stroke to the first part of the input stroke, reducing the tension on the transmission cable and reducing the stretch of the transmission cable before translating the transmission cable at the distal end so that the first and second jaws open.

\* \* \* \* \*